(12) United States Patent
Ma

(10) Patent No.: US 7,842,048 B2
(45) Date of Patent: Nov. 30, 2010

(54) ARTICULATING SUTURE DEVICE AND METHOD

(75) Inventor: Dawn Ma, San Jose, CA (US)

(73) Assignee: Abbott Laboratories, Abbott Park, IL (US)

( * ) Notice: Subject to any disclaimer, the term of this patent is extended or adjusted under 35 U.S.C. 154(b) by 1001 days.

(21) Appl. No.: 11/465,527

(22) Filed: Aug. 18, 2006

(65) Prior Publication Data

US 2008/0045979 A1 Feb. 21, 2008

(51) Int. Cl.
*A61B 17/04* (2006.01)
(52) U.S. Cl. .................. 606/144; 606/139; 606/148
(58) Field of Classification Search ............... 606/139, 606/144, 145, 148
See application file for complete search history.

(56) References Cited

U.S. PATENT DOCUMENTS

| | | |
|---|---|---|
| 312,408 A | 2/1885 | Wackerhagen |
| 597,165 A | 1/1898 | Hall |
| 659,422 A | 10/1900 | Shidler |
| 989,231 A | 4/1911 | Davis |
| 1,625,602 A | 4/1927 | Gould et al. |
| 2,012,776 A | 8/1935 | Roeder |
| 2,127,903 A | 8/1938 | Bowen |
| 2,371,978 A | 3/1945 | Perham |
| 2,397,823 A | 4/1946 | Walter |
| RE22,857 E | 3/1947 | Ogburn |
| 2,588,589 A | 3/1952 | Tauber |
| 2,646,045 A | 7/1953 | Priestley |
| 2,692,599 A | 10/1954 | Creelman |
| 2,941,489 A | 6/1960 | Fischbein |
| 2,959,172 A | 11/1960 | Held |
| 3,033,156 A | 5/1962 | Verlish |
| 3,104,666 A | 9/1963 | Hale et al. |
| 3,197,102 A | 7/1965 | Bates et al. |
| 3,359,983 A | 12/1967 | Northey |
| 3,413,397 A | 11/1968 | Bierbaum et al. |
| 3,422,181 A | 1/1969 | Chirgwin, Jr. |
| 3,470,875 A | 10/1969 | Johnson |

(Continued)

FOREIGN PATENT DOCUMENTS

DE 912619 5/1954

(Continued)

OTHER PUBLICATIONS

U.S. Appl. No. 90/006,469, filed Nov. 29, 2002, Modesitt.

(Continued)

*Primary Examiner*—Julian W Woo
(74) *Attorney, Agent, or Firm*—Workman Nydegger

(57) ABSTRACT

Devices, systems, and methods for suturing of body lumens allow the suturing of vascular puncture sites located at the distal end of a percutaneous tissue tract. An elongated articulated foot of the device can be inserted through the penetration and actuated so that the foot extends along the lumenal axis. The foot can carry suturing attachment cuffs with one end of the cuff adapted to receive a needle, while the other end receives suture. A portion of the foot and/or lumen of the shaft can receive a portion of the suture and can include friction reducing structure that aid with movement of the sutured during removal of the cuffs from within the penetration.

18 Claims, 45 Drawing Sheets

U.S. PATENT DOCUMENTS

| | | |
|---|---|---|
| 3,587,115 A | 6/1971 | Shiley |
| 3,630,205 A | 12/1971 | Listner |
| 3,653,388 A | 4/1972 | Tenckhoff |
| 3,665,926 A | 5/1972 | Flores |
| 3,776,237 A | 12/1973 | Hill et al. |
| 3,802,438 A | 4/1974 | Wolvek |
| 3,820,544 A | 6/1974 | Semm |
| 3,840,017 A | 10/1974 | Violante |
| 3,874,388 A | 4/1975 | King et al. |
| 3,878,848 A | 4/1975 | Hiebert |
| 3,918,455 A | 11/1975 | Coplan |
| 3,926,194 A | 12/1975 | Greenberg et al. |
| 3,939,820 A | 2/1976 | Grayzel |
| 3,985,138 A | 10/1976 | Jarvik |
| 4,018,228 A | 4/1977 | Goosen |
| 4,109,658 A | 8/1978 | Hughes |
| 4,128,100 A | 12/1978 | Wendorff |
| 4,135,623 A | 1/1979 | Thyen |
| 4,161,951 A | 7/1979 | Scanlan, Jr. |
| 4,168,073 A | 9/1979 | LaRue |
| 4,182,339 A | 1/1980 | Hardy, Jr. |
| 4,185,636 A | 1/1980 | Gabbay et al. |
| 4,216,776 A | 8/1980 | Downie et al. |
| 4,217,665 A | 8/1980 | Bex et al. |
| 4,235,177 A | 11/1980 | Arbuckle |
| 4,235,238 A | 11/1980 | Ogiu et al. |
| 4,316,469 A | 2/1982 | Kapitanov |
| 4,317,445 A | 3/1982 | Robinson |
| 4,411,654 A | 10/1983 | Boarini et al. |
| 4,412,832 A | 11/1983 | Kling et al. |
| 4,437,465 A | 3/1984 | Nomoto et al. |
| 4,469,101 A | 9/1984 | Coleman et al. |
| 4,492,229 A | 1/1985 | Grunwald |
| 4,493,323 A | 1/1985 | Albright et al. |
| 4,553,543 A | 11/1985 | Amarasinghe |
| 4,586,614 A | 5/1986 | Ger |
| 4,587,969 A | 5/1986 | Gillis |
| 4,596,559 A | 6/1986 | Fleishhacker |
| 4,629,450 A | 12/1986 | Suzuki et al. |
| 4,651,733 A | 3/1987 | Mobin-Uddin |
| 4,702,250 A | 10/1987 | Orvil et al. |
| 4,723,549 A | 2/1988 | Wholey et al. |
| 4,738,666 A | 4/1988 | Fuqua |
| 4,744,364 A | 5/1988 | Kensey |
| 4,748,982 A | 6/1988 | Horzewski et al. |
| 4,803,984 A | 2/1989 | Narayanan et al. |
| 4,836,205 A | 6/1989 | Barrett |
| 4,848,341 A | 7/1989 | Ahmad |
| 4,852,568 A | 8/1989 | Kensey |
| 4,890,612 A | 1/1990 | Kensey |
| 4,898,155 A | 2/1990 | Ovil et al. |
| 4,911,164 A | 3/1990 | Roth |
| 4,917,089 A | 4/1990 | Sideris |
| 4,926,860 A | 5/1990 | Stice et al. |
| 4,929,246 A | 5/1990 | Sinofsky |
| 4,935,027 A | 6/1990 | Yoon |
| 4,950,285 A | 8/1990 | Wilk |
| 4,957,498 A | 9/1990 | Caspari et al. |
| 4,966,600 A | 10/1990 | Songer et al. |
| 4,981,149 A | 1/1991 | Yoon et al. |
| 4,983,168 A | 1/1991 | Moorehead |
| 4,984,581 A | 1/1991 | Stice |
| 5,002,563 A | 3/1991 | Pyka et al. |
| 5,009,643 A | 4/1991 | Reich et al. |
| 5,021,059 A | 6/1991 | Kensey et al. |
| 5,037,433 A | 8/1991 | Wilk et al. |
| 5,047,039 A | 9/1991 | Avant et al. |
| 5,059,201 A | 10/1991 | Asnis |
| 5,061,274 A | 10/1991 | Kensey |
| 5,074,874 A | 12/1991 | Yoon et al. |
| 5,078,721 A | 1/1992 | McKeating |
| 5,080,664 A | 1/1992 | Jain |
| 5,100,419 A | 3/1992 | Ehlers |
| 5,100,422 A | 3/1992 | Berguer et al. |
| 5,100,432 A | 3/1992 | Matsutani |
| 5,109,780 A | 5/1992 | Slouf et al. |
| 5,129,912 A | 7/1992 | Noda et al. |
| 5,129,913 A | 7/1992 | Ruppert |
| 5,144,961 A | 9/1992 | Chen et al. |
| 5,147,373 A | 9/1992 | Ferzli |
| 5,156,788 A | 10/1992 | Chesterfield et al. |
| 5,160,339 A | 11/1992 | Chen et al. |
| 5,171,251 A | 12/1992 | Bregen et al. |
| 5,178,629 A | 1/1993 | Kammerer |
| 5,192,294 A | 3/1993 | Blake, III |
| 5,192,301 A | 3/1993 | Kamiya et al. |
| 5,192,302 A | 3/1993 | Kensey et al. |
| 5,207,703 A | 5/1993 | Jain |
| 5,211,650 A | 5/1993 | Noda |
| 5,217,470 A | 6/1993 | Weston |
| 5,217,485 A | 6/1993 | Liv et al. |
| 5,219,358 A | 6/1993 | Bendel et al. |
| 5,222,974 A | 6/1993 | Kensey et al. |
| 5,234,443 A | 8/1993 | Phan et al. |
| 5,234,445 A | 8/1993 | Walker et al. |
| 5,242,427 A | 9/1993 | Bilweis |
| 5,250,033 A | 10/1993 | Evans et al. |
| 5,250,053 A | 10/1993 | Snyder |
| 5,254,105 A | 10/1993 | Haaga |
| 5,254,126 A | 10/1993 | Filipi et al. |
| 5,258,003 A | 11/1993 | Ciaglia et al. |
| 5,259,846 A | 11/1993 | Granger et al. |
| 5,279,311 A | 1/1994 | Snyder |
| 5,281,236 A | 1/1994 | Bagnato et al. |
| 5,281,237 A | 1/1994 | Gimpelson |
| 5,284,485 A | 2/1994 | Kammerer et al. |
| 5,285,945 A | 2/1994 | Brinkerhoff et al. |
| 5,289,963 A | 3/1994 | McGarry et al. |
| 5,290,284 A | 3/1994 | Adair |
| 5,290,297 A | 3/1994 | Phillips |
| 5,292,309 A | 3/1994 | VanTassel et al. |
| 5,292,327 A | 3/1994 | Dodd et al. |
| 5,292,332 A | 3/1994 | Lee |
| 5,293,881 A | 3/1994 | Green et al. |
| 5,295,993 A | 3/1994 | Green |
| 5,300,085 A | 4/1994 | Yock |
| 5,304,184 A | 4/1994 | Hathaway et al. |
| 5,304,185 A | 4/1994 | Taylor |
| 5,306,254 A | 4/1994 | Nash et al. |
| 5,312,024 A | 5/1994 | Grant et al. |
| 5,312,423 A | 5/1994 | Rosenbluth et al. |
| 5,318,578 A | 6/1994 | Hasson |
| 5,320,629 A | 6/1994 | Noda et al. |
| 5,320,632 A | 6/1994 | Heidmueller |
| 5,330,445 A | 7/1994 | Haaga |
| 5,334,217 A | 8/1994 | Das |
| 5,336,229 A | 8/1994 | Noda |
| 5,336,230 A | 8/1994 | Leichtling et al. |
| 5,336,231 A | 8/1994 | Adair |
| 5,342,369 A | 8/1994 | Harryman, II |
| 5,353,974 A | 10/1994 | Maurizio |
| 5,354,312 A | 10/1994 | Brinkerhoff et al. |
| 5,364,407 A | 11/1994 | Poll |
| 5,364,408 A | 11/1994 | Gordon |
| 5,368,595 A | 11/1994 | Lewis |
| 5,368,601 A | 11/1994 | Sauer et al. |
| 5,374,275 A | 12/1994 | Bradley et al. |
| 5,374,278 A | 12/1994 | Chesterfield et al. |
| 5,376,096 A | 12/1994 | Foster |
| 5,383,896 A | 1/1995 | Gershony et al. |
| 5,385,569 A | 1/1995 | Swor |
| 5,387,221 A | 2/1995 | Bisgaard |
| 5,387,227 A | 2/1995 | Grice |
| 5,391,176 A | 2/1995 | de la Torre |

| | | | | | |
|---|---|---|---|---|---|
| 5,391,182 A | 2/1995 | Chin | 5,643,295 A | 7/1997 | Yoon |
| 5,395,332 A | 3/1995 | Ressemann et al. | 5,643,318 A | 7/1997 | Tsukernik et al. |
| 5,395,349 A | 3/1995 | Quiachon et al. | 5,649,959 A | 7/1997 | Hannam et al. |
| 5,397,310 A | 3/1995 | Chu et al. | 5,662,664 A | 9/1997 | Gordon et al. |
| 5,397,325 A | 3/1995 | Delia Badia et al. | 5,669,917 A | 9/1997 | Sauer et al. |
| 5,403,329 A | 4/1995 | Hinchcliffe | 5,676,689 A | 10/1997 | Kensey et al. |
| 5,403,331 A | 4/1995 | Chesterfield et al. | 5,700,273 A | 12/1997 | Buelna et al. |
| 5,403,338 A | 4/1995 | Milo | 5,707,379 A | 1/1998 | Fleenor et al. |
| 5,411,481 A | 5/1995 | Allen et al. | 5,713,910 A | 2/1998 | Gordon et al. |
| 5,413,571 A | 5/1995 | Katsaros et al. | 5,716,369 A | 2/1998 | Riza |
| 5,417,699 A | 5/1995 | Klein et al. | 5,720,574 A | 2/1998 | Barella |
| 5,425,705 A | 6/1995 | Evard et al. | 5,720,757 A | 2/1998 | Hathaway et al. |
| 5,425,740 A | 6/1995 | Hutchinson, Jr. | 5,725,552 A | 3/1998 | Kotula et al. |
| 5,431,666 A | 7/1995 | Sauer et al. | 5,728,109 A | 3/1998 | Schulze et al. |
| 5,433,700 A | 7/1995 | Peters | 5,728,114 A | 3/1998 | Evans et al. |
| 5,452,733 A | 9/1995 | Sterman et al. | 5,728,133 A | 3/1998 | Kontos |
| 5,454,822 A | 10/1995 | Schob et al. | 5,728,151 A | 3/1998 | Garrison et al. |
| 5,454,834 A | 10/1995 | Boebel et al. | 5,741,276 A | 4/1998 | Poloyko et al. |
| 5,458,574 A | 10/1995 | Machold et al. | 5,741,280 A | 4/1998 | Fleenor |
| 5,464,426 A | 11/1995 | Bonutti | 5,746,755 A | 5/1998 | Wood et al. |
| 5,466,241 A | 11/1995 | Leroy et al. | 5,749,890 A | 5/1998 | Shaknovich |
| 5,470,338 A | 11/1995 | Whitfield et al. | 5,755,727 A | 5/1998 | Kontos |
| 5,476,469 A | 12/1995 | Hathaway et al. | 5,759,188 A | 6/1998 | Yoon |
| 5,476,470 A | 12/1995 | Fitzgibbons, Jr. | 5,766,183 A | 6/1998 | Sauer |
| 5,478,309 A | 12/1995 | Sweezer et al. | 5,766,186 A | 6/1998 | Faraz et al. |
| 5,478,353 A | 12/1995 | Yoon | 5,766,217 A | 6/1998 | Christy |
| 5,480,407 A | 1/1996 | Wan et al. | 5,769,862 A | 6/1998 | Kammerer et al. |
| 5,486,190 A | 1/1996 | Green | 5,779,719 A | 7/1998 | Klein et al. |
| 5,489,295 A | 2/1996 | Piplani et al. | 5,782,860 A | 7/1998 | Epstein et al. |
| 5,496,332 A | 3/1996 | Sierra et al. | 5,782,861 A | 7/1998 | Cragg et al. |
| 5,507,744 A | 4/1996 | Tay et al. | 5,792,151 A | 8/1998 | Heck et al. |
| 5,507,755 A | 4/1996 | Gresl et al. | 5,792,152 A | 8/1998 | Klein et al. |
| 5,507,757 A | 4/1996 | Sauer et al. | 5,797,928 A | 8/1998 | Kogasaka |
| 5,507,758 A | 4/1996 | Thomason et al. | 5,797,929 A | 8/1998 | Andreas et al. |
| 5,509,902 A | 4/1996 | Raulerson | 5,799,661 A | 9/1998 | Boyd et al. |
| 5,520,655 A | 5/1996 | Davila et al. | 5,810,849 A | 9/1998 | Kontos |
| 5,520,665 A | 5/1996 | Fleetwood | 5,810,850 A | 9/1998 | Hathaway et al. |
| 5,520,702 A | 5/1996 | Sauer et al. | 5,817,113 A | 10/1998 | Gifford, III et al. |
| 5,527,321 A | 6/1996 | Hinchliffe | 5,820,631 A | 10/1998 | Nobles |
| 5,527,322 A | 6/1996 | Klein et al. | 5,824,010 A | 10/1998 | McDonald |
| D372,310 S | 7/1996 | Hartnett | 5,824,111 A | 10/1998 | Schall et al. |
| 5,531,700 A | 7/1996 | Moore et al. | 5,830,125 A | 11/1998 | Scribner et al. |
| 5,536,273 A | 7/1996 | Lehrer | 5,836,955 A | 11/1998 | Buelna et al. |
| 5,540,701 A | 7/1996 | Sharkey et al. | 5,836,956 A | 11/1998 | Buelna et al. |
| 5,540,704 A | 7/1996 | Gordon et al. | 5,846,253 A | 12/1998 | Buelna et al. |
| 5,545,171 A | 8/1996 | Sharkey et al. | 5,848,714 A | 12/1998 | Robson et al. |
| 5,545,178 A | 8/1996 | Kensey et al. | 5,855,585 A | 1/1999 | Kontos |
| 5,545,180 A | 8/1996 | Le et al. | 5,860,990 A | 1/1999 | Nobles et al. |
| 5,549,618 A | 8/1996 | Fleenor et al. | 5,860,991 A | 1/1999 | Klein et al. |
| 5,549,631 A | 8/1996 | Bonutti | 5,861,005 A | 1/1999 | Kontos |
| 5,554,162 A | 9/1996 | DeLange | 5,871,490 A | 2/1999 | Schulze et al. |
| 5,562,684 A | 10/1996 | Kammerer | 5,871,502 A | 2/1999 | Suryadevara |
| 5,562,686 A | 10/1996 | Sauer et al. | 5,873,876 A | 2/1999 | Christy |
| 5,562,688 A | 10/1996 | Riza | 5,876,411 A | 3/1999 | Kontos |
| 5,562,728 A | 10/1996 | Lazarus et al. | 5,897,487 A | 4/1999 | Ouchi |
| 5,567,435 A | 10/1996 | Hubbell et al. | 5,897,564 A | 4/1999 | Schulze et al. |
| 5,569,269 A | 10/1996 | Hart et al. | 5,902,311 A | 5/1999 | Andreas et al. |
| 5,569,271 A | 10/1996 | Hoel | 5,904,697 A | 5/1999 | Doi et al. |
| 5,571,120 A | 11/1996 | Yoon | 5,904,690 A | 5/1999 | Middleman et al. |
| 5,573,540 A | 11/1996 | Yoon | 5,904,697 A | 5/1999 | Gifford, III et al. |
| 5,584,842 A | 12/1996 | Fogarty et al. | 5,906,631 A | 5/1999 | Imran |
| 5,591,177 A | 1/1997 | Lehrer | 5,919,207 A | 7/1999 | Taheri |
| 5,591,179 A | 1/1997 | Edelstein | 5,921,994 A | 7/1999 | Andreas et al. |
| 5,591,206 A | 1/1997 | Moufarrege | 5,928,266 A | 7/1999 | Kontos |
| 5,593,421 A | 1/1997 | Bauer | 5,951,590 A | 9/1999 | Goldfarb |
| 5,603,718 A | 2/1997 | Xu | 5,954,732 A | 9/1999 | Hart et al. |
| 5,607,435 A | 3/1997 | Sachdeva et al. | 5,957,936 A | 9/1999 | Yoon et al. |
| 5,609,597 A | 3/1997 | Lehrer | 5,957,937 A | 9/1999 | Yoon |
| 5,611,794 A | 3/1997 | Sauer et al. | 5,957,938 A | 9/1999 | Zhu et al. |
| 5,613,974 A | 3/1997 | Andreas et al. | 5,964,773 A | 10/1999 | Greenstein |
| 5,613,975 A | 3/1997 | Christy | 5,964,782 A | 10/1999 | Lafontaine et al. |
| 5,626,588 A | 5/1997 | Sauer et al. | 5,972,030 A | 10/1999 | Garrison et al. |
| 5,643,289 A | 7/1997 | Sauer et al. | 5,976,161 A | 11/1999 | Kirsch et al. |

| | | | | | | |
|---|---|---|---|---|---|---|
| 5,980,539 | A | 11/1999 | Kontos | 7,179,266 B2 | 2/2007 | Kontos |
| 5,997,555 | A | 12/1999 | Kontos | 7,229,458 B2 | 6/2007 | Boecker et al. |
| 6,001,109 | A | 12/1999 | Kontos | 7,235,087 B2 | 6/2007 | Modesitt et al. |
| 6,022,372 | A | 2/2000 | Kontos | 7,316,704 B2 | 1/2008 | Bagaoisan et al. |
| 6,024,747 | A | 2/2000 | Kontos | 7,326,230 B2 | 2/2008 | Ravikumar |
| 6,036,699 | A | 3/2000 | Andreas et al. | 7,331,979 B2 | 2/2008 | Khosravi et al. |
| 6,042,601 | A | 3/2000 | Smith | 7,335,220 B2 | 2/2008 | Khosravi et al. |
| 6,048,351 | A | 4/2000 | Gordon et al. | 7,361,183 B2 | 4/2008 | Ginn |
| 6,048,354 | A | 4/2000 | Lawrence | 7,361,185 B2 | 4/2008 | O'Malley et al. |
| 6,048,357 | A | 4/2000 | Kontos | 7,377,927 B2 | 5/2008 | Burdulis, Jr. et al. |
| 6,077,276 | A | 6/2000 | Kontos | 7,390,328 B2 | 6/2008 | Modesitt |
| 6,077,279 | A | 6/2000 | Kontos | 7,393,363 B2 | 7/2008 | Ginn |
| 6,117,144 | A | 9/2000 | Nobles et al. | 7,462,188 B2 | 12/2008 | McIntosh |
| 6,117,145 | A | 9/2000 | Wood et al. | 2001/0046518 A1 | 11/2001 | Sawhney |
| 6,126,675 | A | 10/2000 | Shchervinsky et al. | 2002/0095164 A1 | 7/2002 | Andreas et al. |
| 6,132,439 | A | 10/2000 | Kontos | 2002/0099389 A1 | 7/2002 | Michler et al. |
| 6,132,440 | A | 10/2000 | Hathaway et al. | 2002/0106409 A1 | 8/2002 | Sawhney et al. |
| 6,136,010 | A | 10/2000 | Modesitt et al. | 2002/0177876 A1 | 11/2002 | Roby et al. |
| 6,139,556 | A | 10/2000 | Kontos | 2003/0093093 A1 | 5/2003 | Modesitt et al. |
| 6,152,936 | A | 11/2000 | Christy et al. | 2003/0195529 A1 | 10/2003 | Takamoto et al. |
| 6,165,204 | A | 12/2000 | Levinson et al. | 2004/0009205 A1 | 1/2004 | Sawhney |
| 6,190,396 | B1 | 2/2001 | Whitin et al. | 2004/0092964 A1 | 5/2004 | Modesitt et al. |
| 6,197,042 | B1 | 3/2001 | Ginn et al. | 2004/0093027 A1 | 5/2004 | Fabisiak et al. |
| 6,206,893 | B1 | 3/2001 | Klein et al. | 2004/0097978 A1 | 5/2004 | Modesitt et al. |
| 6,245,079 | B1 | 6/2001 | Nobles et al. | 2004/0122449 A1 | 6/2004 | Modesitt |
| 6,248,124 | B1 | 6/2001 | Pedros et al. | 2004/0127940 A1 | 7/2004 | Ginn et al. |
| 6,296,657 | B1 | 10/2001 | Brucker | 2004/0143290 A1 | 7/2004 | Brightbill |
| 6,348,059 | B1 | 2/2002 | Hathaway et al. | 2004/0158127 A1 | 8/2004 | Okada |
| 6,355,050 | B1 | 3/2002 | Andreas et al. | 2004/0158287 A1 | 8/2004 | Cragg et al. |
| 6,358,258 | B1 | 3/2002 | Arcia et al. | 2004/0167511 A1 | 8/2004 | Buehlmann et al. |
| 6,395,015 | B1 | 5/2002 | Borst et al. | 2004/0181238 A1 | 9/2004 | Zarbatany et al. |
| 6,428,472 | B1 | 8/2002 | Haas | 2004/0186487 A1 | 9/2004 | Klein et al. |
| 6,428,549 | B1 | 8/2002 | Kontos | 2004/0191277 A1 | 9/2004 | Sawhney et al. |
| 6,436,109 | B1 | 8/2002 | Kontos | 2004/0210251 A1 | 10/2004 | Kontos |
| 6,443,963 | B1 | 9/2002 | Baldwin et al. | 2004/0215232 A1 | 10/2004 | Belhe et al. |
| 6,451,031 | B1 | 9/2002 | Kontos | 2004/0225301 A1 | 11/2004 | Roop et al. |
| 6,511,489 | B2 | 1/2003 | Field et al. | 2004/0267193 A1 | 12/2004 | Bagaoisan et al. |
| 6,517,553 | B2 | 2/2003 | Klein et al. | 2004/0267308 A1 | 12/2004 | Bagaoisan et al. |
| 6,533,812 | B2 | 3/2003 | Swanson et al. | 2005/0059982 A1 | 3/2005 | Zung et al. |
| 6,551,330 | B1 | 4/2003 | Bain et al. | 2005/0070923 A1 | 3/2005 | McIntosh |
| 6,558,399 | B1 | 5/2003 | Isbell et al. | 2005/0075665 A1 | 4/2005 | Brenzel et al. |
| 6,562,052 | B2 | 5/2003 | Nobles et al. | 2005/0085851 A1 | 4/2005 | Fiehler et al. |
| 6,569,185 | B2 | 5/2003 | Ungs | 2005/0085854 A1 | 4/2005 | Ginn |
| 6,572,629 | B2 | 6/2003 | Kalloo et al. | 2005/0085855 A1 | 4/2005 | Forsberg |
| 6,610,072 | B1 | 8/2003 | Christy et al. | 2005/0121042 A1 | 6/2005 | Belhe et al. |
| 6,623,509 | B2 | 9/2003 | Ginn | 2005/0143761 A1 | 6/2005 | Modesitt |
| 6,623,510 | B2 | 9/2003 | Carley et al. | 2005/0149117 A1 | 7/2005 | Khosravi et al. |
| 6,632,237 | B2 | 10/2003 | Ben-David et al. | 2005/0171561 A1 | 8/2005 | Songer et al. |
| 6,641,592 | B1 | 11/2003 | Sauer et al. | 2005/0177189 A1 | 8/2005 | Ginn et al. |
| 6,663,655 | B2 | 12/2003 | Ginn et al. | 2005/0222614 A1 | 10/2005 | Ginn et al. |
| 6,676,685 | B2 | 1/2004 | Pedros et al. | 2005/0245876 A1 | 11/2005 | Khosravi et al. |
| 6,695,867 | B2 | 2/2004 | Ginn et al. | 2005/0267528 A1 | 12/2005 | Ginn et al. |
| 6,716,228 | B2 | 4/2004 | Tal | 2005/0273137 A1 | 12/2005 | Ginn |
| 6,743,195 | B2 | 6/2004 | Zucker | 2006/0034930 A1 | 2/2006 | Khosravi et al. |
| 6,743,259 | B2 | 6/2004 | Ginn | 2006/0047313 A1 | 3/2006 | Khanna et al. |
| 6,749,621 | B2 | 6/2004 | Pantages et al. | 2006/0079914 A1 | 4/2006 | Modesitt |
| 6,749,622 | B2 | 6/2004 | McGuckin, Jr. et al. | 2006/0100664 A1 | 5/2006 | Pai et al. |
| 6,837,906 | B2 | 1/2005 | Ginn | 2006/0142785 A1 | 6/2006 | Modesitt |
| 6,846,319 | B2 | 1/2005 | Ginn et al. | 2006/0167477 A1 | 7/2006 | Arcia et al. |
| 6,890,343 | B2 | 5/2005 | Ginn et al. | 2006/0173469 A1 | 8/2006 | Klein |
| 6,896,692 | B2 | 5/2005 | Ginn et al. | 2006/0253037 A1 | 11/2006 | Ginn et al. |
| 6,911,034 | B2 | 6/2005 | Nobles et al. | 2006/0253072 A1 | 11/2006 | Pai et al. |
| 6,939,357 | B2 | 9/2005 | Navarro et al. | 2007/0032798 A1 | 2/2007 | Pantages et al. |
| 6,964,668 | B2 | 11/2005 | Modesitt et al. | 2007/0032799 A1 | 2/2007 | Pantages et al. |
| 6,969,397 | B2 | 11/2005 | Ginn | 2007/0032801 A1 | 2/2007 | Pantages et al. |
| 7,001,400 | B1 | 2/2006 | Modesitt et al. | 2007/0049967 A1 | 3/2007 | Sibbitt, Jr. et al. |
| 7,029,480 | B2 | 4/2006 | Klein et al. | 2007/0049968 A1 | 3/2007 | Sibbitt, Jr. et al. |
| 7,029,481 | B1 | 4/2006 | Burdulis, Jr. et al. | 2007/0060895 A1 | 3/2007 | Sibbitt, Jr. et al. |
| 7,048,747 | B2 | 5/2006 | Arcia et al. | 2007/0060950 A1 | 3/2007 | Khosravi et al. |
| 7,063,710 | B2 | 6/2006 | Takamoto et al. | 2007/0112304 A1 | 5/2007 | Voss |
| 7,083,635 | B2 | 8/2006 | Ginn | 2007/0123817 A1 | 5/2007 | Khosravi et al. |
| 7,112,225 | B2 | 9/2006 | Ginn | 2007/0167959 A1 | 7/2007 | Modesitt et al. |
| 7,160,309 | B2 | 1/2007 | Voss | 2007/0203506 A1 | 8/2007 | Sibbitt, Jr. et al. |

| | | | |
|---|---|---|---|
| 2008/0009794 A1 | 1/2008 | Bagaoisan et al. | |
| 2008/0065151 A1 | 3/2008 | Ginn | |
| 2008/0065152 A1 | 3/2008 | Carley | |
| 2008/0287967 A1 | 11/2008 | Andreas et al. | |
| 2009/0005793 A1 | 1/2009 | Pantages et al. | |
| 2009/0048615 A1 | 2/2009 | McIntosh | |
| 2009/0088779 A1 | 4/2009 | Zung et al. | |
| 2009/0157105 A1 | 6/2009 | Zung et al. | |

FOREIGN PATENT DOCUMENTS

| | | |
|---|---|---|
| DE | 4210724 C1 | 7/1993 |
| DE | 9217932 U1 | 7/1993 |
| DE | 4220283 | 12/1993 |
| DE | 10211360 | 10/2003 |
| EP | 0 140 557 | 5/1985 |
| EP | 0 207 545 | 1/1987 |
| EP | 0 474 887 | 3/1992 |
| EP | 0 478 358 | 4/1992 |
| EP | 0 478 887 | 4/1992 |
| EP | 0 589 409 | 9/1992 |
| EP | 0 624 343 | 4/1993 |
| EP | 0 542 126 | 5/1993 |
| EP | 0 568 098 | 11/1993 |
| EP | 0 669 101 | 8/1995 |
| EP | 0 669 102 | 8/1995 |
| EP | 0 669 103 | 8/1995 |
| EP | 684012 A2 | 11/1995 |
| EP | 0 812 571 | 12/1997 |
| EP | 0 941 698 | 9/1999 |
| EP | 0 910 288 | 8/2002 |
| FR | 1059544 | 3/1954 |
| FR | 2768324 | 3/1999 |
| JP | 51143386 | 11/1976 |
| JP | 5220794 | 2/1977 |
| JP | 2119866 | 5/1990 |
| JP | 2119866 A | 5/1990 |
| JP | 542161 A | 2/1993 |
| SU | 820810 | 4/1981 |
| SU | 993922 | 2/1983 |
| SU | 1093329 | 5/1984 |
| SU | 1174036 | 8/1985 |
| SU | 1544383 | 2/1990 |
| SU | 1648400 | 5/1991 |
| WO | WO 85/03858 | 9/1985 |
| WO | WO 94/05213 | 3/1994 |
| WO | WO 94/13211 | 6/1994 |
| WO | WO 94/27503 | 12/1994 |
| WO | WO 94/28801 | 12/1994 |
| WO | WO 95/05121 | 2/1995 |
| WO | WO 95/13021 | 5/1995 |
| WO | WO 95/25468 | 9/1995 |
| WO | WO 95/35065 | 12/1995 |
| WO | WO 96/09006 | 3/1996 |
| WO | WO 97/00046 | 1/1997 |
| WO | WO 97/03613 | 2/1997 |
| WO | WO 97/07745 | 3/1997 |
| WO | WO 97/10764 | 3/1997 |
| WO | WO 97/13461 | 4/1997 |
| WO | WO 97/17901 | 5/1997 |
| WO | WO 97/20505 | 6/1997 |
| WO | WO 97/27897 | 8/1997 |
| WO | WO 98/04195 | 2/1998 |
| WO | WO 98/42262 | 10/1998 |
| WO | WO 99/47049 | 9/1999 |
| WO | WO 00/12013 | 3/2000 |
| WO | WO 00/51498 | 9/2000 |
| WO | WO 00/69342 | 11/2000 |
| WO | WO 01/19259 | 3/2001 |
| WO | WO 01/35833 | 5/2001 |
| WO | WO 02/36021 | 5/2002 |
| WO | WO 02/062234 | 8/2002 |
| WO | WO 03/003925 | 1/2003 |
| WO | WO 03/094748 | 11/2003 |
| WO | WO 03/099134 | 12/2003 |
| WO | WO 2005/000126 | 1/2005 |
| WO | WO 2005/023119 | 3/2005 |
| WO | WO 2005/025430 | 3/2005 |
| WO | WO 2005/030060 | 4/2005 |
| WO | WO 2005/041782 | 5/2005 |
| WO | WO 2005/063129 | 7/2005 |
| WO | WO 2005/065549 | 7/2005 |
| WO | WO 2005/092204 | 10/2005 |
| WO | WO 2005/112782 | 12/2005 |
| WO | WO 2006/026116 | 3/2006 |
| WO | WO 2006/052611 | 5/2006 |
| WO | WO 2006/052612 | 5/2006 |
| WO | WO 2006/078578 | 7/2006 |
| WO | WO 2006/115901 | 11/2006 |
| WO | WO 2006/115904 | 11/2006 |
| WO | WO 2006/118877 | 11/2006 |
| WO | WO 2007/019016 | 2/2007 |
| WO | WO 2007/025014 | 3/2007 |
| WO | WO 2007/025017 | 3/2007 |
| WO | WO 2007/025018 | 3/2007 |
| WO | WO 2007/025019 | 3/2007 |
| WO | WO 2007/081836 | 7/2007 |
| WO | WO 2010/031050 | 3/2010 |

OTHER PUBLICATIONS

U.S. Appl. No. 10/357,984, filed Feb. 4, 2003, Modesett et al.
U.S. Appl. No. 11/891,358, filed Aug. 9, 2007.
U.S. Appl. No. 11/891,513, filed Aug. 9, 2007.
Elgin National Watch Company, Product Borchure entitled "Elgiloy, A Cobalt Nickel Spring Alloy", 33 pages, 1959.
Faulkner, Catherine B., Letter regarding "VasoSeal Vascular Hemostasis", *Datascope*, New Jersey, 1 page, 1991.
Laurus Medical Corporation, "Endoscopic Suturing Made Simple", The Laurus ND-2600 Needle Driver, Irvine, CA. 1 page, 1994.
Marshall, A.C. & Lock, J.E.; "Structural and compliant anatomy of the patient foramen ovale in patients undergoing transcatheter closure", Am. Heart Journal, 140(2):303-307 (2000).
The Laurus In-Line Endoscopic Suturing Device (Oct. 1994) 1 page.
Rema-Medizintcchnik GmbH, Product Brochure entitled "REMA", 7 pages, 1992.
Taber's Cyclopedic Medical Dictionary, $18^{th}$ Ed., p. 747 (1997).
6,136,010, Office Action, mail date Mar. 29, 2000.
6,136,010, Notice of Allowance, mail date May 30, 2000.
6,136,010, Issue Notification, mail date Oct. 6, 2000.
6,964,668, Office Action, mail date Jan. 24, 2005.
6,964,668, Notice of Allowance, mail date May 13, 2005.
6,964,668, Issue Notification, mail date Oct. 26, 2005.
7,001,400, Office Action, mail date Feb. 28, 2003.
7,001,400, Office Action, mail date Nov. 7, 2003.
7,001,400, Notice of Allowance, mail date Apr. 20, 2004.
7,001,400, Issue Notification, mail date Feb. 1, 2006.
7,235,087, Office Action, mail date Aug. 9, 2006.
7,235,087, Notice of Allowance, mail date Feb. 22, 2007.
7,235,087, Issue Notification, mail date Jun. 8, 2007.
2004/00092964, Office Action, mail date Jan. 9, 2006.
2004/00092964, Office Action, mail date Mar. 16, 2006.
2004/00092964, Office Action, mail date Sep. 28, 2006.
2004/00092964, Office Action, mail date Mar. 23, 2007.
2004/0122449, Office Action, mail date Dec. 12, 2006.
2004/0122449, Office Action, mail date Jun. 18, 2007.
2005/0059982, Office Action, mail date Nov. 15, 2005.
2005/0059982, Office Action, mail date Mar. 9, 2006.
2005/0059982, Office Action, mail date Aug. 24, 2006.
2005/0059982, Office Action, mail date Feb. 1, 2007.
2005/0059982, Office Action, mail date Jun. 28, 2007.
2005/0143761, Office Action, mail date Apr. 4, 2007.
2005/0070923, Office Action, mail date Jul. 11, 2007.
2006/0079914, Office Action, mail date Jun. 14, 2007.
2006/142785, Office Action, mail date Jun. 22, 2007.
U.S. Appl. No. 60/506,536, filed Sep. 26, 2003, McIntosh.

U.S. Appl. No. 60/540,811, filed Jan. 30, 2004, McIntosh.
U.S. Appl. No. 60/711,279, filed Aug. 24, 2005, Sibbitt, Jr. et al.
U.S. Appl. No. 12/365,397, filed Feb. 4, 2009, Sibbitt, Jr. et al.
U.S. Appl. No. 12/559,377, filed Sep. 14, 2009, Sibbitt, Jr. et al.
Grossman, William (edited by) Cardiac Catheterization and Angiography, 3rd Ed., Lea & Febiger, Philedelphia 1986.
U.S. Appl. No. 10/335,147, mail date Dec. 13, 2005, Office Action.
U.S. Appl. No. 10/335,147, mail date Apr. 17, 2006, Office Action.
U.S. Appl. No. 10/335,147, mail date Oct. 4, 2006, Notice of Allowance.
U.S. Appl. No. 10/335,147, mail date Dec. 20, 2006, Issue Notification.
U.S. Appl. No. 10/357,984, mail date Nov. 14, 2007, Office Action.
U.S. Appl. No. 10/660,288, mail date Apr. 29, 2009, Office Action.
U.S. Appl. No. 10/660,288, mail date Aug. 3, 2009, Office Action.
U.S. Appl. No. 10/660,288, mail date Mar. 30, 2010, Office Action.
U.S. Appl. No. 11/688,722, mail date Mar. 10, 2010, Office Action.
U.S. Appl. No. 10/729,541, mail date Jan. 8, 2008, Office Action.
U.S. Appl. No. 10/729,541, mail date Sep. 23, 2008, Office Action.
U.S. Appl. No. 10/729,541, mail date May 1, 2009, Office Action.
U.S. Appl. No. 10/729,541, mail date Nov. 16, 2009, Notice of Allowance.
U.S. Appl. No. 10/729,541, mail date Mar. 25, 2010, Notice of Allowance.
U.S. Appl. No. 10/909,531, mail date Dec. 26, 2007, Office Action.
U.S. Appl. No. 10/909,531, mail date Jun. 13, 2008, Office Action.
U.S. Appl. No. 10/909,531, mail date Feb. 9, 2009, Office Action.
U.S. Appl. No. 10/909,531, mail date Sep. 16, 2009, Office Action.
U.S. Appl. No. 11/273,107, mail date Jan. 18, 2008, Office Action.
U.S. Appl. No. 11/273,107, mail date Sep. 5, 2008, Office Action.
U.S. Appl. No. 11/273,107, mail date Apr. 9, 2009, Office Action.
U.S. Appl. No. 11/273,107, mail date Oct. 28, 2009, Office Action.
U.S. Appl. No. 11/316,775, mail date Apr. 16, 2008, Office Action.
U.S. Appl. No. 11/273,107, mail date Aug. 6, 2008, Office Action.
U.S. Appl. No. 11/363,005, mail date Dec. 14, 2007, Office Action.
U.S. Appl. No. 11/363,005, mail date Apr. 17, 2008, Office Action.
U.S. Appl. No. 11/363,005, mail date Dec. 23, 2008, Office Action.
U.S. Appl. No. 11/363,005, mail date Jul. 10, 2009, Notice of Allowance.
U.S. Appl. No. 11/363,005, mail date Jan. 14, 2010, Notice of Allowance.
U.S. Appl. No. 11/508,656, mail date Dec. 9, 2009, Office Action.
U.S. Appl. No. 11/508,656, mail date Mar. 25, 2010, Office Action.
U.S. Appl. No. 11/508,662, mail date Dec. 28, 2009, Office Action.
U.S. Appl. No. 11/508,662, mail date Apr. 14, 2010, Office Action.
U.S. Appl. No. 11/508,715, mail date Jan. 6, 2010, Office Action.
U.S. Appl. No. 11/552,593, mail date Aug. 21, 2008, Office Action.
U.S. Appl. No. 11/552,593, mail date Feb. 5, 2009, Office Action.
U.S. Appl. No. 11/552,593, mail date Oct. 13, 2009, Notice of Allowance.
U.S. Appl. No. 11/552,593, mail date Mar. 22, 2010, Notice of Allowance.
U.S. Appl. No. 90/006,469, mail date Nov. 29, 2002, Request for Re-Examination.
U.S. Appl. No. 90/006,469, mail date Sep. 10, 2004, Re-Examination Office Action.
U.S. Appl. No. 90/006,469, mail date Sep. 27, 2005, Notice of Intent.
U.S. Appl. No. 90/006,469, mail date Jun. 27, 2006, Re-Examination Certification.
U.S. Appl. No. 60/726,985, filed Oct. 14, 2005, Sibbitt, Jr. et al.
U.S. Appl. No. 61/097,072, filed Sep. 15, 2008, Sibbitt, Jr. et al.
5,820,544, Jun. 1974, Semm, (withdrawn).
Cardiac Catheterization and Angiography, 3rd Ed., Lea N ad Febiger, Philadelphia, 1986. Elgiloy Brochure, Jun. 23, 1959, Elgin National Watch Co., Elgin, Il.
Cardio-Thoracic Systems Prospectus dated Mar. 20, 1996.
Datascope Corporation, Montvale, NJ (1991) 1 PG, American Heart Assoc. Meeting, Anaheim.
Elgiloy Brochure, Jun. 23, 1959, Elgin National Watch Co., Elgin, IL.
Nakamura, S. et al., Techniques For Palmaz-Schatz Stent Deployment In Lesions With A Large Side Branch, Catheterization and Cardiovascular Diagnosis, 34: 353-361, 1995.

Serruys, PW et al., A Comparision Of Balloon-Expandable-Stent Implantaion With Balloon Angioplasty In Patients With Coronary Artery Disease, New England Journal of Medicine, 331:489-495, 1994.
U.S. Appl. No. 07/989,611, mail date May 12, 1993, Office Action.
U.S. Appl. No. 07/989,611, mail date Aug. 1, 1994, Office Action.
U.S. Appl. No. 07/989,611, mail date Nov. 3, 1994, Notice of Allowance.
U.S. Appl. No. 08/148,809, mail date Sep. 16, 1994, Office Action.
U.S. Appl. No. 08/148,809, mail date May 30, 1995, Office Action.
U.S. Appl. No. 08/148,809, mail date Oct. 26, 1995, Office Action.
U.S. Appl. No. 08/148,809, mail date Dec. 15, 1995, Notice of Allowance.
U.S. Appl. No. 08/252,124, mail date Jun. 5, 1995, Office Action.
U.S. Appl. No. 08/252,124, mail date Jan. 5, 1996, Office Action.
U.S. Appl. No. 08/252,124, mail date May 22, 1996, Notice of Allowance.
U.S. Appl. No. 08/259,410, mail date Feb. 2, 1995, Office Action.
U.S. Appl. No. 08/259,410, mail date Jun. 1, 1995, Office Action.
U.S. Appl. No. 08/259,410, mail date Feb. 6, 1998, Notice of Allowance.
U.S. Appl. No. 08/638,076, mail date Jan. 21, 1997, Office Action.
U.S. Appl. No. 08/638,076, mail date Oct. 17, 1997, Notice of Allowance.
U.S. Appl. No. 08/824,031, mail date Mar. 16, 1998, Office Action.
U.S. Appl. No. 08/824,031, mail date Sep. 14, 1998, Office Action.
U.S. Appl. No. 08/824,031, mail date Apr. 13, 1999, Office Action.
U.S. Appl. No. 08/824,031, mail date Jul. 15, 1999, Notice of Allowance.
U.S. Appl. No. 08/883,246, mail date Jul. 23, 1998, Office Action.
U.S. Appl. No. 08/883,246, mail date Apr. 12, 1999, Office Action.
U.S. Appl. No. 08/883,246, mail date Oct. 13, 1999, Office Action.
U.S. Appl. No. 08/883,246, mail date Oct. 23, 2000, Office Action.
U.S. Appl. No. 08/883,246, mail date Jul. 11, 2001, Office Action.
U.S. Appl. No. 08/883,246, mail date Sep. 11, 2001, Notice of Allowance.
U.S. Appl. No. 09/057,108, mail date Jul. 10, 2000, Office Action.
U.S. Appl. No. 09/057,108, mail date Oct. 25, 2000, Notice of Allowance.
U.S. Appl. No. 09/395,901, mail date Jun. 27, 2000, Office Action.
U.S. Appl. No. 09/395,901, mail date Nov. 6, 2000, Office Action.
U.S. Appl. No. 09/395,901, mail date Apr. 20, 2001, Notice of Allowance.
U.S. Appl. No. 09/395,901, mail date Sep. 10, 2001, Notice of Allowance.
U.S. Appl. No. 09/610,099, mail date Jul. 11, 2002, Office Action.
U.S. Appl. No. 09/610,099, mail date Dec. 24, 2002, Notice of Allowance.
U.S. Appl. No. 09/707,746, mail date Feb. 16, 2005, Office Action.
U.S. Appl. No. 09/707,746, mail date Jul. 7, 2005, Office Action.
U.S. Appl. No. 09/707,746, mail date Nov. 15, 2005, Notice of Allowance.
U.S. Appl. No. 09/769,109, mail date Oct. 23, 2001, Office Action.
U.S. Appl. No. 09/769,109, mail date Jun. 17, 2002, Office Action.
U.S. Appl. No. 09/769,109, mail date Sep. 9, 2002, Notice of Allowance.
U.S. Appl. No. 09/988,541, mail date Mar. 17, 2004, Office Action.
U.S. Appl. No. 09/988,541, mail date Feb. 28, 2005, Office Action.
U.S. Appl. No. 09/988,541, mail date May 25, 2005, Office Action.
U.S. Appl. No. 09/988,541, mail date Aug. 24, 2005, Office Action.
U.S. Appl. No. 09/988,541, mail date Nov. 8, 2005, Office Action.
U.S. Appl. No. 09/988,541, mail date Dec. 13, 2005, Notice of Allowance.
U.S. Appl. No. 10/033,689, mail date Sep. 30, 2003, Office Action.
U.S. Appl. No. 10/335,065, mail date Mar. 17, 2005, Office Action.
U.S. Appl. No. 10/335,065, mail date Jun. 10, 2005, Office Action.
U.S. Appl. No. 10/335,065, mail date Nov. 17, 2005, Notice of Allowance.
U.S. Appl. No. 10/729,541, mail date Jul. 12, 2010, Notice of Allowance.
U.S. Appl. No. 10/737,668, mail date Nov. 2, 2005, Office Action.
U.S. Appl. No. 10/737,668, mail date Feb. 16, 2006, Office Action.
U.S. Appl. No. 10/737,668, mail date Oct. 19, 2006, Office Action.

U.S. Appl. No. 10/737,668, mail date Jun. 7, 2007, Office Action.
U.S. Appl. No. 10/737,668, mail date Nov. 28, 2007, Office Action.
U.S. Appl. No. 10/737,668, mail date Jun. 26, 2008, Notice of Allowance.
U.S. Appl. No. 10/742,406, mail date Mar. 23, 2007, Office Action.
U.S. Appl. No. 10/742,406, mail date Sep. 10, 2007, Notice of Allowance.
U.S. Appl. No. 10/742,406, mail date Jan. 11, 2008, Notice of Allowance.
U.S. Appl. No. 10/813,449, mail date Sep. 5, 2006, Office Action.
U.S. Appl. No. 10/813,449, mail date Jul. 16, 2007, Office Action.
U.S. Appl. No. 10/813,449, mail date Jan. 25, 2008, Office Action.
U.S. Appl. No. 10/813,449, mail date Aug. 14, 2008, Office Action.
U.S. Appl. No. 10/813,449, mail date Sep. 15, 2008, Office Action.
U.S. Appl. No. 10/813,449, mail date Feb. 3, 2009, Office Action.
U.S. Appl. No. 10/813,449, mail date Aug. 28, 2009, Office Action.
U.S. Appl. No. 10/813,449, mail date May 27, 2010, Office Action.
U.S. Appl. No. 10/909,531, mail date Apr. 29, 2010, Notice of Allowance.
U.S. Appl. No. 11/199,338, mail date Jan. 25, 2007, Office Action.
U.S. Appl. No. 11/199,338, mail date Oct. 5, 2007, Office Action.
U.S. Appl. No. 11/199,338, mail date Dec. 28, 2007, Office Action.
U.S. Appl. No. 11/199,338, mail date Apr. 23, 2008, Office Action.
U.S. Appl. No. 11/199,338, mail date Jan. 6, 2009, Office Action.
U.S. Appl. No. 11/199,496, mail date Apr. 1, 2009, Office Action.
U.S. Appl. No. 11/199,496, mail date Aug. 21, 2009, Office Action.
U.S. Appl. No. 11/199,496, mail date Apr. 23, 2010, Office Action.
U.S. Appl. No. 11/199,515, mail date Aug. 20, 2008, Office Action.
U.S. Appl. No. 11/199,515, mail date Nov. 13, 2008, Office Action.
U.S. Appl. No. 11/199,515, mail date Jun. 10, 2009, Office Action.
U.S. Appl. No. 11/199,515, mail date Dec. 24, 2009, Notice of Allowance.
U.S. Appl. No. 11/199,515, mail date Apr. 2, 2010, Notice of Allowance.
U.S. Appl. No. 11/273,107, mail date Jun. 2, 2010, Office Action.
U.S. Appl. No. 11/389,762, mail date Sep. 20, 2007, Notice of Allowance.
U.S. Appl. No. 11/389,762, mail date Nov. 23, 2007, Notice of Allowance.
U.S. Appl. No. 11/390,937, mail date Sep. 7, 2007, Office Action.
U.S. Appl. No. 11/391,951, mail date Oct. 28, 2008, Office Action.
U.S. Appl. No. 11/391,951, mail date Jan. 30, 2009, Office Action.
U.S. Appl. No. 11/391,951, mail date Aug. 26, 2009, Office Action.
U.S. Appl. No. 11/391,951, mail date Jun. 23, 2010, Office Action.
U.S. Appl. No. 11/508,715, mail date Apr. 26, 2010, Office Action.
U.S. Appl. No. 11/891,358, mail date Apr. 26, 2010, Office Action.
U.S. Appl. No. 11/891,513, mail date Apr. 9, 2010, Office Action.

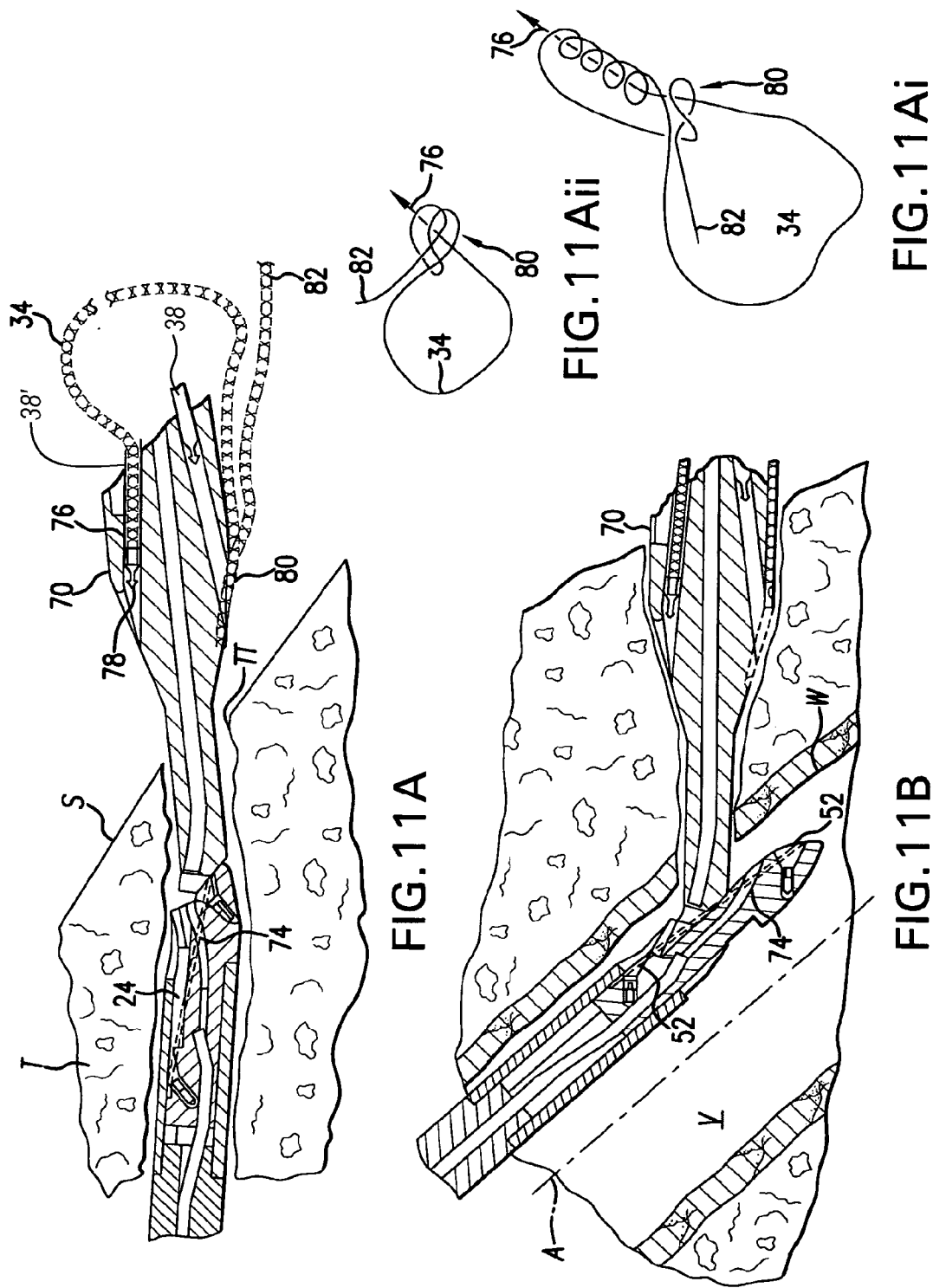

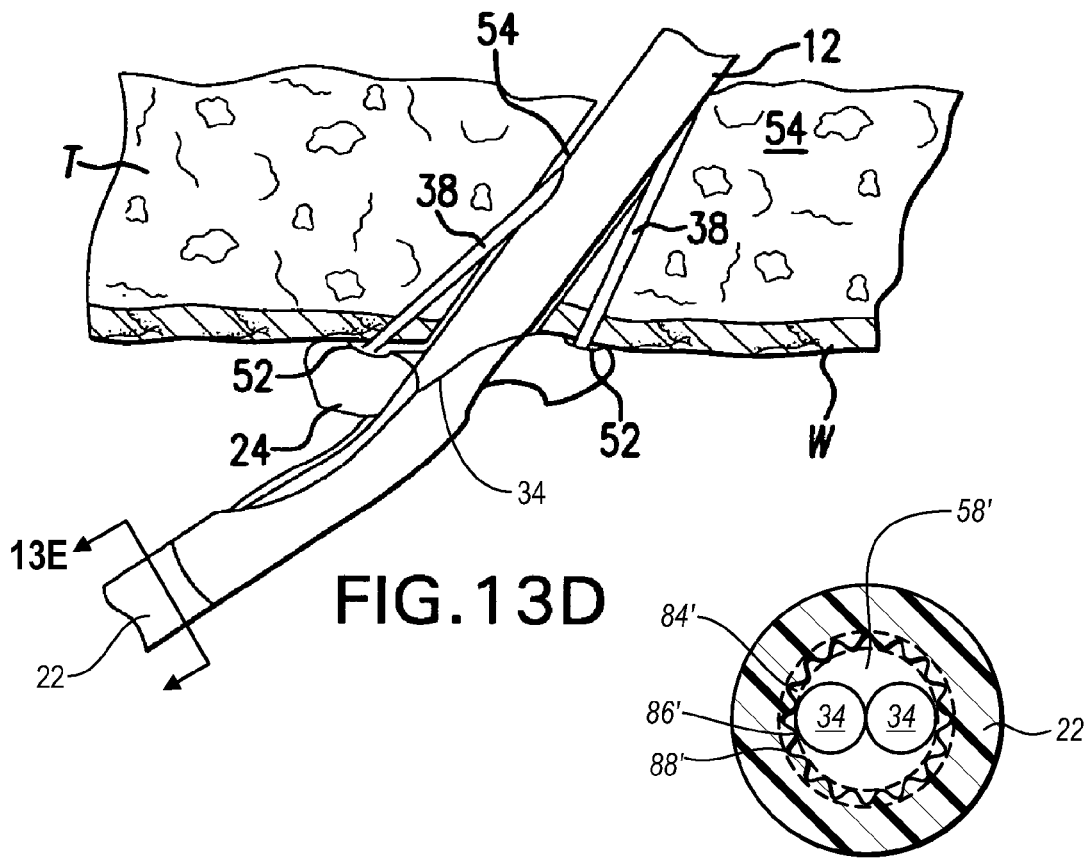
FIG. 13D
FIG. 13E
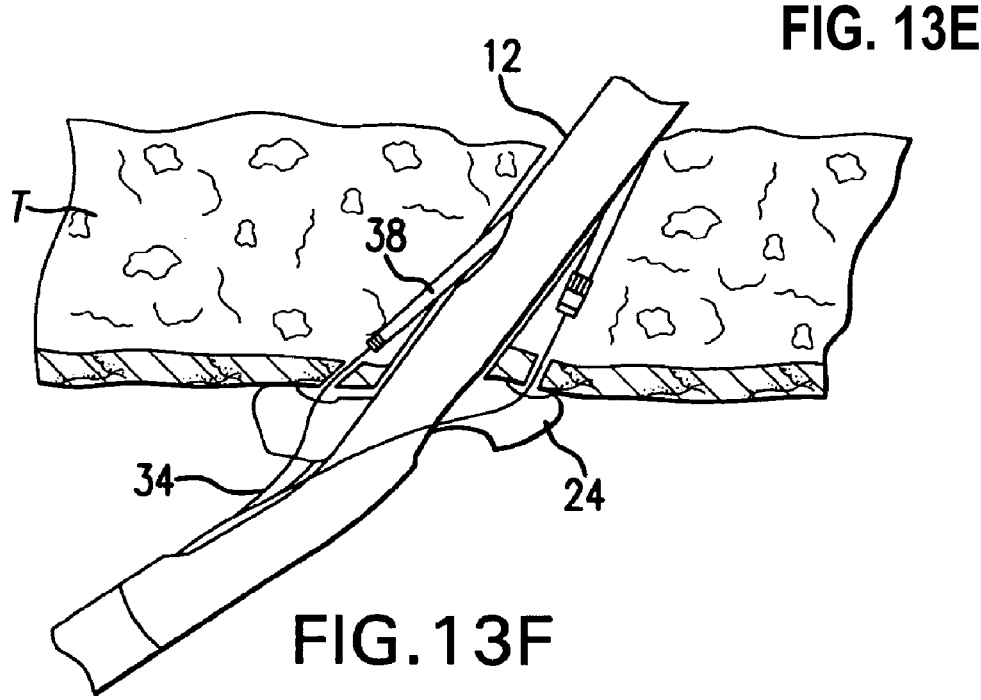
FIG. 13F

ARTICULATING SUTURE DEVICE AND METHOD

CROSS-REFERENCE TO RELATED APPLICATIONS

This application relates to U.S. patent application Ser. No. 10/357,984, filed Feb. 4, 2003, which is a continuation-in-part of U.S. patent application Ser. No. 10/152,272, filed May 20, 2002, now U.S. Pat. No. 6,984,668, which is a continuation-in-part of U.S. patent application Ser. No. 09/651,344, filed Aug. 29, 2000, now U.S. Pat. No. 7,001,400, which is a division of U.S. patent application Ser. No. 09/262,402, filed on Mar. 4, 1999, now U.S. Pat. No. 6,136,010, the disclosures of each is hereby incorporated by reference.

BACKGROUND OF THE INVENTION

1. The Field of the Invention

The present invention relates generally to apparatus and methods for the suturing of body lumens. More particularly, the present invention relates to techniques for percutaneous closure of arterial and venous puncture sites, which are usually accessed through a tissue tract.

2. The Relevant Technology

A number of diagnostic and interventional vascular procedures are now performed translumenally. A catheter is introduced to the vascular system at a convenient access location and guided through the vascular system to a target location using established techniques. Such procedures require vascular access, which is usually established during the well-known Seldinger technique, as described, for example, in William Grossman's "Cardiac Catheterization and Angioplasty," $3^{rd}$ Ed., Lea and Febiger, Philadelphia, 1986, incorporated herein by reference. Vascular access is generally provided through an introducer sheath, which is positioned to extend from outside the patient body into the vascular lumen.

When vascular access is no longer required, the introducer sheath is removed and bleeding at the puncture site stopped. One common approach for providing hemostasis (the cessation of bleeding) is to apply external force near and upstream from the puncture site, typically by manual or "digital" compression. This approach suffers from a number of disadvantages. It is time consuming, frequently requiring one-half hour or more of compression before hemostasis is assured. Additionally, such compression techniques rely on clot formation, which can be delayed until anticoagulants used in vascular therapy procedures (such as for heart attacks, stent deployment, non-optical PTCA results, and the like) wear off. This can take two to four hours, thereby increasing the time required before completion of the compression technique. The compression procedure is further uncomfortable for the patient and frequently requires analgesics to be tolerable. Moreover, the application of excessive pressure can at times totally occlude the underlying blood vessel, resulting in ischemia and/or thrombosis. Following manual compression, the patient typically remains recumbent from four to as much as twelve hours or more under close observation so as to assure continued hemostasis. During this time renewed bleeding may occur, resulting in blood loss through the tract, hematoma and/or pseudo-aneurysm formation, as well as arteriovenous fistula formation. These complications may require blood transfusion and/or surgical intervention.

The incidence of complications from compression-induced hemostasis increases when the size of the introducer sheath grows larger, and/or when the patient is anticoagulated. It is clear that the compression technique for arterial closure can be risky, and is expensive and onerous to the patient. Although the risk of complications can be reduced by using highly trained individuals, dedicating such personnel to this task is both expensive and inefficient. Nonetheless, as the number and efficacy of translumenally performed diagnostic and interventional vascular procedures increases, the number of patients requiring effective hemostasis for a vascular puncture continues to increase.

To overcome the problems associated with manual compression, the use of bioabsorbable fasteners or sealing bodies to stop bleeding has previously been proposed. Generally, these approaches rely on the placement of a thrombogenic and bioabsorbable material, such as collagen, at the superficial arterial wall over the puncture site. While potentially effective, this approach suffers from a number of problems. It can be difficult to properly locate the interface of the overlying tissue and the adventitial surface of the blood vessel. Locating the fastener too far from that interface can result in failure to provide hemostasis, and subsequent hematoma and/or pseudo-aneurysm formation. Conversely, if the sealing body intrudes into the arterial lumen, intravascular clots and/or collagen pieces with thrombus attached can form and embolize downstream, causing vascular occlusion. Also, thrombus formation on the surface of a sealing body protruding into the lumen can cause a stenosis, which can obstruct normal blood flow. Other possible complications include infection, as well as adverse reaction to the collagen or other implant.

A more effective approach for vascular closure has been proposed in U.S. Pat. Nos. 5,417,699, 5,613,974; and PCT published Patent Application No. PCT/US96/10271 filed on Jun. 12, 1996, the full disclosures of which are incorporated herein by reference. A suture-applying device is introduced through the tissue tract with a distal end of the device extending through the vascular puncture. One or more needles in the device are then used to draw suture through the blood vessel wall on opposite sides of the puncture, and the suture is secured directly over the adventitial surface of the blood vessel wall to provide highly reliable closure.

While a significant improvement over the use of manual pressure, clamps, and collagen plugs, certain design criteria have been found to be desirable for successful suturing to achieve vascular closure. For example, it is highly beneficial to properly direct the needles through the blood vessel wall at a significant distance from the puncture so that the suture is well anchored in the tissue and can provide tight closure. It is also highly beneficial to insure that the needle deployment takes place when the device is properly positioned relative to the vessel wall. The ease of deployment and efficacy of the procedure can further be enhanced by reducing the cross-section of that portion of the device, which is inserted into the tissue tract and/or the vessel itself, which may also allow closure of the vessel in a relatively short amount of time without imposing excessive injury to the tissue tract or vessel.

For the above reasons, it would be desirable to provide improved devices, systems, and methods for suturing vascular punctures. The new device should have the capability of delivering a pre-tied knot to an incision site. It would be particularly beneficial if these improved devices provided some or all of the benefits while overcoming one or more of the disadvantages discussed above.

BRIEF SUMMARY OF THE INVENTION

The present invention provides improved devices, systems, and methods for suturing of body lumens. The device often allows the suturing of vascular puncture sites located at the distal end of a percutaneous tissue tract with greater ease, in less time, and with less patient trauma than known systems. Vascular puncture site suturing can be generally provided through the use of shafts having smaller cross-sections than prior suturing systems. In the exemplary embodiment, an elongate articulated foot near a distal end of a shaft can be inserted through the penetration and actuated so that the foot extends along the lumenal axis. The foot can carry suture attachment cuffs, and can be drawn proximally up against the endothelial surface of the blood vessel. Needles can be advanced from the shaft, through the vessel wall beyond the penetration, and into engagement with the needle cuffs. The cross-section of the shaft within the tissue tract can be minimized by laterally deflecting the needles before they leave the shaft, while tapered depressions within the foot can help guide the advancing needles into engagement with the cuffs. The cuffs can lockingly engage the needles so that the cuffs can be withdrawn proximally along the needle paths through the tissue tract so as to form a loop of suture across the puncture without having to thread the needles directly with the suture inside the blood vessel. The suture loop may be drawn distally from the shaft, proximally from within the blood vessel, or laterally down one of the needle paths, across the puncture, and out the opposing path. The interior of the shaft can be configured to aid with releasing the suture loop. More generally, the interior of the shaft can include one or more friction reducing structures or structures that reduce the frictional engagement between the portion of the device forming the slot and the flexible filament.

Regardless, the articulating foot may be realigned with the shaft and withdrawn proximally through the tissue tract in a small profile configuration. The use of an articulatable foot in combination with lateral deflection of the needles can avoid dilation of the tissue tract, as was often necessary using known puncture closure systems.

In one configuration, the invention can provide a method for suturing a puncture through a vessel wall of a blood vessel. The puncture can be disposed within a tissue tract of a patient body, and the method can comprise attaching a flexible filament to a first fitting. The first fitting can be inserted through the tissue tract and positioned adjacent the vessel wall, and a needle path can be formed by advancing a first needle through the vessel wall. The needle can be coupled with the first fitting, and the first needle, the first fitting, and at least a portion of the filament can be withdrawn through the vessel wall along the needle path.

First and second fittings can often be coupled to the flexible filament, and can generally be positioned so that the puncture can be disposed therebetween. The flexible filament can often comprise a suture extending between the first and second fittings, with each fitting being drawn proximally by an associated needle so as to form the suture loop. Alternatively, at least one of the needles may include a detachable tip and may advance a suture distally along the needle path as the needle penetrates through the vessel wall. The flexible filament can again couple the first and second fittings, here allowing both fittings to be withdrawn along a single needle path so that the suture advances down along the first needle path, laterally across the puncture, and then out the other needle path.

Positioning of the fittings can be generally effected by articulating an elongate foot within the blood vessel so that the foot extends along the vessel axis. A confirmation lumen may extend along a shaft supporting the foot to ensure that the foot is positioned within the vessel prior to articulation. Once the foot is properly articulated, it can be withdrawn to firmly engage the endothelial layer of the vessel. The foot can include tapering depressions, which direct the advancing needle toward the fitting, and the suture or other flexible filament adjacent the fittings can be releasably restrained within a narrow slot extending from the depression. This slot can optionally include one or more friction reducing structures or structures that reduce the frictional engagement between the portion of the device forming the slot and the flexible filament.

The suture or other flexible filament and its associated slot can be arranged to avoid entanglement of the advancing needle in the suture, and to ensure that the fitting and suture can be withdrawn proximally as the needle is retracted. An atraumatic, flexible monorail guidebody may extend from the shaft and/or the articulatable foot to facilitate alignment of the foot with the vessel, and also to help provide hemostasis while the knot is tied. A wide variety of foot articulation mechanisms may be provided, with deployment optionally being effected when the foot is disposed entirely within the vessel and using an actuator and foot motion that avoid dilation of the puncture.

In another configuration, the invention can provide a method for suturing an opening in a tissue. The method can comprise inserting a distal end of a device through the opening, the device defining a device axis. An elongated foot of the device can be articulated so that first and second ends of the foot extend laterally with the opening aligned therebetween. A first needle path can be formed from the device, through the tissue, and to the first end of the foot. A second needle path can be formed from the device, through the tissue, and to the second end of the foot. Suture can be advanced along the first and second needle paths to position a suture loop across the opening.

These and other objects and features of the present invention will become more fully apparent from the following description and appended claims, or may be learned by the practice of the invention as set forth hereinafter.

BRIEF DESCRIPTION OF THE DRAWINGS

To further clarify the above and other advantages and features of the present invention, a more particular description of the invention will be rendered by reference to specific embodiments thereof which are illustrated in the appended drawings. It is appreciated that these drawings depict only typical embodiments of the invention and are therefore not to be considered limiting of its scope. The invention will be described and explained with additional specificity and detail through the use of the accompanying drawings in which:

FIGS. 11A-E illustrate an alternative closure system and method for its use in which a first needle advances the suture to the foot, while a second needle engages and withdraws both the first and second suture cuffs, a flexible filament connecting the suture cuffs, and at least a portion of the suture from within the blood vessel so as to complete a pre-tied knot.

FIGS. 13A-H illustrate a method for use of a suture system so as to effect hemostasis of a blood vessel puncture through a tissue tract.

FIGS. 15A through 15F are enlarged cross-sectional views of the embodiment of the suturing device of FIGS. 14A and 14B.

FIGS. 16A and 16B are schematic views of a suture bight having a pre-tied knot in accordance with one embodiment of the present invention.

FIGS. 17A through 17E show enlarged partial cross-sectional views of an embodiment of the suturing device in accordance with the invention, in which one embodiment of a penetrator tip and cuff engagement, penetrator tip disengagement, and cuff ejection sequence is illustrated.

FIG. 18A is an enlarged partial cross-sectional view of an embodiment of a foot in accordance with the present invention, showing the link routing through the suture bearing surfaces of the foot.

FIG. 18B is an enlarged partial cross-sectional view of an embodiment of a device in accordance with the present invention, showing the link routing through a suture-bearing surface located distal to the foot.

FIGS. 19A and 19B are enlarged partial cross-sectional views of an embodiment of a foot in accordance with the present invention, showing an alternate penetrator tip and cuff engagement, penetrator tip disengagement, and cuff ejection sequence.

FIGS. 20A through 20C are enlarged partial cross-sectional views of an embodiment of a foot in accordance with the present invention, showing an alternate penetrator tip and cuff engagement, penetrator tip disengagement, and cuff ejection sequence.

FIG. 21A is an enlarged perspective view of an embodiment of the pre-tied knot in accordance with the present invention.

FIG. 21B is a cross-sectional view of a suture storage tube according to an alternate configuration of the device of FIG. 21A.

FIGS. 22A through 22C show an alternate embodiment of a foot in accordance with the invention.

FIGS. 23A through 23C show another alternate embodiment of a foot in accordance with the invention.

FIGS. 24A and 24B are perspective views of an alternative embodiment of a penetrator tip in accordance with the invention.

FIGS. 25A through 25C are schematic views of an alternate embodiment of a vessel closure device in accordance with the present invention.

FIGS. 26A through 26D are schematic views of alternate embodiments of a vessel closure device in accordance with the invention.

FIG. 27 shows a schematic view of one embodiment of a link and cuff assembly in accordance with the invention.

FIG. 28 shows a bight of suture wrapped on a mandrel to form a pre-tied knot in accordance with the invention.

DETAILED DESCRIPTION

A suturing device, which delivers a pre-tied knot to an incision, is disclosed. As an overview, a suturing device in accordance with the present invention includes a first penetrator having a pre-tied knot disposed thereabout and a second penetrator having suture disposed thereon. During operation of the suturing device, the first penetrator and the second penetrator penetrate the tissue about a periphery of an incision in a body lumen. Upon penetration, a penetrator tip releasably engaged with the first penetrator couples with a foot of the suturing device. As the first and second penetrators retract from the body lumen, the penetrator tip and the suture coupled with the penetrator tip retract through a penetration formed in the body lumen by the first penetrator. As will be discussed in greater detail with reference to the accompanying Figures, as the suture retracts, the pre-tied knot receives the suture, forming a knot for suturing the incision in the body lumen.

Figure 1:
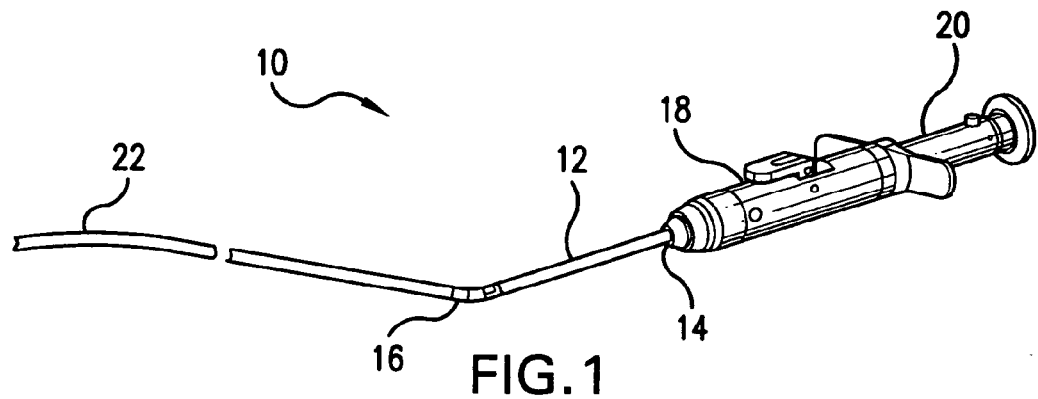
FIG. 1 illustrates a perspective view of a percutaneous blood vessel closure device according the principles of the present invention.

Referring now to FIG. 1, a vessel closure device 10 generally has a shaft 12 having a proximal end 14 and a distal end 16. A proximal housing 18 supports a needle actuation handle 20. A flexible, atraumatic monorail guidebody 22 extends distally of distal end 16 of shaft 12.

Figure 2:
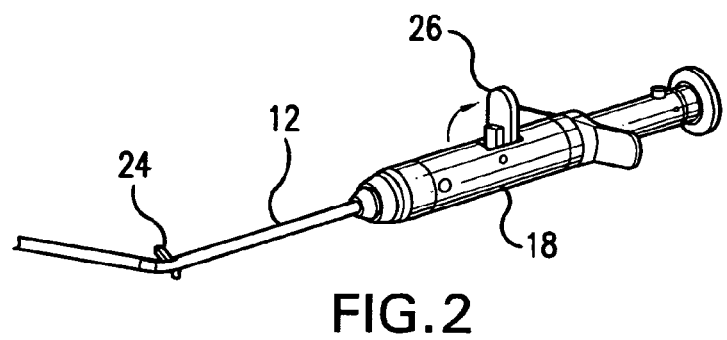
FIG. 2 illustrates the vessel closure device of FIG. 1 in which an elongate foot is shown in a deployed position.

As can be seen with reference to FIG. 2, a foot 24 is articulatably mounted near the distal end of shaft 12. Foot 24 moves between a low profile configuration, in which the foot is substantially aligned along an axis of shaft 12 (as illustrated in FIG. 1), to a deployed position, in which the foot extends laterally from the shaft, upon actuation of a foot actuation handle 26 disposed on proximal housing 18.

Figure 2A:
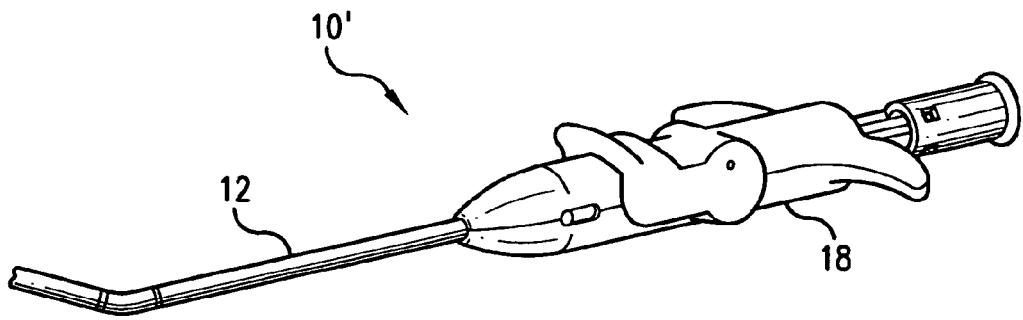
FIGS. 2A-C illustrate actuation of a foot and advancement of needles from a shaft to the articulated foot in a device similar to the device of FIG. 1.
Figure 2B:
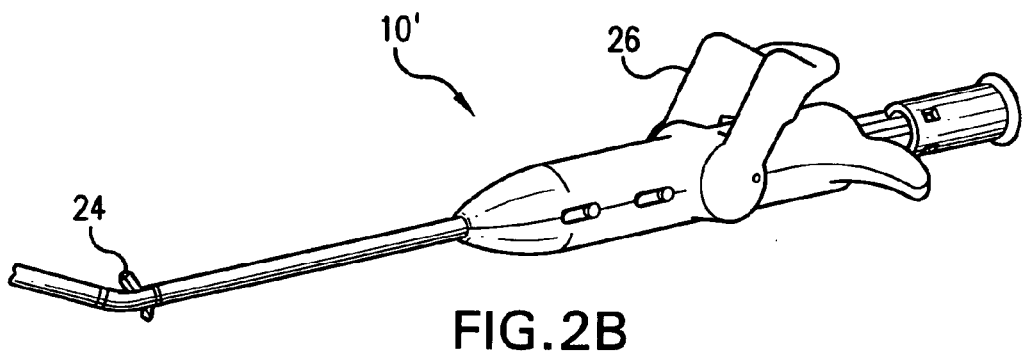
Figure 2C:
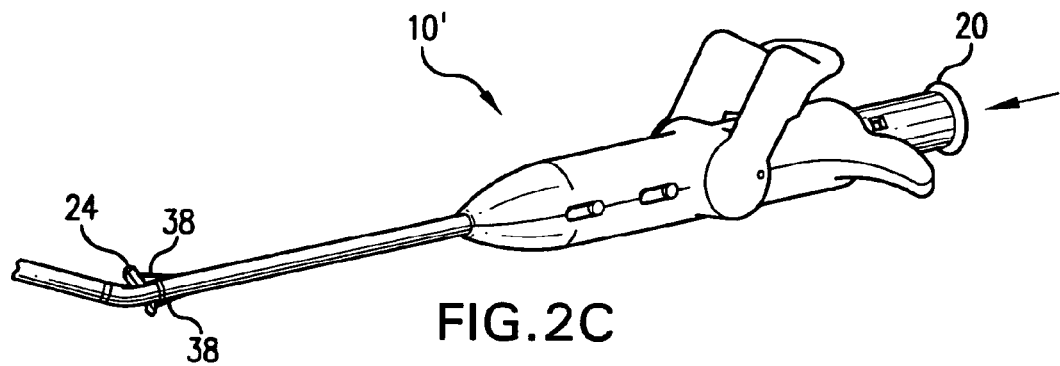

FIGS. 2A through C illustrate the structure and actuation of foot 24 of a device 10' having a modified proximal housing, and also show how needles 38 can be advanced distally from shaft 12 to the foot by depressing needle actuation handle 20. It will be understood that the discussion made with respect to device 10 can also apply to device 10' and other devices described herein, and vice versa.

Figure 3A:
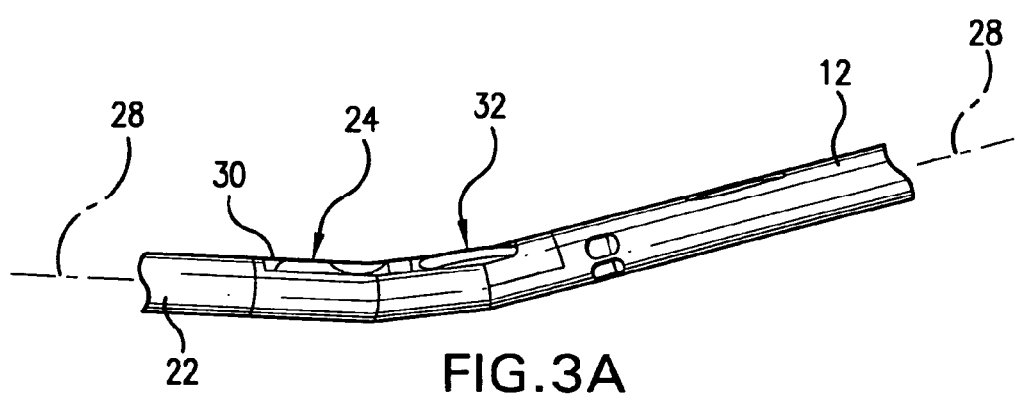
FIG. 3A is a detailed view showing the foot of the vessel closure device of FIG. 1 in a parked position prior to deployment.

Actuation of foot 24 is illustrated more clearly in FIGS. 3A and B. In the parked position illustrated in FIG. 3A, foot 24 extends substantially along axis 28 of shaft 12. Note that the axis of the shaft need not be straight, as the shaft may curve somewhat, particularly adjacent the foot. In the exemplary embodiment, foot 24 is substantially disposed within a foot receptacle 30 of shaft 12 so as to minimize the cross-section of the device adjacent the foot prior to deployment. Advantageously, prior to deployment of the foot, device 10 can have a cross-section adjacent foot 24 of about 7 Fr or less, ideally having a cross-section of about 6 Fr or less for the entire device distally of the proximal end 14 of shaft 12.

Figure 3B:
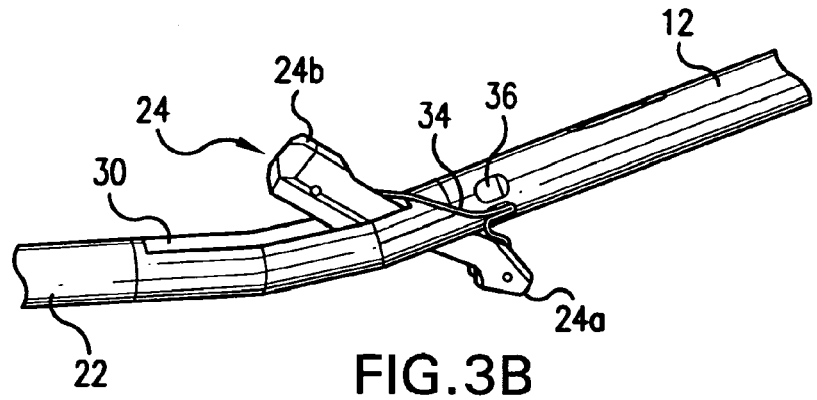
FIG. 3B is a detailed view showing the foot of the vessel closure device of FIG. 1 in a deployed position.

Actuation of foot handle 26 slides a foot actuation wire 32 proximally, pulling foot 24 from a parked position to the deployed position illustrated in FIG. 3B. Once deployed, a first end 24a and a second end 24b of foot 24 extend laterally from the shaft. Suture 34 here comprises a continuous filament with ends disposed in needle receptacles adjacent each end of the foot. An intermediate portion of suture 34 may extend proximally along a suture lumen of shaft 12 to and/or beyond proximal housing 18. Alternatively, in device 10, the length of suture between the ends may extend distally within flexible guidebody 22 in a dedicated lumen (separate from the monorail guidewire lumen). In still further alternatives described below, a short length of suture or some other flexible filament may extend substantially directly between the needle receptacles. Addition information regarding the suture lumen or suture storage structure is provided hereinafter.

Shaft 12 also includes a foot position verification lumen that extends distally from a position verification port 36 to a position indicator at housing 18. When the foot is properly positioned within the blood vessel, blood pressure will cause blood to flow proximally through the indicator lumen to the indicator. The indicator may optionally comprise a blood exit port, a clear receptacle in which blood is visible, or the like. In the exemplary embodiment, the indicator of handle 18 comprises a length of clear tubing extending from housing 18 (not shown) in which the blood is clearly visible. It should be understood that a wide variety of alternative position verifications sensors might be used, including electrical pressure sensors, electrolytic fluid detectors, or the like.

Figure 4:
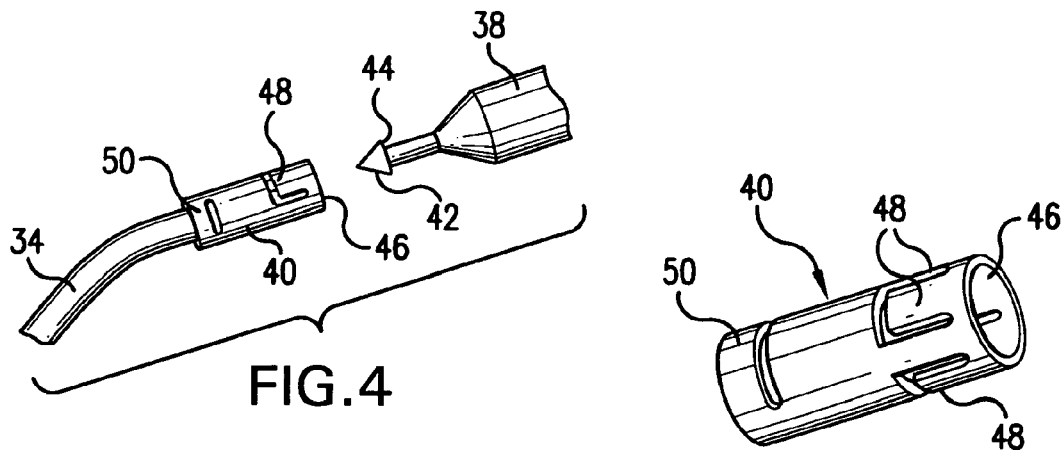
FIGS. 4 and 4A are perspective views illustrating a suture attachment cuff and an associated barbed needle for use in the vessel closure device of FIG. 1.
Figure 4A:
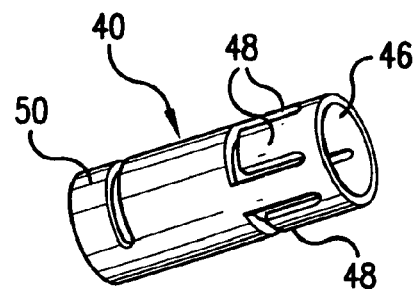
Figure 5:
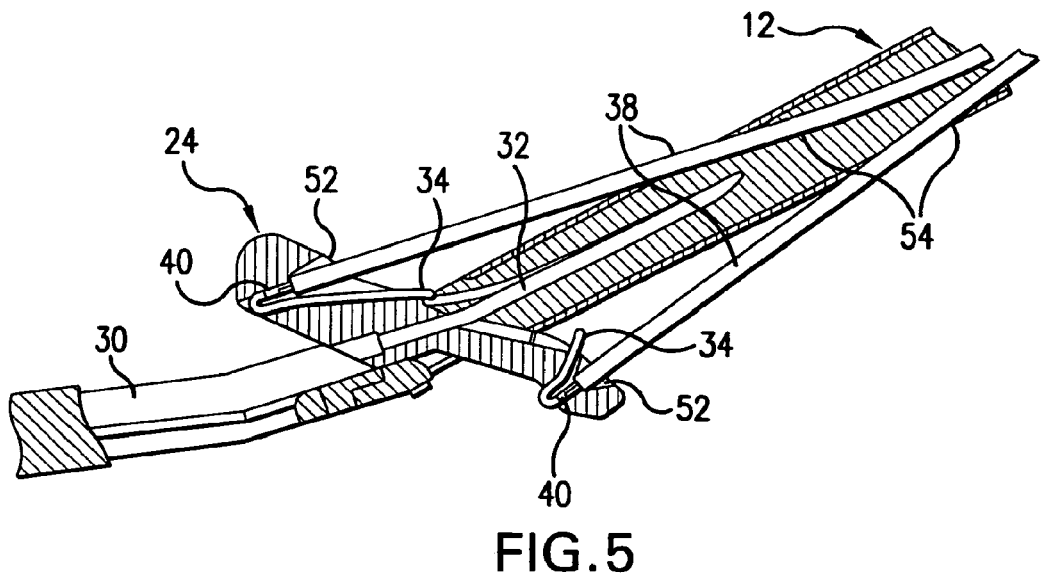
FIG. 5 is a cross-sectional view showing the barbed needles securingly engaging the suture cuffs of the deployed foot.

The structures used in positioning a loop of suture across the puncture can be understood with reference to FIGS. 4, 4A, and 5. In general terms, needles 38 extend from shaft 12 into secured engagement with fittings 40 attached to sutures 34. More specifically, needles 38 include a barbed end 42 defining a recessed engagement surface 44. Fittings 40 are roughly cylindrical structures having an axial channel 46 that receives barbed end 44 of needle 38 therein. A first slot is cut in fitting 44 so as to define at least one tab 48. Tabs 48 can be resiliently biased inward into channel 46. As needle 38 advances into fitting 40, barbed end 42 resiliently displaces tab 48 clear of channel 46 so as to allow the barbed end to pass axially into the fitting. Once barbed end 42 is disposed axially beyond tab 48, the tab 48 resiliently flexes back into the channel, capturing needle 38 by engagement between the tab 48 and recessed surface 44. As each tab 48 can hold the fitting 40 in place on the needle 38, the use of more than one tab increases the reliability of the system. Ideally, three tabs are provided, as illustrated in FIG. 4A.

To facilitate attachment of fitting 40 to suture 34, a second slot cut in the tubular fitting structure defines a suture attachment collar 50. Optionally, collar 50 may be crimped about suture 34 to mechanically affix the suture to fitting 40. In addition and/or instead of mechanical crimping, suture 34 may be bonded to fitting 40 using an adhesive, heat, fasteners, knots, or the like.

Fitting 40 is quite small in size, and is generally configured to facilitate withdrawing the fitting (and the attached suture) along with needle 38 axially through the vessel wall along the needle path. Needle 38 can generally have a cross-sectional width of between about 0.010 inches and 0.020 inches. Barb 42 can extend laterally so as to define an engagement surface 44 having a protruding length of between about 0.002 inches and 0.005 inches. Fitting 40 can have a cross-sectional size roughly corresponding to or only slightly larger than needle 38. Fitting 40 can have an outer lateral width of between about 0.014 inches and 0.025 inches, and an axial length of between about 0.035 inches and 0.050 inches. Channel 46 can be sized to receive at least a portion of needle 38, and can generally have a width of between about 0.010 inches and 0.020 inches. Suture 34 can extend axially opposite the open end of channel 46 so as to minimize drag when the suture is drawn proximally along the needle path. In the exemplary embodiment, needle 38 has a diameter of about 0.020 inches, while the fitting comprises a tube having an outer diameter of about 0.020 inches, an inner diameter of about 0.016 inches, and an overall length of about 0.047 inches. The fitting can comprise a resilient material, optionally comprising a metal, and in the exemplary embodiment, comprising stainless steel.

Needles 38 typically have a length of between about 5.0 inches and 6.0 inches, and can be sufficiently stiff to be advanced in compression through the vessel wall (and adjacent tissues) for up to 0.5 inches when supported in cantilever. Nonetheless, the needles can be flexible enough to be laterally deflected within shaft 12, as can be understood with reference to FIG. 5. Needles 38 generally comprise a high strength metal. In one configuration, the high strength metal comprises stainless steel, although various other metals are possible. Fittings 40 can also comprise a flexible material to allow tab 48 to flex out of the way of barbed end 42, and to resiliently rebound and engage recessed surface 44. In the exemplary embodiment, barbed end 42 has a diameter of about 0.015 inches, with the diameter of the needle decreasing to about 0.008 inches proximally of the barb so as to define the recessed engagement surface.

As was generally described above, foot 24 includes needle receptacles 52 adjacent the ends of the foot. A fitting 40 (with an associated end of suture 34) is disposed within each needle receptacle and a surface of the receptacle tapers proximally and outwardly so as to guide the advancing needles 38 into engagement with fittings 40 when foot 24 is in the deployed position. As fittings 40 (and associated portions of suture 34) are releasably supported in the foot, needles 38 can be withdrawn proximally so as to draw the fittings and suture ends from the foot proximally into (and optionally through) shaft 12. The needle receptacles of the exemplary embodiment taper outward at an angle between 20 and 35 degrees from the centerline of fitting 40, and the fitting is held in a recess having a diameter of about 0.0230 inches and a length of about 0.042 inches. A lateral opening or window through the side of foot to the fitting recess may be provided to facilitate needle and/or cuff positioning during assembly of the device, and a protruding collar near the proximal end of the fitting recess may help keep the fitting in position.

FIG. 5 also illustrates the lateral deflection of needles 38 by needle guides 54 of shaft 12. This lateral deflection of the needles allows the use of a small diameter shaft, while still encompassing sufficient tissue within the suture loop on opposite sides of the puncture so as to effect hemostasis when the suture looped is tightened and secured. In the exemplary embodiment, shaft 12 comprises an outer casing of a biocompatible material such as stainless steel, carbon fiber, nylon, another suitable polymer, or the like. Needle guides 54 may be defined at least in part as lumens formed within the casing of a polymeric material such as nylon or the like. In some embodiments, shaft 12 may comprise a carbon fiber filled nylon, or carbon fiber filled with an alternative material.

Figure 6A:
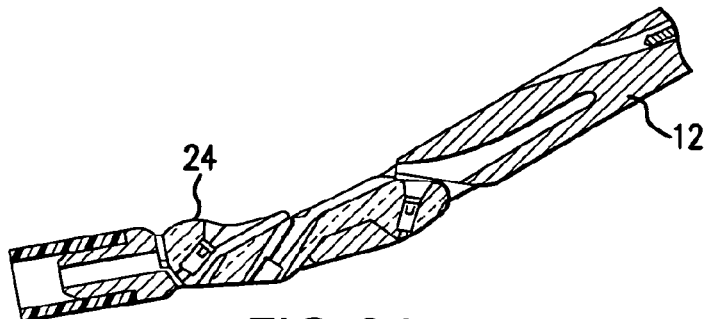
FIGS. 6A-C illustrate one embodiment of a deployable foot, in which the foot slides and pivots when drawn proximally by a tension member.
Figure 6B:
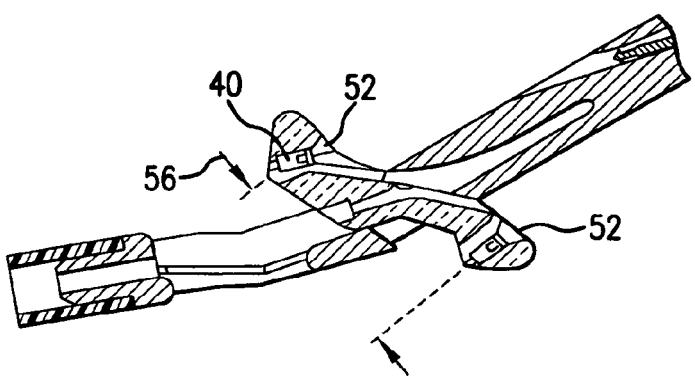
Figure 6C:
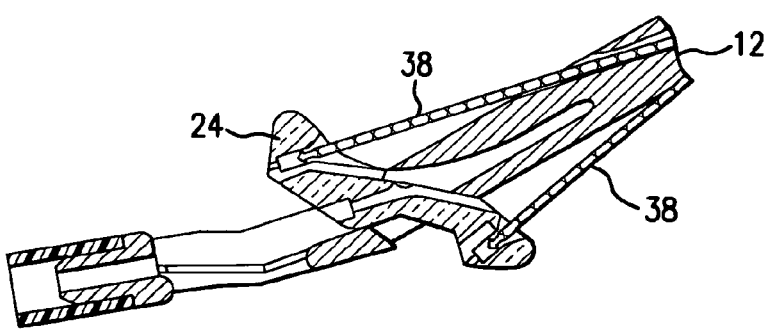

One example of a suitable structure and articulation motion for foot 24 is illustrated in FIGS. 6A and B. Foot actuation wire 32 (see FIG. 3A) rides in a lumen of shaft 12, and draws foot 24 from a parked position (shown in FIG. 6A) to a deployed position (shown in FIG. 6B) through a combination of sliding and pivoting of the foot. The foot remains supported throughout its range of motion by arms disposed laterally on either side of the foot, the arms defining (at least in part) foot receptacle 30. Once foot 24 is deployed, needle receptacles 52 and/or the fittings disposed therein can define lateral suturing width 56 in a range from about 0.260 inches to about 0.300 inches. Foot 24 may be machined or cast from a polymer or metal, but can comprise a polymer such as carbon fiber filled nylon. In some cases, foot 24 may be molded as two separate halves that can subsequently be affixed together. Needles 38 advance from the fixed needle guides 54, and are laterally directed into fittings 40 by receptacles 52, as illustrated in FIG. 6C. In general, a shape memory alloy such as Nitinol® in its superelastic regime provides a particularly advantageous actuator wire for manipulating foot 24.

Figure 7A:
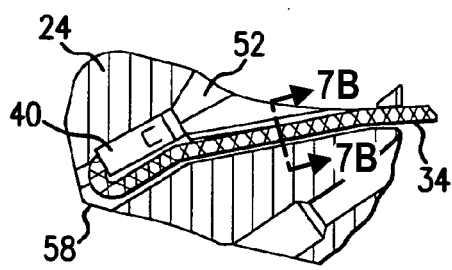
FIGS. 7A-B illustrate the suture cuff positioned within a needle receptacle, the suture being releasably secured within a slot extending radially from the needle receptacle, and friction reducing structures formed in the slot.

Referring now to FIG. 7A, fittings 40 and suture 34 can be withdrawn proximally by the needles from needle receptacles 52. To releasably support fittings 40 and suture 34 and avoid entanglement of the suture in the needles, suture 34 is fittingly received within a slot 58 that extends laterally from needle receptacles 52. As the needles pull the fitting axially from needle receptacles 52, suture 34 is pulled from slot 58 and free from foot 24. Bending of the suture proximally within the suture slot 58 can also locally increase the suture width, so that the interaction between the bent suture and the slot can help hold the fitting in the recess.

Figure 7B:
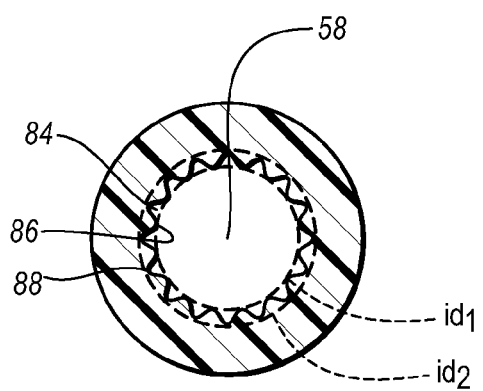

The suture slot 58, or a portion thereof, can be configured to reduce the frictional engagement or contact between the suture and the foot 24. For example, and with reference to FIG. 7B, a portion of the slot 58 can include an interior surface 84 with friction reducing structures. The illustrated interior surface 84 can include at least one raised portion 86 and at least one recessed portion 88, optionally a plurality of raised portions 86 and a plurality of recessed portions 88, which extend longitudinally along the length of the slot 58. The combination of the raised portions 86 and recessed portions 88 reduces the contact surface between the suture 43 (FIG. 7A) and the slot 58 and thereby reduce the frictional forces between the suture 34 and the slot 58 or reduces the suture drag when the suture is moved inside the slot 58. The portions 86 and 88 are one example of a structure capable of performing the function of reducing frictional engagement between a suture and the structure which selectively receives and/or restrains the suture. Other structures can perform this desired function. For instance, and not by way of limitation, the interior surface can include one or more spaced apart raised portion, without recessed portions. For instance, the interior surface can include one or more protrusions that function or act as raised portions. In another configuration, instead of extending longitudinally along the length of the slot or other structure which selectively receives and/or restrains the suture, the structure capable of performing the function of reducing frictional engagement can be (i) helically formed in the interior surface, (ii) formed at some other angular orientation relative to the longitudinal axis of the structure that selectively receives and/or restrains the suture, (iii) formed from a plurality of individual raised and/or recessed portions distributed upon the interior surface, either uniformly or non-uniformly, and/or (iv) combinations of the same.

As illustrated, the raised portions 86 define a first inner diameter $id_1$, while the recessed portions 88 define a second inner diameter $id_2$. In the illustrated configuration, the $id_1$ can be about 0.030 inches, while $id_2$ can any diameter greater than the ids, for instance about 0.040 inches. It will be understood by those skilled in the art that various other configurations are possible. For example, although the raised portions 86 and the recessed portions 88 are generally uniformly distributed on the interior surface 84 in an alternating fashion, irregular distribution of the portions 86 and 88 is possible. Further, although the portions 86 and 88 are generally depicted as being uniform in size, shape, or general configuration, non-uniform size, shape, or configuration of portions 86 and 88 are possible. In addition, the $id_1$ and $id_2$ can be any desired diameter greater or lesser than those identified herein. For instance, and not by way of limitation, $id_1$ can be greater or lesser than 0.030 inches, while $id_2$ can be greater or lesser than 0.040 inches, so long as $id_2$ is greater than $id_1$.

While the above discussion regarding structures to reduce frictional contact is directed to reducing frictional contact between the sutures and the slot of the foot, it will be understood by those skilled in the art that structure similar to those described herein can be used in any portion of the device that may obtain a benefit from reducing the frictional contact with the suture. For instance, and not by way of limitation, portions of the shaft or lumen of the shaft, tubular members disposed within a lumen of the shaft or integrally formed with the shaft, the handle, the guidebody, the foot, or any other portion of the device, or other devices described herein may also include lumens or slots that include friction reducing structures.

Figure 8A:
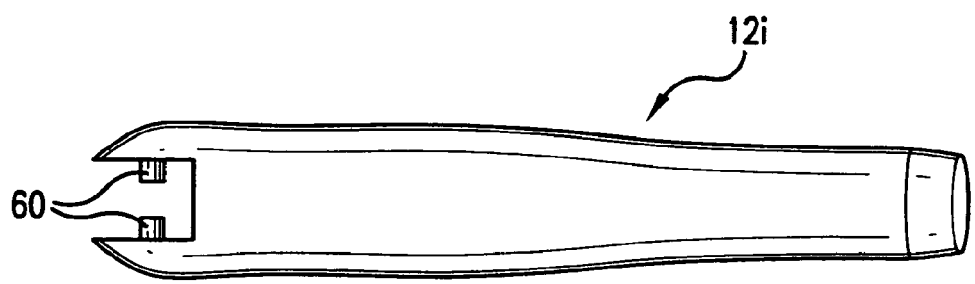
FIGS. 8A-C illustrate an alternative foot articulation mechanism in which lateral slots on the foot receive pins from the shaft to allow the foot to pivot and slide axially.
Figure 8B:
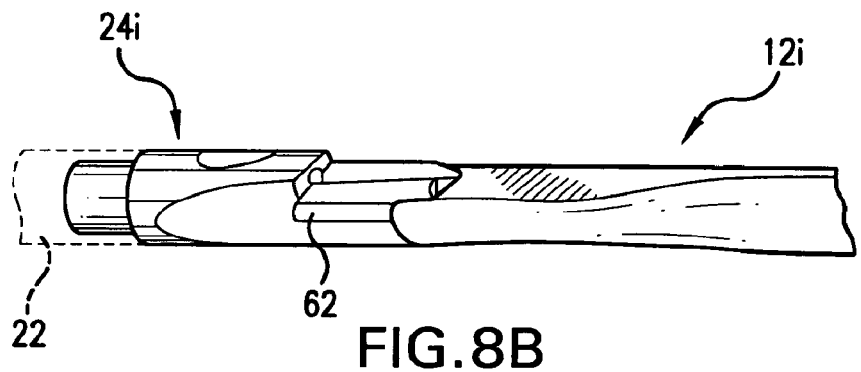
Figure 8C:
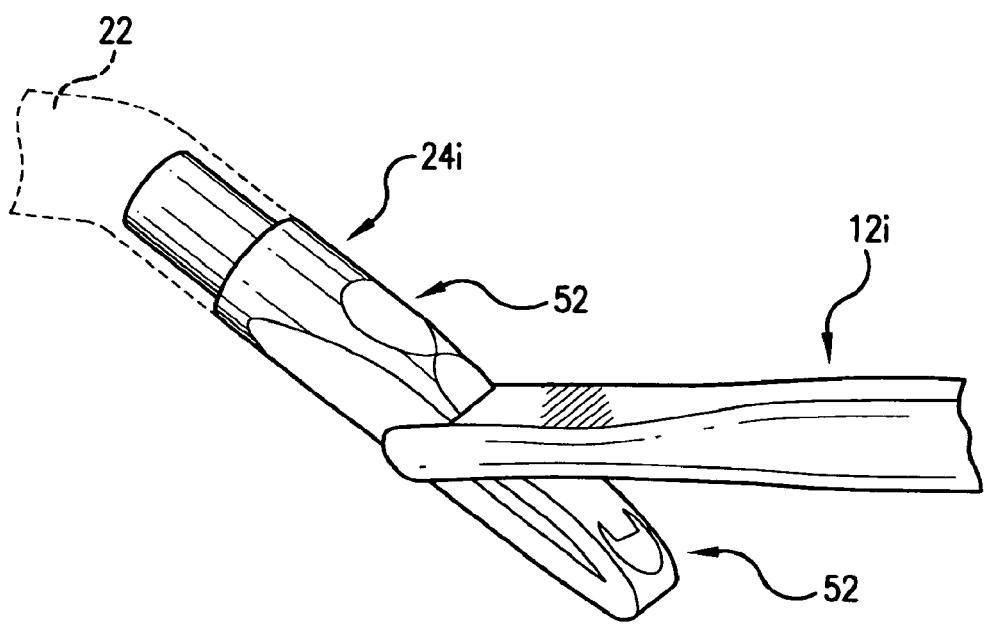

A wide variety of foot actuation mechanisms might be used within the scope of the present invention. A first alternative foot actuation arrangement is illustrated in FIGS. 8A-C. In this embodiment, a shaft 12i has pins 60 which ride in associated slots 62 of a foot 24i. Proximal motion of an actuation wire causes foot 24i to move axially and rotationally, with pins 60 sliding along slot 62, and the foot pivoting about the pins. In this embodiment, guidebody 22 extends directly from the foot, as illustrated in FIG. 8C.

Figure 9A:
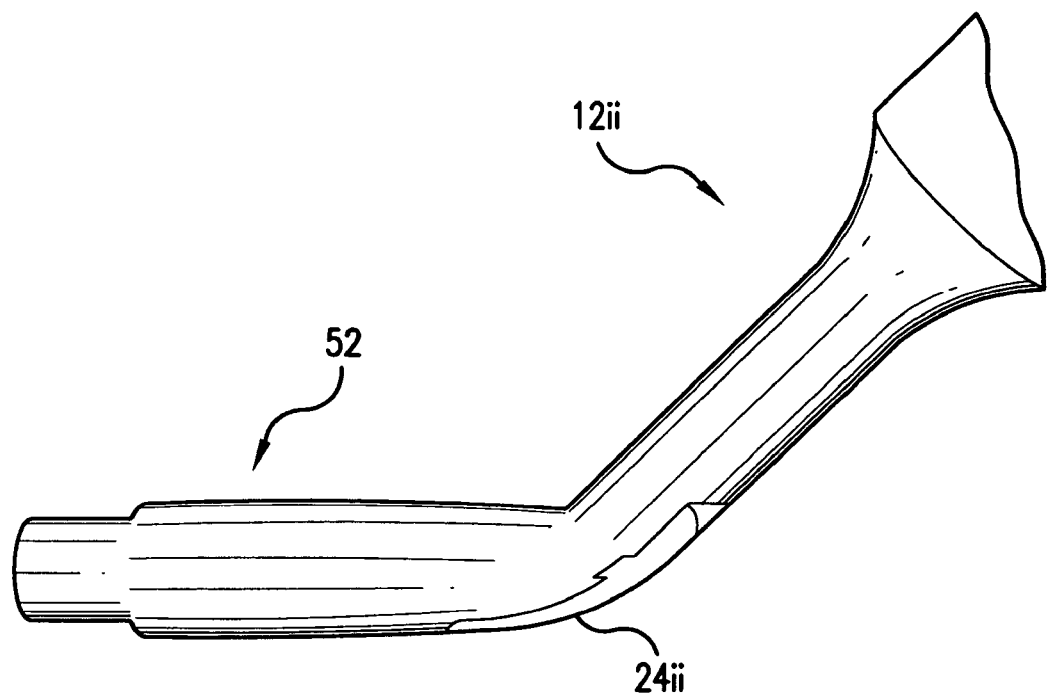
FIGS. 9A and B illustrate a still further alternative foot actuation mechanism in which the foot slides axially within a slot.
Figure 9B:
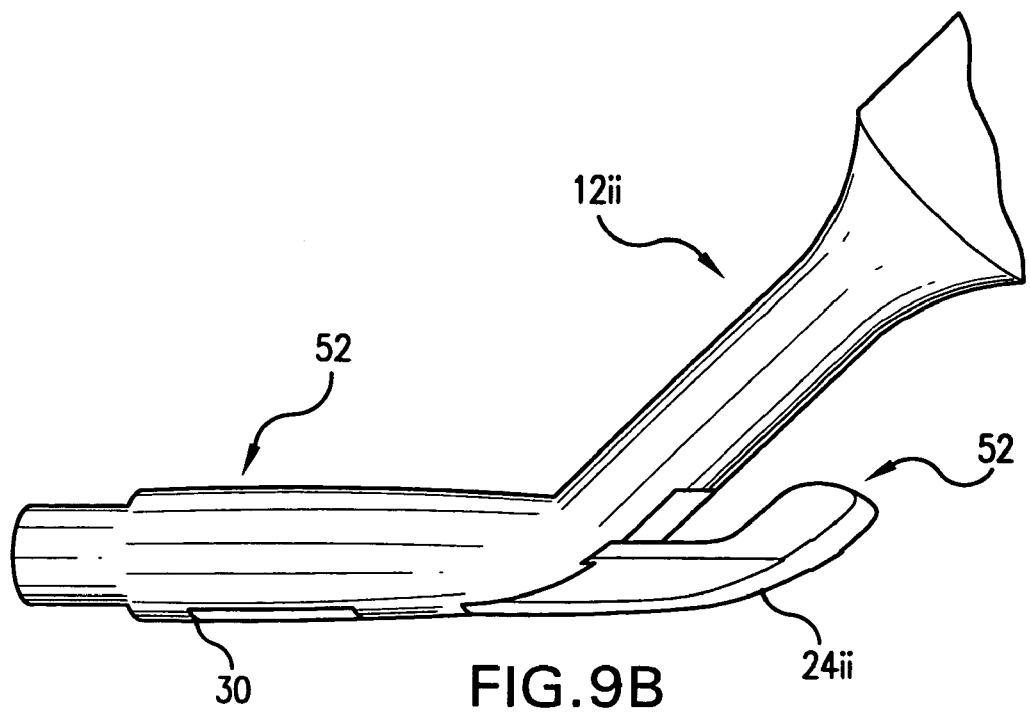
FIGS. 9C and D illustrate a further foot actuation mechanism in which relative movement between the sides of a two-part shaft actuates the foot.

A still further alternative foot actuation mechanism is illustrated in FIGS. 9A and B. In this embodiment, slidable foot 24ii is glidingly received within a receptacle 30 of shaft 12ii. Sliding of the foot 24ii from the parked position of FIG. 9A to the deployed position of FIG. 9B places the needle receptacles 52 in the paths of needles from the shaft 12ii without pivoting of the foot. Guidebody 22 (see FIG. 1) can extend here from a distal end of shaft 12ii at a fixed angle from the shaft. Optionally, insertion through the tissue tract may be facilitated by including an additional bend in the shaft axis adjacent the guidebody on many embodiments.

Figure 9C:
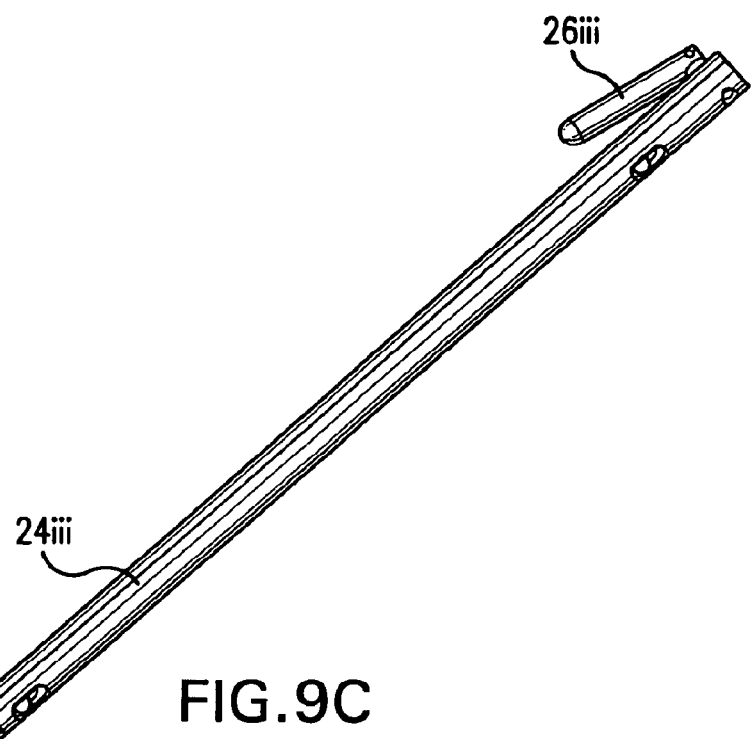
Figure 9D:
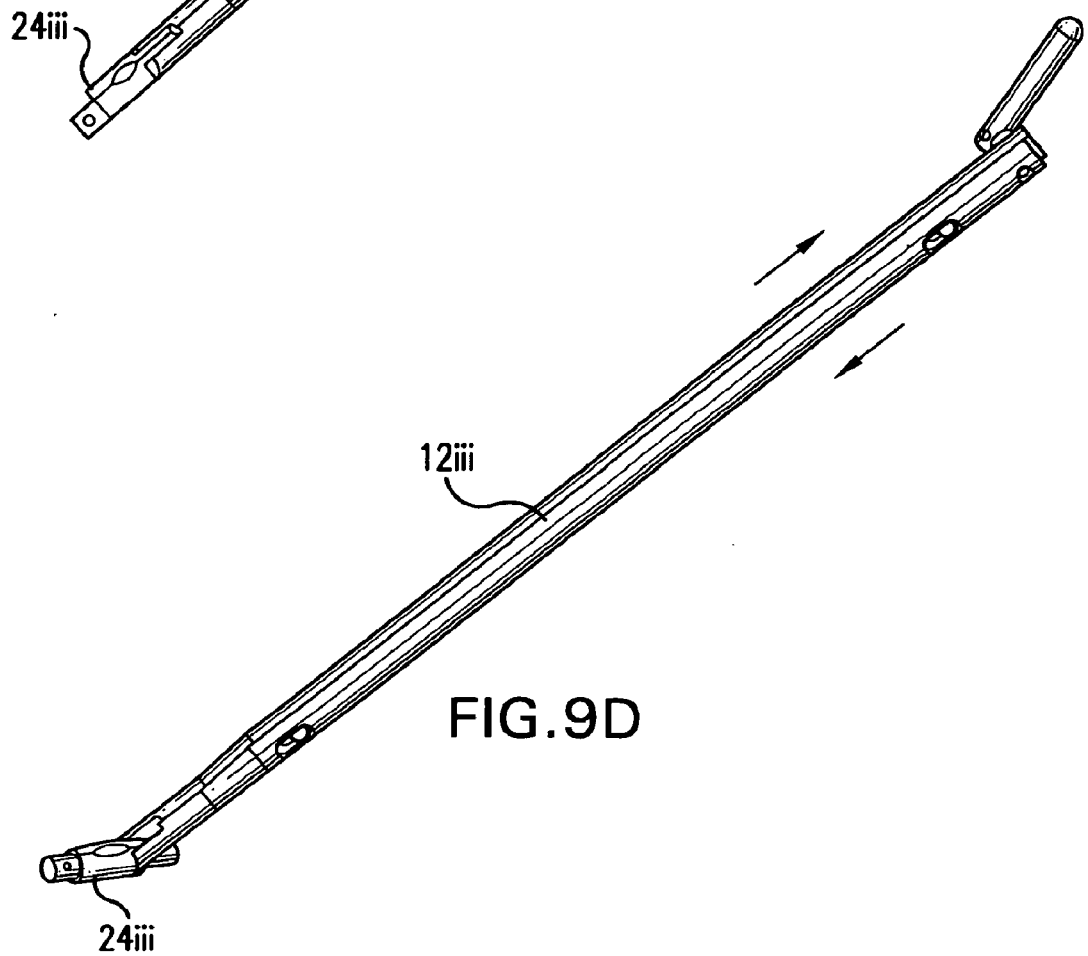

Yet another foot actuation mechanism can be understood with reference to FIGS. 9C and D. Shaft 12iii is formed in two parts, which slide axially relative to each other when foot actuation lever 26iii moves, using an offset crank arrangement. A similar offset crank supports foot 24iii, so that the sliding shaft parts cause the foot to pivot as shown.

Figure 10A:
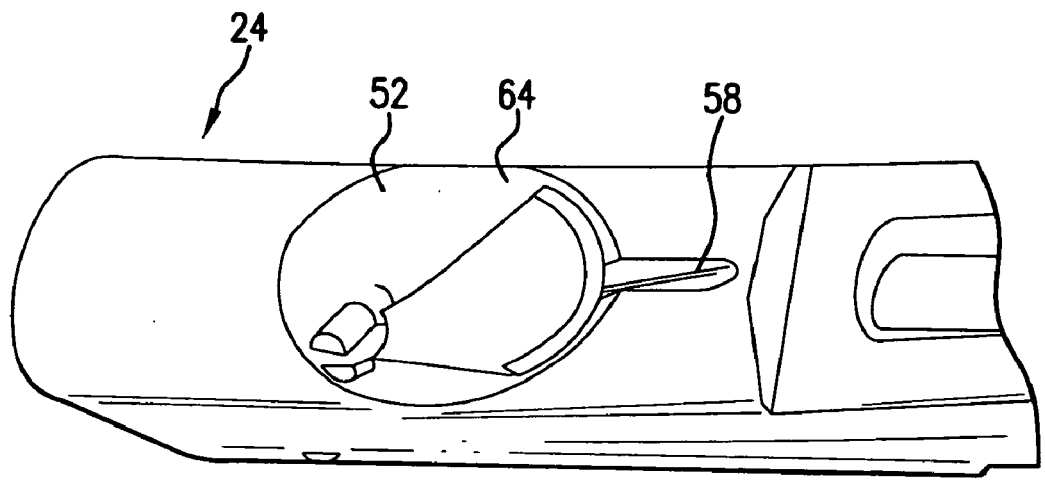
FIGS. 10A-D illustrate alternative structures and techniques for avoiding entanglement of the needle with the suture.

A variety of features may be included in the articulatable foot, the needle receptacle, and/or the needle to avoid tangling of the needle in the suture as the needle is directed to the fitting. As illustrated in FIG. 10A, a moveable flap 64 may extend over slot 58 so that the advancing needle slides along the flap toward the fitting, rather than entering the slot and engaging the suture directly. Flap 64 may be affixed along one side of the slot, with the other side of the flap flexing into the receptacle to release the suture from slot 58 when the fitting and suture are withdrawn by the needle.

Figure 10B:
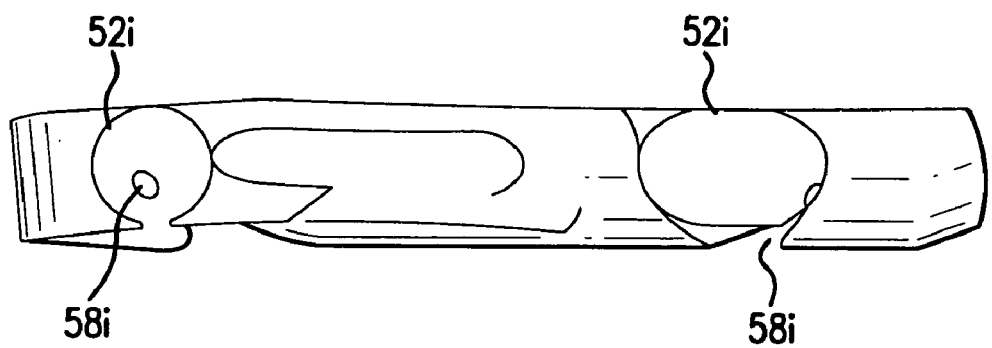

An alternative mechanism for avoiding entanglement of the needle with the suture is illustrated in FIG. 10B. In this embodiment, needle receptacles 52i have tangential slots 58i which extends substantially tangentially to the surface of the receptacle. As a result of this tangential arrangement, a needle entering the receptacle 52i will be directed toward the fitting contained therein, but will generally not be able to enter and advance within the tangential slot 58i so as to become entangled with the suture. As illustrated in this embodiment, the slots may optionally extend laterally through the foot so that the loop of suture can be pulled from one side of the shaft without interference. Interference can also be prevent or substantially reduced by forming friction reducing structures within the interior of the shaft. These friction reducing structures can be similar to those described with respect to FIGS. 7A and 7B.

Figure 10C:
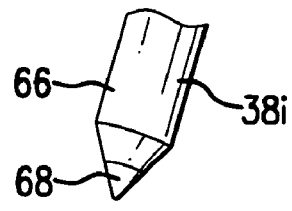
Figure 10D:
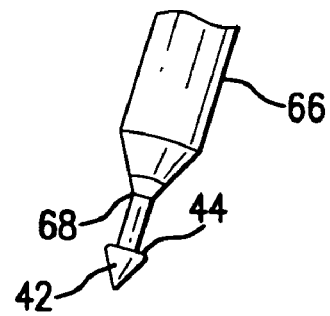

A still further alternative mechanism for avoiding entanglement between the suture and the needle is illustrated in FIGS. 10C and D. Two-part needle 38i includes an outer sheath 66 and an inner core 68. The parts of these needles initially advance together into the receptacles with the needle core 68 withdrawn so that the needle presents a smooth tapered tip (the combined tip preferably being larger in diameter than the slot containing the suture) as illustrated in FIG. 10C. Once two-part needle 38i is fully positioned within the needle receptacle, needle core 68 may extend axially to expose barbed tip 42 and recessed engagement surface 44 and to secure the needle to the fitting within the needle receptacle. In the exemplary embodiment of FIGS. 4 and 5, barbed tip 42 is formed integrally with the rest of the needle structure, but the tip has a larger cross-section than radial slot 58 containing the suture 34. As a result, the barbed tip is unable to enter the slot, thereby avoiding entanglement between the needle and suture.

An alternative vessel closure device 70 will be explained with reference to FIGS. 11A through 11E. This embodiment includes an articulatable foot 24 having a pair of needle receptacles 52, as described above. Although each needle receptacle 52 contains a fitting 40 for coupling a flexible filament to a tip of an associated needle, the filament in this case comprises a short length of suture 74 (or some temporary connecting filament, as shown schematically in phantom in FIG. 11A) spanning directly between the needle receptacles. Rather than pulling the two ends of an extended loop through the needle paths and proximally out the tissue tract for tying, closure system 70 advances a single end of the suture distally along one needle path, across the puncture, and then proximally along the other needle path. To provide this interaction, at least one needle includes means for attaching suture 34 to short suture 74, here in the form of a detachable coupling structure carried on the at least one needle. This structure facilitates the use of a pre-tied knot.

Referring now to FIGS. 11A and B the distal end of device 70 advances distally through skin S and into a tissue T of the patient while the device is in the small profile configuration with foot 24 aligned along the axis of the device. Here, however, an end 76 of suture 34 is affixed to a detachable needle tip 78 of a hollow needle 38'. Detachable tip 78 comprises a fitting having an opening receiving an end of suture similar to fitting 40, attached to a barbed needle end (similar to that of needle 38). Suture 34 may extend proximally within hollow needle 38' where the needle has an open channel along its length, may exit the hollow needle 38' just proximally of detachable tip 78, or may be disposed alongside a solid needle. Needle 38 (opposite hollow needle 38') has a fixed barbed tip, as described above, and a bight of suture 80 is releasably attached to the device shaft encircling the opening of needle guide 54 of the fixed tip needle 38. The bight of suture may be releasably disposed within a slot of the device, may be temporarily held in place by a weak adhesive or coating, or the like. A second end 82 of suture 34 extends proximally along the shaft of the device, the second end of the suture optionally also being releasably held along the shaft.

Bight 80 can define a knot when first end suture passes therethrough, as can be understood with reference to FIGS. 11Ai and 11Aii. Bight 80 can often include more than one loop, and may be pre-arranged so as to define a square knot (using the layout schematically illustrated in FIG. 11Ai), a clinch knot (FIG. 11Aii), or a variety of known or new surgical knots.

Device 70 advances along tissue tract TT to puncture P in blood vessel V. Once foot 24 is disposed within a blood vessel V, a pull wire moves the foot proximally and pivots the foot laterally so that the foot extends along an axis A of the vessel, as illustrated in FIG. 11B. The foot can then be pulled proximally against an inner surface of the vessel wall W to ensure that the needle receptacles 52 are properly positioned.

Figure 11C:
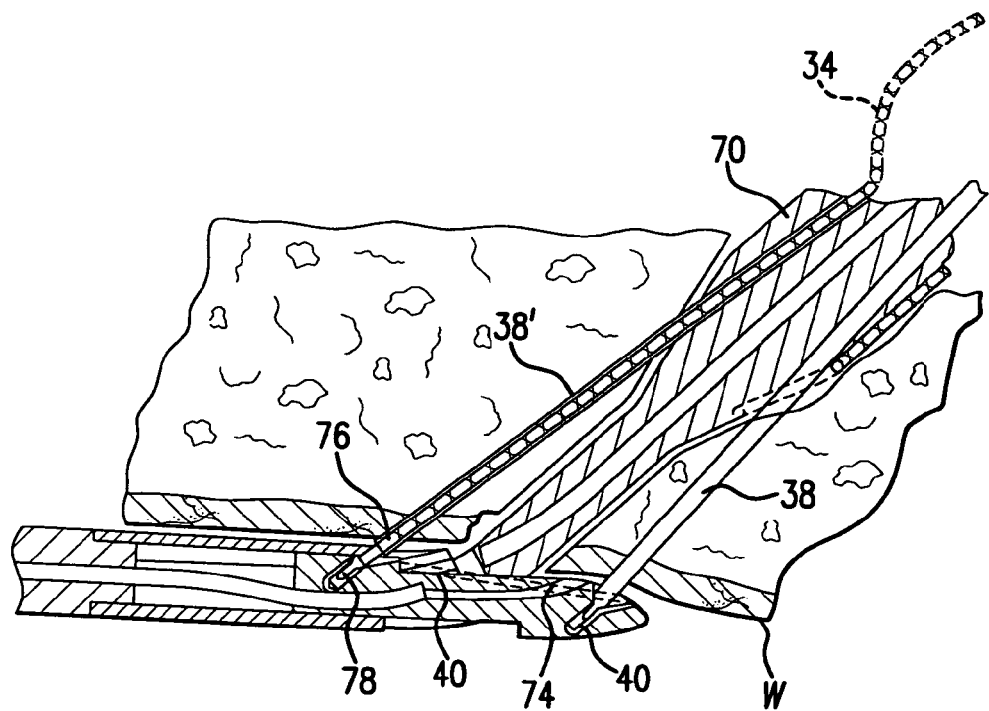

As can be understood with reference to FIGS. 11C and D, hollow needle 38' and needle 38 advance to engage fittings 40 within receptacles 52. Hollow needle 38' draws first end 76 of suture 34 distally through vessel wall W, and detachable tip 78 is secured into an associated fitting 40 using the barb and tab interaction described above. As short suture 74 extends between fittings 40, and as detachable tip 78 can pull free of hollow needle 38' when the needles are withdrawn, this effectively couples needle 38 to first end 76 of suture 34. The detachable tip riding partially within the hollow needle (or vice versa) so that the assembly remains together under compression. Hence, needle 38 can pull the suture distally along the needle path formed by hollow needle 38', across the puncture P, and proximally along the needle path formed by needle 38, as illustrated in FIG. 11D.

Figure 11D:
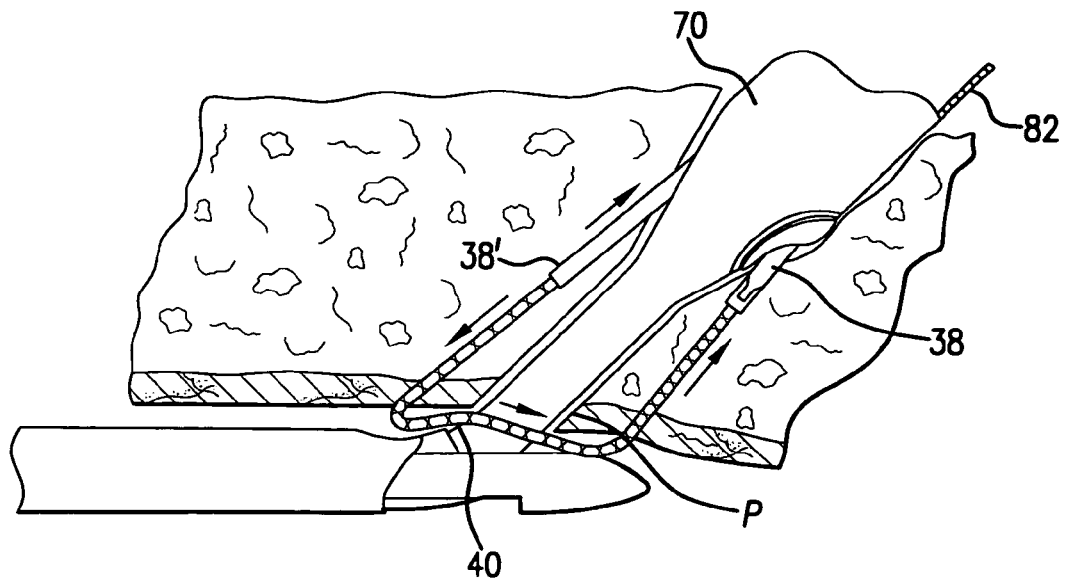
Figure 11E:
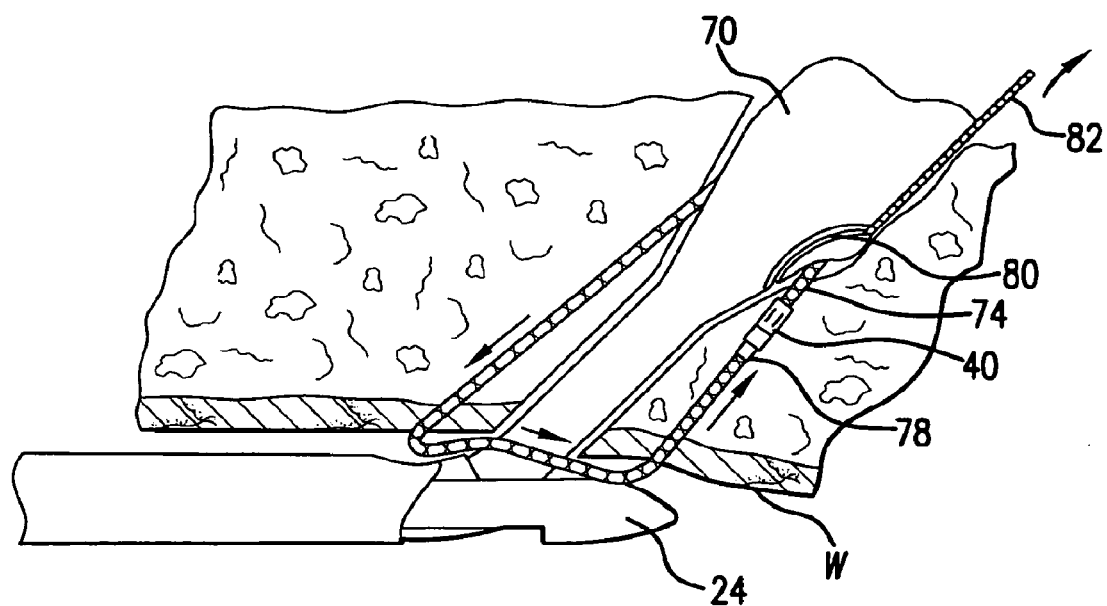

FIGS. 11D and E show that the knot can be completed by pulling needle 38, short suture 74, and second end 76 of suture 34 (together with the fittings 40 and detachable needle tip 78) proximally through bight 80. Second end 82 of suture 34 can be pulled to free bight 80, and the ends of the suture can be tightened and the device removed to provide permanent hemostasis.

It will be recognized that removal of device 70 can be facilitated by coupling first end 76 to bight 80 over an outer surface of the device, and by arranging suture 34 and hollow needle 38' so that the suture can pull free of the needle when detachable tip 78 is released, for example, by having the suture exit the needle proximally of the tip through a channel that extends to the tip so that the needle does not encircle the suture. By including such provisions, after foot 24 is returned to the narrow configuration, the device can be pulled proximally from the tissue tract leaving the pre-tied knot in place.

Alternative arrangements (using the detachable needle ends of device 70) are possible to provide the benefit of a pre-tied knot and the like for closure of a vessel puncture. For example, a device having a pair of needles in which each needle included a detachable tip might be used to pull first end 76 through a bight, so that the bight need not encircle the needle path of one of the needles.

It will be understood that hollow needle 38' can be modified to aid with the slidable engagement of the suture with the interior of the lumen of the hollow needle 38'. For instance, and not by way of limitation, the lumen of hollow need 38', or other portion of the suture path, can include friction reducing structures as described in FIGS. 7A and 7B. The hollow needle lumen, therefore, can include one or more raised portions and/or one or more recessed portions that reduce the contact surface between the suture and the wall or surface of the lumen, slot, or other structure receiving the suture.

Figure 12A:
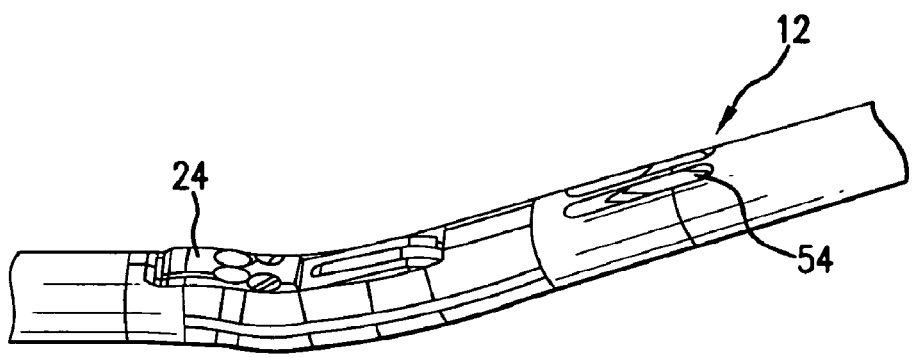
FIGS. 12A and B illustrate an alternative device having two pairs of needles and a foot with four needle receptacles so as to form two loops of suture across a puncture of a blood vessel.
Figure 12B:
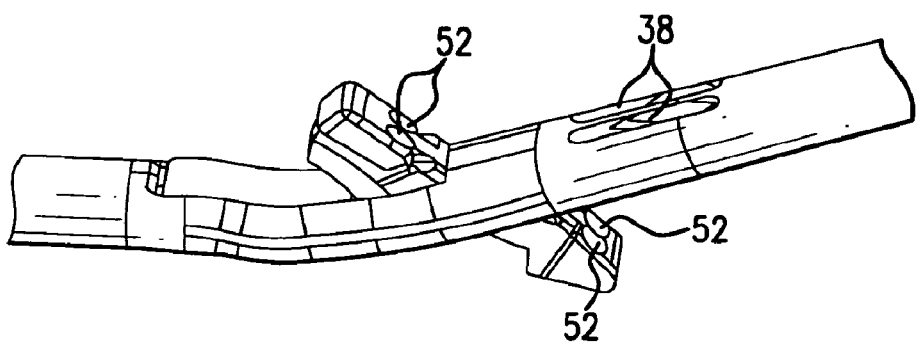

In some cases, particularly for closure of large punctures, it may be advantageous to provide multiple suture loops across the puncture, either in parallel, in an "X" pattern, or the like. As illustrated in FIGS. 12A and B, the present invention encompasses the use of more than two needles and associated receptacles, fittings, sutures, and the like. Multiple loop systems may have four, six, eight, or more needles, or may even have odd numbers of needles and fittings, particularly where one or more fittings have a plurality of suture ends extending therefrom. This allows a wide variety of stitching patterns to be provided by such multiple loop devices.

Figure 13A:
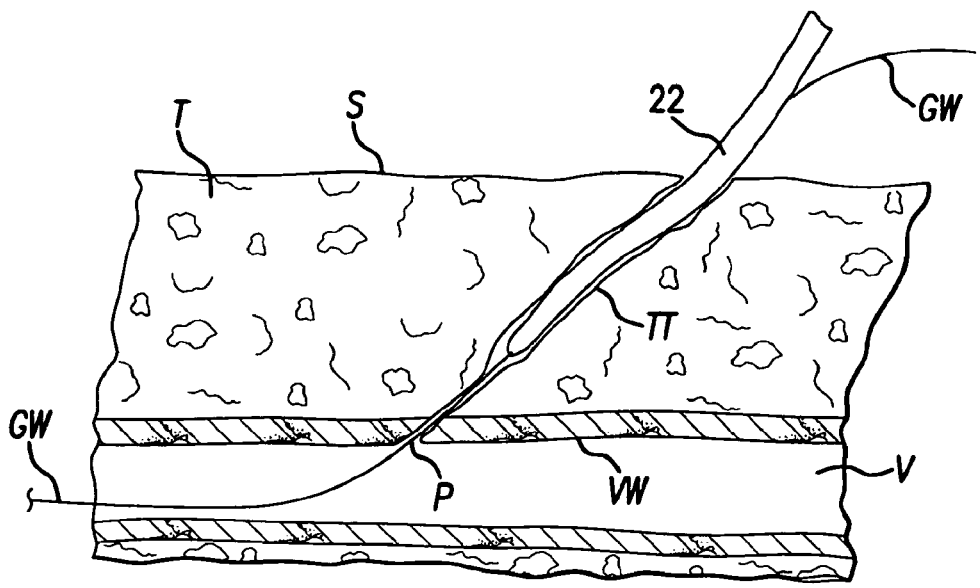
Figure 13B:
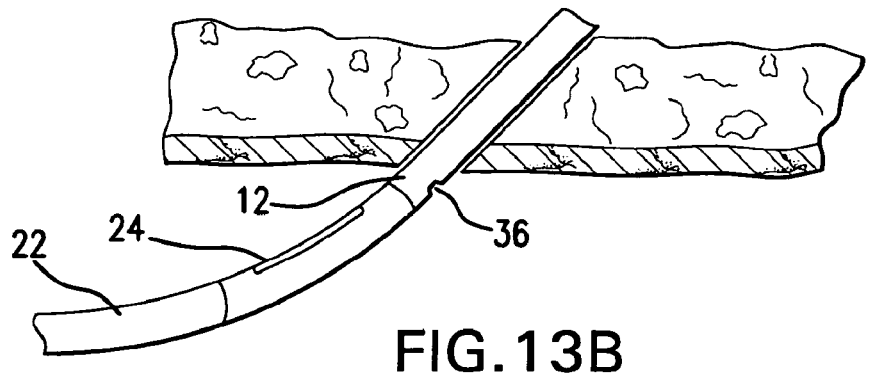

The method of use of the devices of FIGS. 1-7 can be understood with reference to FIGS. 13A-G. After accessing a blood vessel V (often using the Seldinger technique), a guidewire GW is left extending into skin S and down through tissue T along tissue tract TT. Guidewire GW enters vessel V through a puncture P in vessel wall W, and extends along the vessel throughout many endovascular procedures. As illustrated in FIG. 13A, distal guidebody 22 is advanced over the guidewire GW in a monorail fashion, so that the guidewire helps to direct the device along the tissue tract TT and into the vessel through puncture P. FIG. 13B shows that when sensor 36 is disposed within the vessel, blood can flow from the sensor port and through a lumen in shaft 12 to the proximal handle to notify the operator that foot 24 has been advanced far enough for deployment.

Figure 13C:
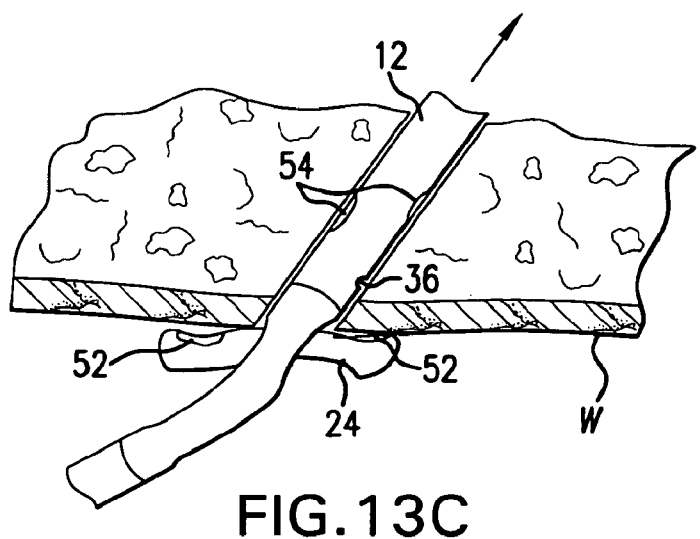
Figure 13G:
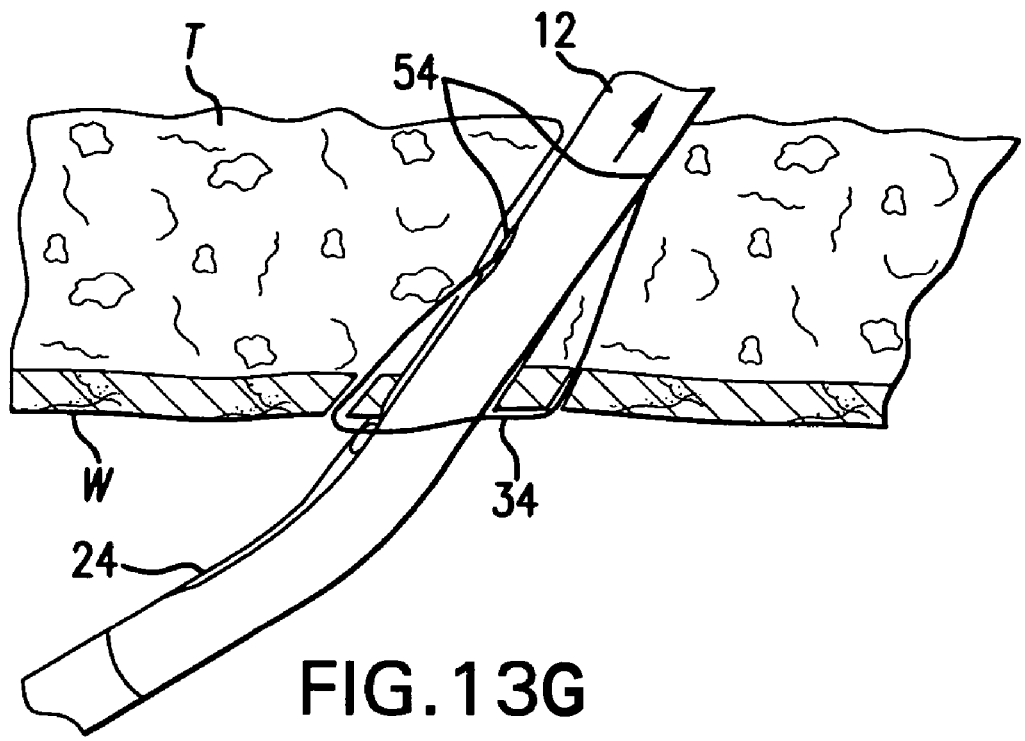

Deployment of the foot is effected by actuation of the foot deployment handle, as described and illustrated above with reference to FIGS. 2 and 2B. As described above, guidebody 22 helps to align the device with the axis of vessel V. Guidebody 22 may be set at an angle and/or offset relative to shaft 12 as appropriate to aid in alignment with a particular vessel access technique. As shown in FIG. 13C, the deployed foot 24 extends laterally from the shaft, so that foot 24 adjacent receptacles 52 can be drawn up against vessel wall W by gently pulling shaft 12. Hence, the foot helps to accurately position the needle guides 54 at a distance from the vessel wall.

Referring now to FIG. 13D, flexible needles 38 are deflected laterally by needle guides 54 toward receptacles 52 of the deployed foot. As a result, the needles advance in cantilever both distally and laterally when needle actuation handle 20 is pressed (see FIG. 2C), and the tapering surfaces of receptacles 52 help to push the needles back into alignment with the fittings so as to overcome any unintended deflection of the needles by tissue T or vessel wall W. This ensures that needles 38 securingly engage fittings 40 within receptacles 52, thereby coupling the ends of suture 34 to the needles. While suture 34 is here illustrated running along the side of shaft 12 outside foot receptacle 30 to a lumen within guidebody 22, it should be understood that the suture loop might instead extend proximally in a lumen of shaft 12, might be routed through the foot and/or foot receptacle, and/or might be stored in a spool adjacent foot 24. Regardless, suture 34 should able to pull free of the device between its ends to form a continuous loop across puncture P.

To facilitate easy removal from within the guidebody 22 or a lumen of the shaft 12, friction reducing structures can be formed within guidebody 22 or the lumen of shaft 12. Exemplary structures are illustrated in FIG. 13E. As illustrated, a portion of the lumen 58' of guidebody 22 can include an interior surface 84' with friction reducing structures. The illustrated interior surface 84' can include at least one raised portion 86' and at least one recessed portion 88', optionally a plurality of raised portions 86' and a plurality of recessed portions 88', which extend longitudinally along the length of the lumen 58'. The combination of the raised portions 86' and recessed portions 88' reduces the contact surface between the suture 34 and the lumen 58' and thereby reduce the frictional forces between the suture 34 and the lumen 58' or reduces the suture drag when the suture is moved inside the lumen 58'. The portions 86' and are one example of a structure capable of performing the function of reducing frictional engagement between a suture and the structure which selectively receives and/or restrains the suture. Other structures can perform this desired function. For instance, and not by way of limitation, the interior surface can include one or more spaced apart raised portion, without recessed portions. For instance, the interior surface can include one or more protrusions that function or act as raised portions. In another configuration, instead of extending longitudinally along the length of the lumen or other structure which selectively receives and/or restrains the suture, the structure capable of performing the function of reducing frictional engagement can be (i) helically formed in the interior surface, (ii) formed at some other angular orientation relative to the longitudinal axis of the structure that selectively receives and/or restrains the suture, (iii) formed from a plurality of individual raised and/or recessed portions distributed upon the interior surface, either uniformly or non-uniformly, and/or (iv) combinations of the same.

It will be understood by those skilled in the art that various other configurations of the friction reducing structures are possible. For example, although the raised portions 86' and the recessed portions 88' are generally uniformly distributed on the interior surface 84' in an alternating fashion, irregular distribution of the portions 86' and 88' is possible. Further, although the portions 86' and 88' are generally depicted as being uniform in size, shape, or general configuration, non-uniform size, shape, or configuration of portions 86' and 88' are possible.

While the above discussion regarding structures to reduce frictional contact is directed to reducing frictional contact between the sutures and the slot of the foot, it will be understood by those skilled in the art that structure similar to those described herein can be used in any portion of the device that may obtain a benefit from reducing the frictional contact with the suture. For instance, and not by way of limitation, portions of the shaft or lumen of the shaft, tubular members disposed within a lumen of the shaft or integrally formed with the shaft, the handle, the guidebody, the foot, or any other portion of the device, or other devices described herein may also include lumens or slots that include friction reducing structures.

Referring now to FIGS. 13F and G, fittings 40 and the ends of suture 34 are drawn proximally through the vessel wall W along the needle paths formed by needles 38. Optionally, the needles may be withdrawn proximally out of the tissue tract and clear of shaft 12, or they may remain coupled to the shaft within needle guides 54. The foot actuator is moved to store foot 24 along shaft 12, and the shaft can then be pulled proximally from the tissue tract. Guidebody 22, which may comprise a soft, compliant polymer, may temporarily extend at least partially into tissue tract TT and through puncture P to help reduce the loss of blood until the loop is secured.

Figure 13H:
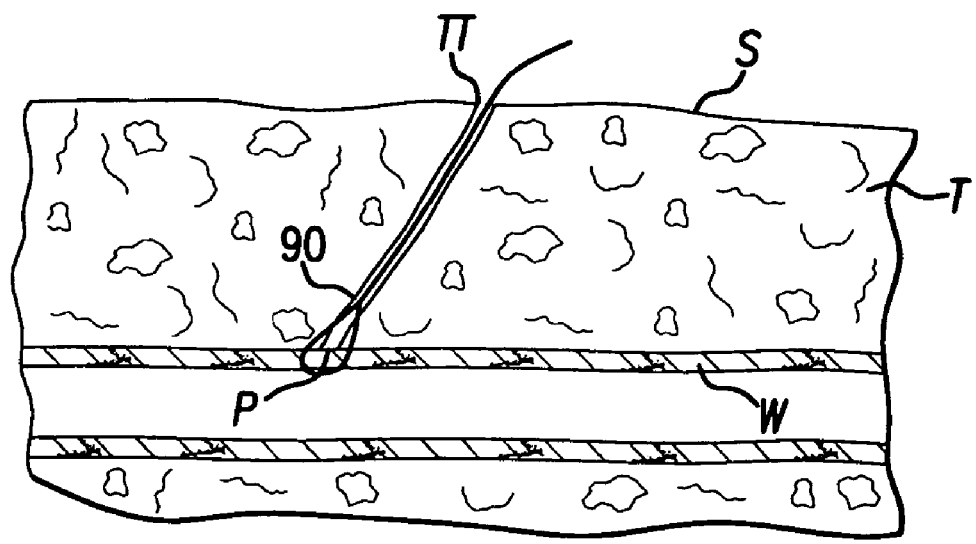

Now referring to FIG. 13H, once shaft 12 has been withdrawn sufficiently to expose needle guides 54, the ends of the suture loop can be grasped by the operator. Tying of a knot in suture 34 can then proceed in a conventional manner. The use of a clinch knot may facilitate gradual tightening of the knot while removing guidebody 22, although a wide variety of knot and knot advancing techniques might be used.

Figure 14A:
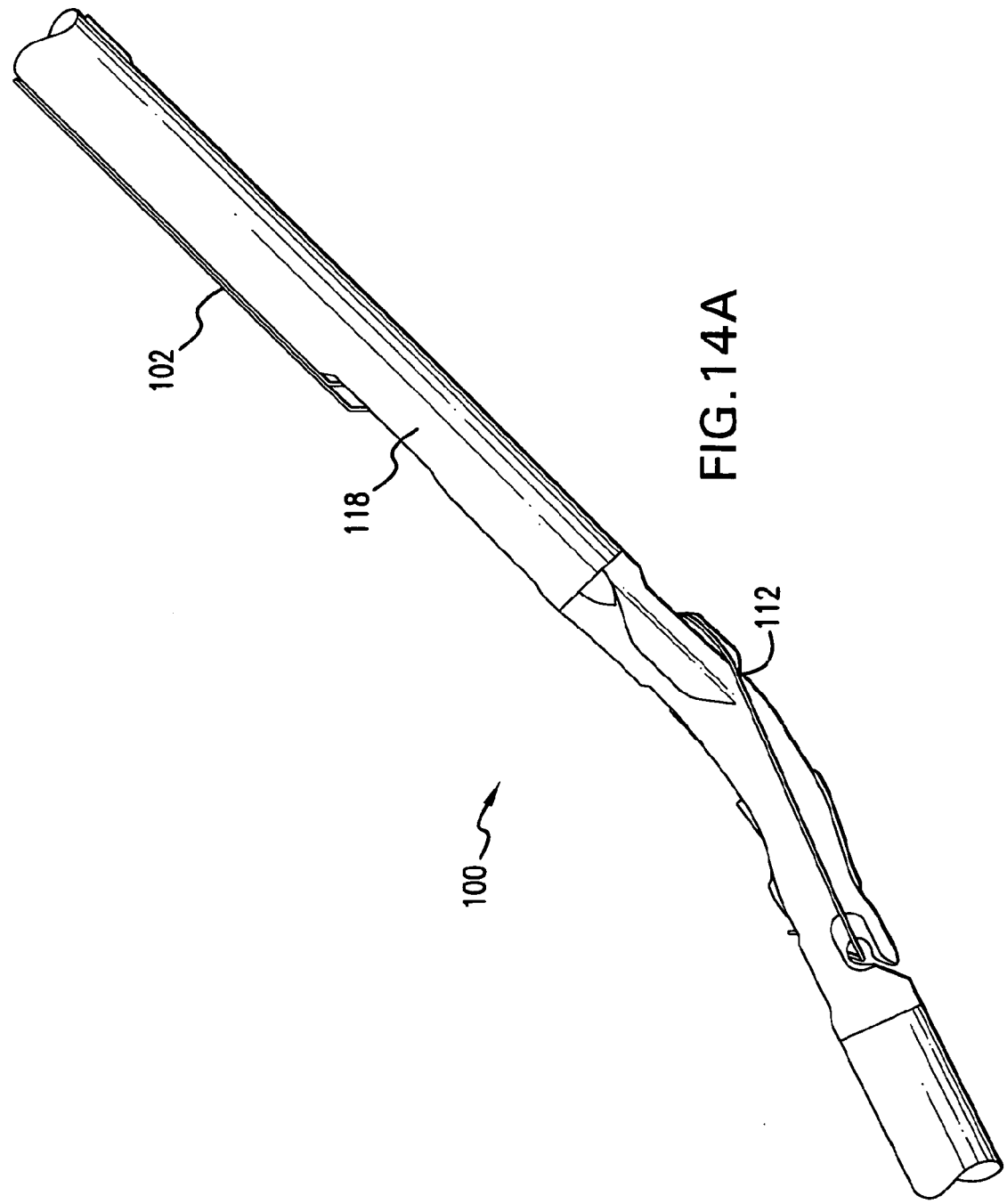
FIGS. 14A and 14B are enlarged partial side views of a suturing device in accordance with one embodiment of the present invention.
Figure 14B:
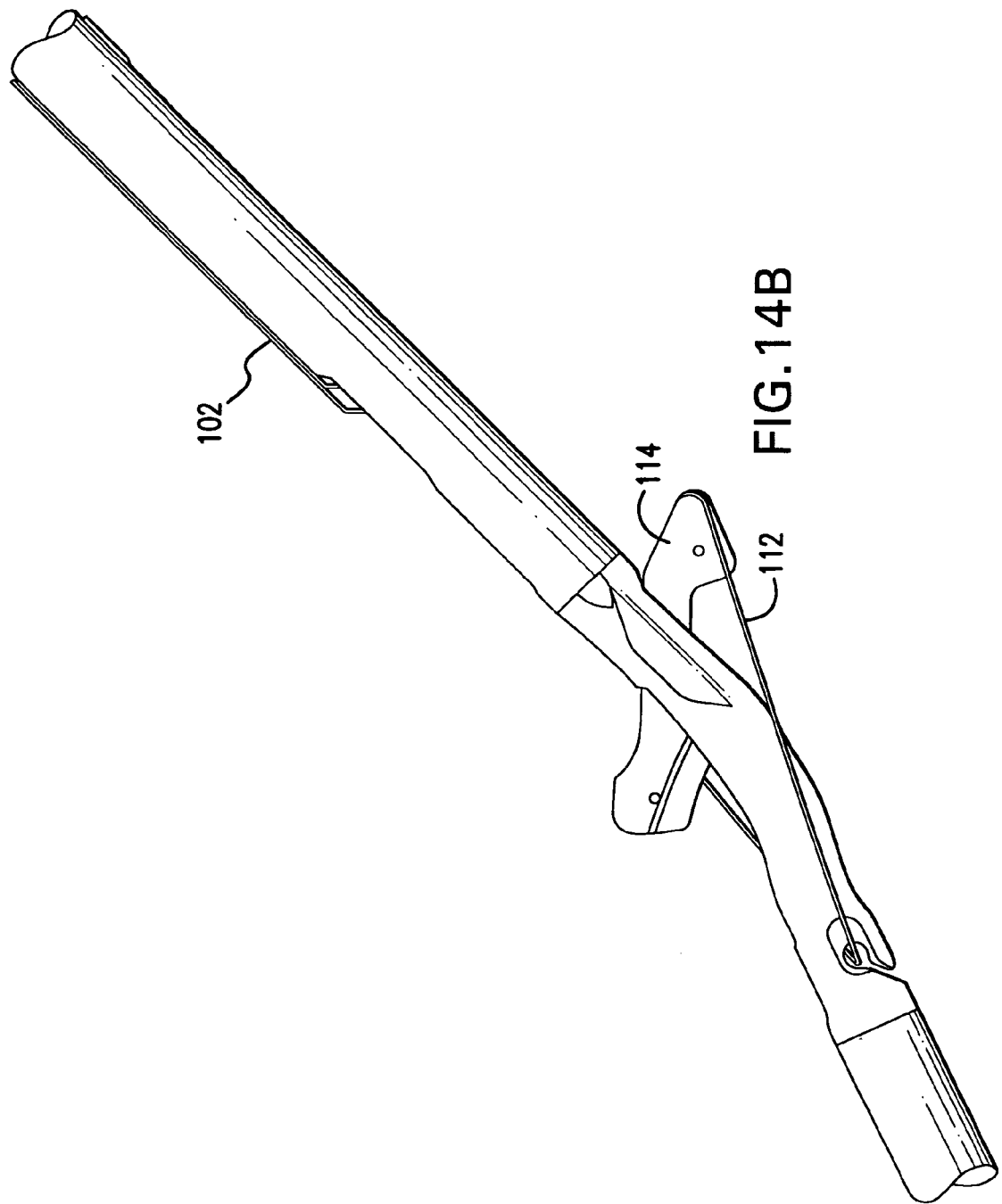

FIGS. 14A and 14B show an embodiment of a vessel closure device 100. The discussion of vessel closure device 10, 10', and 70 also can apply to vessel closure device 100, and vice versa. This embodiment includes an articulatable foot 114 (FIG. 14B) having a pair of penetrator receptacles (described below). Although each penetrator receptacle contains a fitting (or cuff) for coupling a flexible filament to a tip of an associated penetrator, the filament in this case may be a short length of suture such as a link 112 spanning directly between the penetrator receptacles. Rather than pulling the two ends of an extended loop through the needle paths and proximally out the tissue tract for tying, closure system 100 advances a single end of the suture distally along one needle path, across the puncture, and then proximally along the other needle path. To provide this interaction, at least one needle includes means for attaching suture 102 to the link 112, here in the form of a detachable coupling structure carried on the at least one needle. This structure facilitates the use of a pre-tied knot. It will be understood that all or portions of the needle path can include one or more of the friction reducing structures described herein or those structures known to one skilled in the art for performing the functions identified with the described friction reducing structures.

Figure 15A:
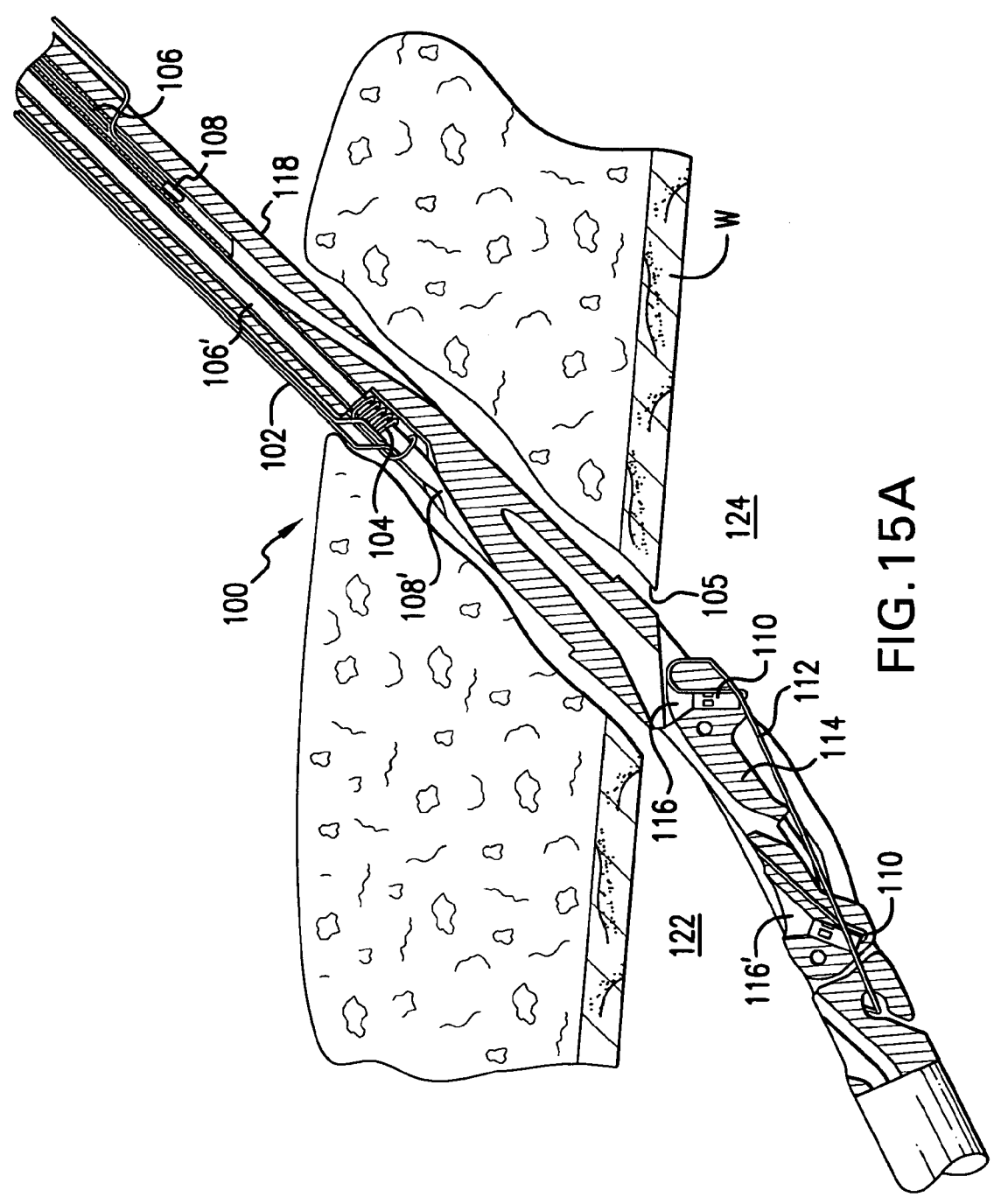

FIG. 15A shows a side, cross-sectional view of the device 100 in a position prior to deployment of the foot 114. The device 100 has been advanced through the incision 105 in the arterial wall W. For ease of description, reference numeral 122 indicates the anterior side of the device, and reference numeral 124 denotes the posterior side of the device. Device 100 has a rigid shaft 118 that has channels defined therein to carry the elongate bodies or penetrators 106 and 106'. Penetrator 106' may also be referred to as the anterior penetrator, and penetrator 106 may be referred to as the posterior penetrator. For purposed of description and not limitation, the anterior penetrator 106' carries the pre-tied knot 104, and posterior penetrator 106 carries the detachable coupling structure or penetrator tip 108. Anterior penetrator 106' defines a penetrator tip 108' at its distal end.

The articulatable foot 114 includes anterior and posterior penetrator receptacles 116' and 116, respectively. These receptacles are also referred to as cuff pockets. Cuffs 110 are shown positioned in cuff pockets 116' and 116. A link 112 extends between the cuffs 110.

Figure 15B:
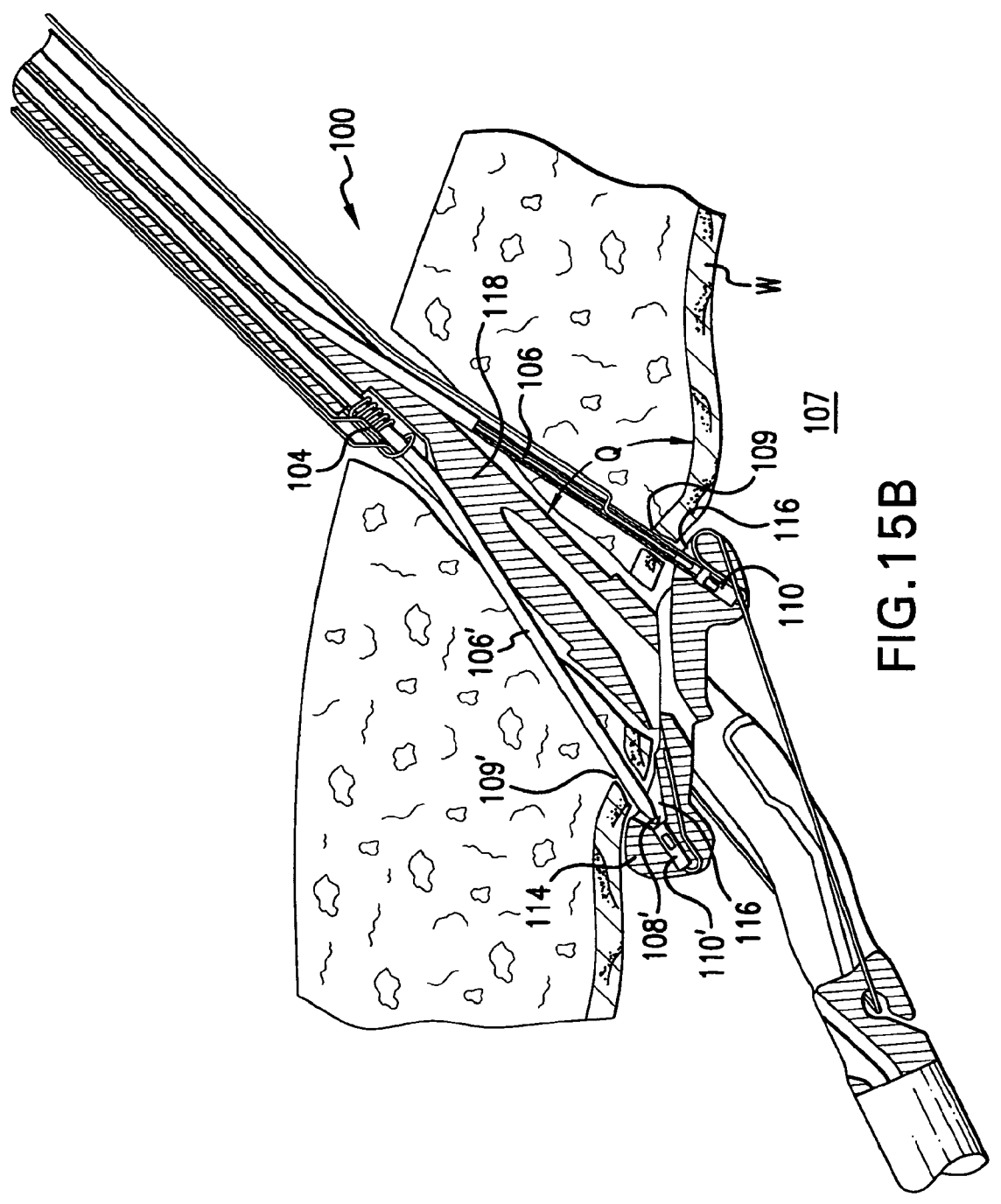

FIG. 15B shows the foot 114 deployed so as to position the cuff pockets 116 to receive the first and second penetrators 106' and 106. As shown in FIG. 15B, the anterior penetrator 106' has the pre-tied knot 104 disposed about a proximal portion of its length. Alternatively, the pre-tied knot 104 may be disposed about the periphery of a knot tube, through which the anterior penetrator 106' may pass (as described in further detail below).

FIG. 15B illustrates the suturing device 100 deployed within a lumen 107 in accordance with an embodiment of the present invention. As may be seen with reference to the Figure, the suturing device 100 includes an elongate body 106' having a penetrator tip 108'. The elongate bodies 106 and 106' deploy to form penetrations 109 and 109' within the vessel wall W. The configuration of the penetrator tip 308 allows penetration of the vessel wall W immediately surrounding the incision 105 to form the penetration 309. As such, the penetration of the penetrator tip 108 through the tissue wall W allows for passage of the elongate body 106 through the tissue and into the lumen 107. The elongate body 106 holds the suture 102 as the elongate body 106 passes through the tissue wall W immediately adjacent the incision 105 and into the foot 114.

As may be seen with reference to FIG. 15B, in this embodiment, the foot 114 has a single unit design where the cuffs 110 and 110' are disposed on opposite sides of the suturing device 100 and the foot 114. This orientation allows balance of forces during the deployment of the elongate bodies 106 and 106', thereby allowing precise suturing and minimizing the possibility of incorrectly suturing the incision 105. Also, as may be seen with reference to the Figure, the suturing device 100 delivers the suture longitudinally relative to the lumen 107, thereby minimizing arterial diameter constriction. Likewise, in this embodiment, the foot 114 is positioned at an angle "Q" relative to the shaft 118 of the suturing device 100. In one configuration, the angle "Q" is in a range between about 20 degrees and about 60 degrees, while in another configuration the angle "Q" is about 40 degrees. The angle "Q" approximates the puncture angle commonly used to access the femoral artery. The angle Q and the rigid character of the shaft 118 serve to provide accurate, virtually simultaneous "cuff capture" by both the anterior and posterior penetrators. Moreover, since the device 100 can be used without an introducer sheath, the rigid nature of the shaft 118 provides the control of the travel of penetrators as they move distally to engage the cuffs. The device 100 can therefore be used in the same femoral artery access puncture without disturbing the existing tissue tract and causing undue discomfort to the patient.

When both the elongate bodies 106 and 106' and the suture 102 pass through the lumen wall W and into the lumen 107, the elongate bodies 106 and 106' engage with the foot 114. The penetrator tip 108 and anterior penetrator tip 108' of the elongate bodies 106 and 106' engage with cuffs 110 and 110' of the foot 114. The cuffs 110 and 110' include a link 112 that connects the cuffs 110 and 110' to one another. It should be noted that the cuffs 110 and 110' facilitate connection of the penetrator tip 108 with the anterior penetrator tip 108' such that the penetrator tip 108 and the anterior penetrator tip 108' are coupled to one another via the link 112.

Figures 16A, 16B:
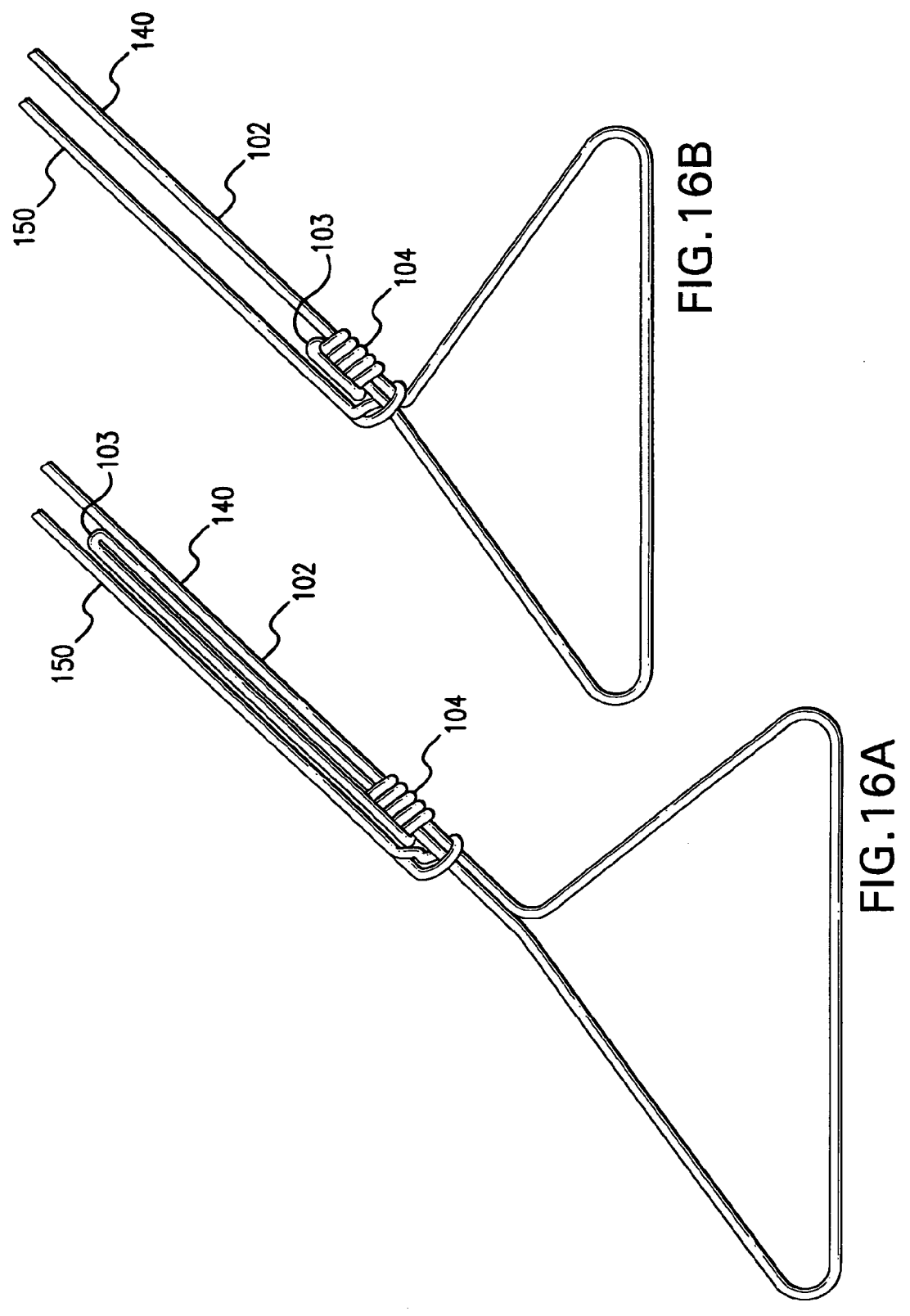

FIGS. 16A and 16B show the suture bight in the pre-deployed state (FIG. 16A) and the deployed state (FIG. 16B). The suture 102 is arranged to provide the pre-tied knot 104 that automatically travels down from the shaft of the device where it is stored prior to delivery to the tissue wall. The loop 104 of suture 102 serves to pull the knot 104 down the rail portion 140 of the suture during deployment. It should be noted that it would be desirable to be able to distinguish the ends 140 and 150 of the suture 102 during deployment so that the correct end is pulled by the operator to advance the knot. Should the non-rail end be pulled, the knot may be prematurely tightened before it is advance to its deployed position at the wall of the vessel.

The ends of the suture may be distinguished from each other by changing the color of one end (e.g. with dye), providing an attachment on one end (e.g. shrink wrap tubing, a bead, etc.) or with the suture itself (e.g. tying a knot in one end).

Figure 15C:
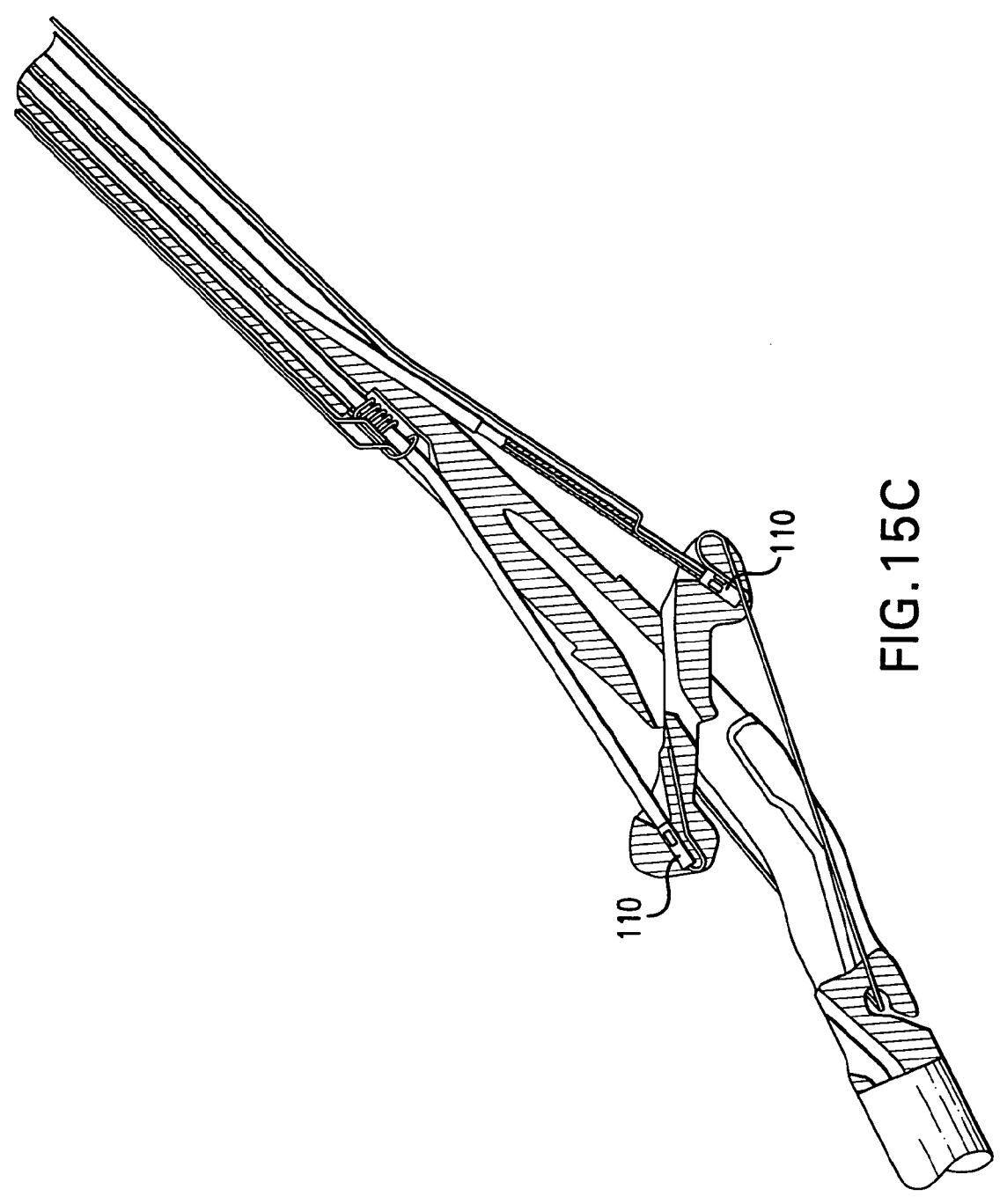
Figure 15D:
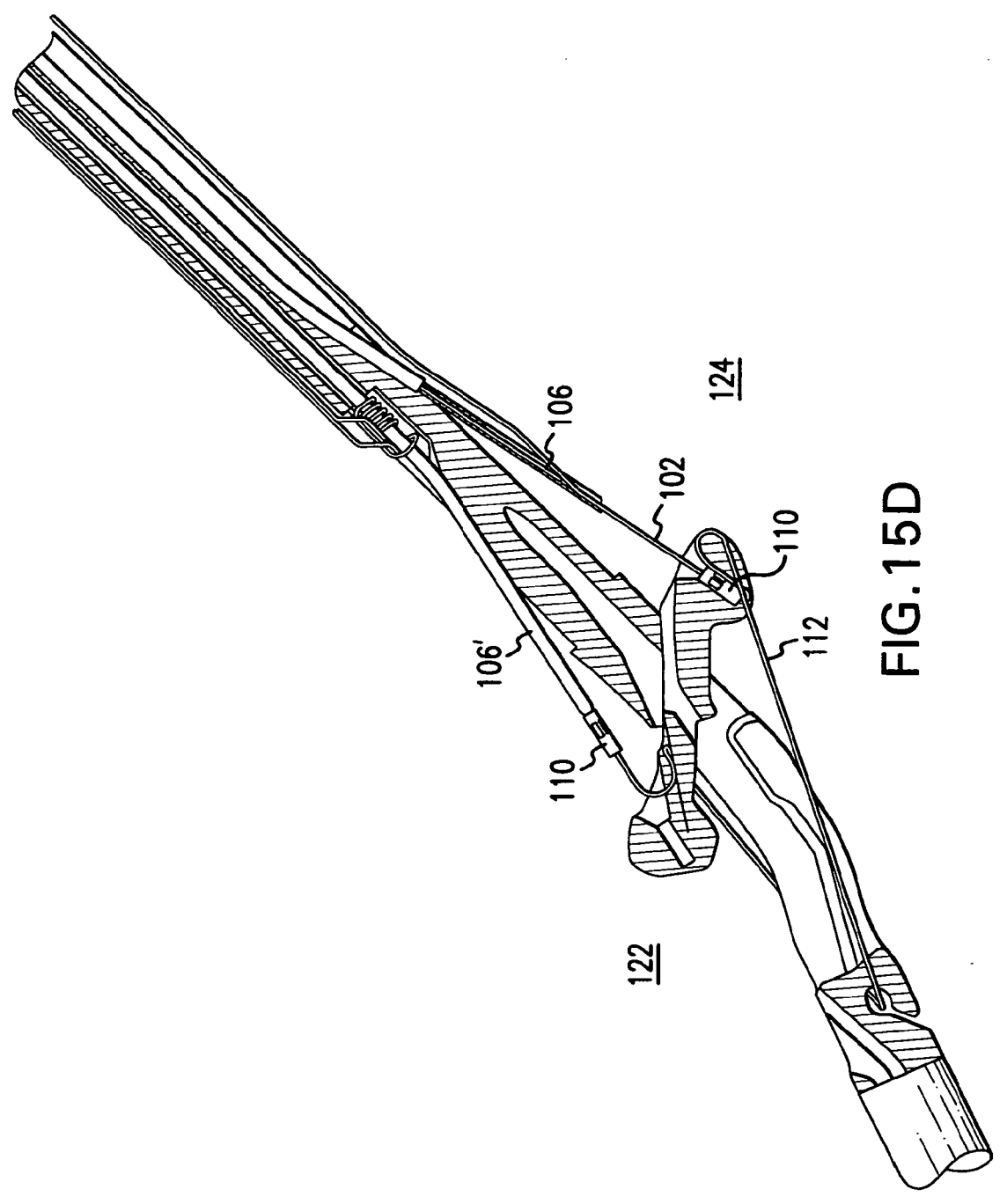

FIG. 15C shows the penetrator tips fully deployed into and engaged with the cuffs 110. FIG. 15D shows the penetrators being retracted after the tips have engaged the cuffs 110. On the anterior side 122, the penetrator 106' is pulling the anterior cuff 110 distally. On the posterior side 124, the penetrator tip 108 has been disengaged from the penetrator 106, via a mechanism described below. As shown in FIG. 15D, the link 112 is now coupled to one end of the suture via posterior cuff 110. Suture 102 is also shown exiting the posterior penetrator shank via an opening in the side of the penetrator shank.

Figure 15E:
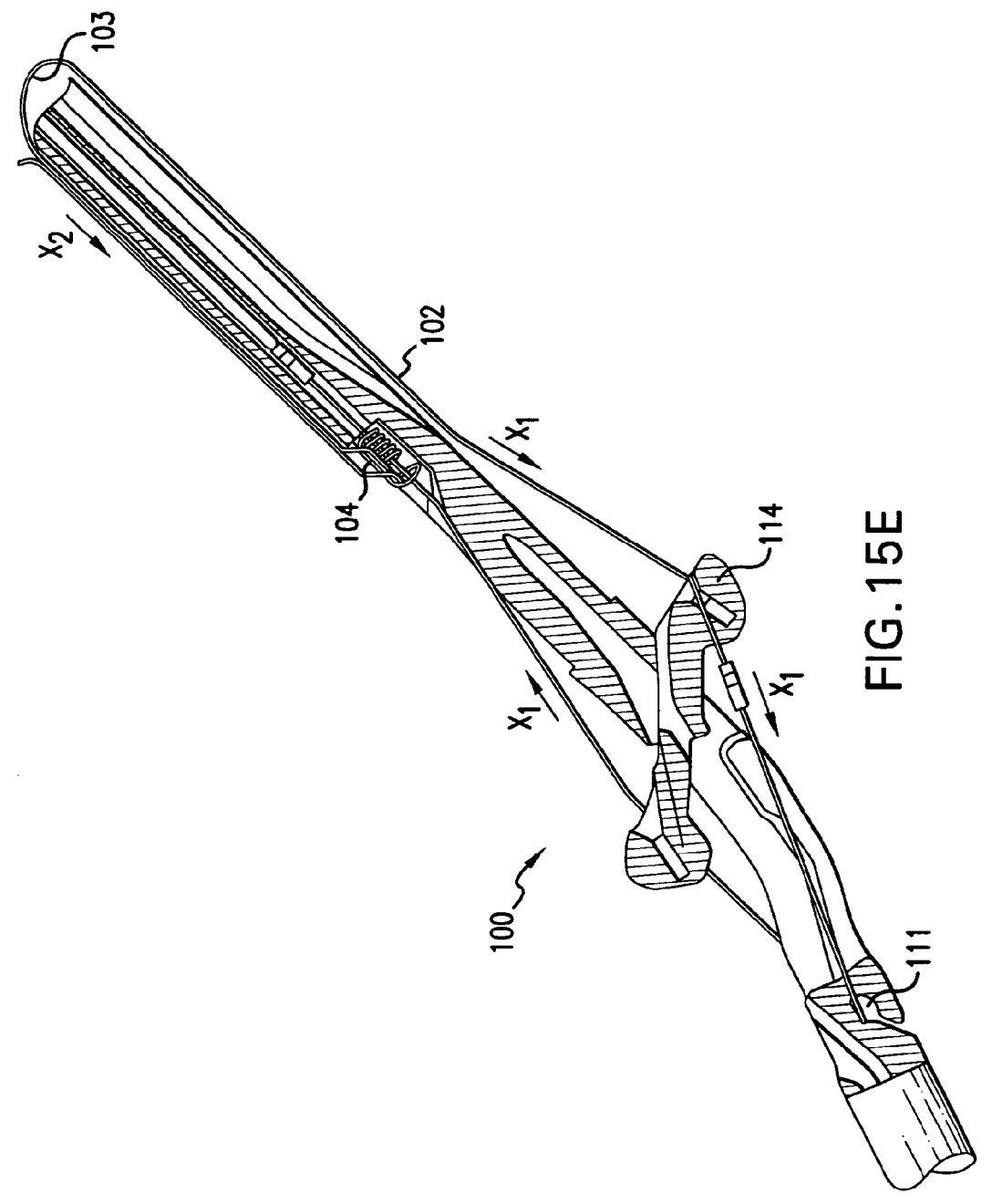

Referring to FIG. 15E, after deployment of the foot 114, the suture 102 moves as indicated by directional arrows $X_1$. As the suture 102 moves, a suture loop 103 also moves in a direction indicated by directional arrow $X_2$ towards the foot 114 and the incision (not shown). The suture 102 moves through the foot 114 and through an opening distal to the foot 114 that defines a suture-bearing surface 111. The suture-bearing surface 111 is disposed at a distal end of the suturing device 100 separate from the foot 114, in this embodiment. The suture bearing surface 111 bears forces placed on the suture 102 during suturing. As such, the suture-bearing surface 111 minimizes forces placed on an incision during incision tensioning, thereby minimizing the possibility of damaging tissue immediately surrounding the incision. In this embodiment, the suture bearing 111 is a slot disposed at a distal end of the suturing device 100, which includes a passage for the suture 102 during incision suturing as shown with reference to the Figure.

As the suture loop 103 and the suture 102 move, the pre-tied suture knot 104 also moves in the same direction as the suture loop 103 towards the foot 114 and the incision. The suture loop 103 continues to move the pre-tied suture knot 104 towards the incision until the suture 102 and the pre-tied suture knot 104 suture the incision formed in the arterial wall. It should be noted that a suture trimmer might be used to assist the delivery of the knot 104 to an arteriotomy. The suture trimmer may be any device suitable for pushing the knot towards the arteriotomy and trimming suture immediately adjacent the knot 104 once the knot is tightened.

Figure 15F:
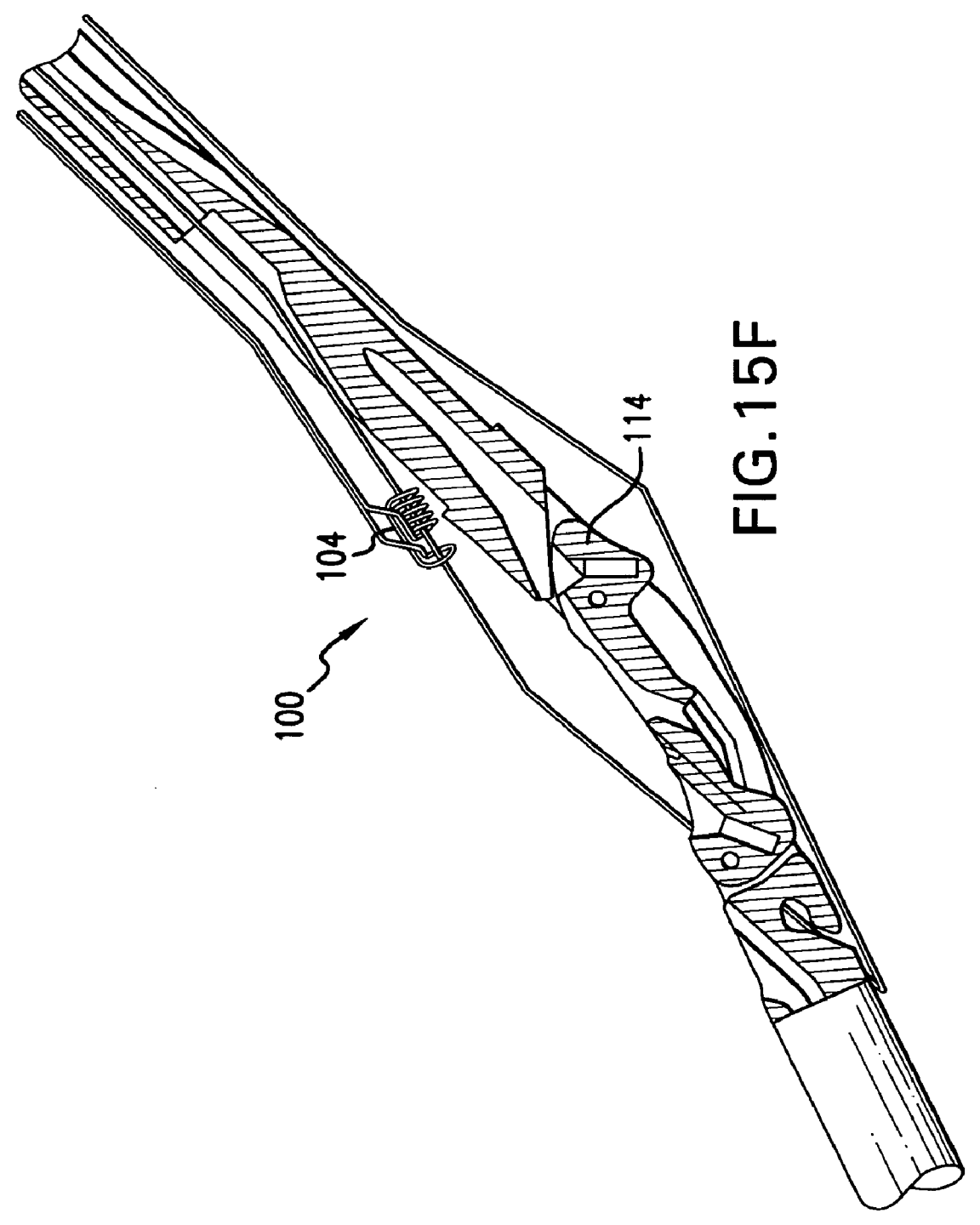

Now making reference to FIG. 15F, the suturing device 100 delivers the pre-tied suture knot 104 to the incision and the foot 114 is returned to its non-deployed position. The penetrators (not shown) have been retracted, the link has been fully retracted through the knot, and the knot has been advanced to the vicinity of the arterial wall. When the body of the device is removed, a stitch can remain in place across the incision in the artery. It should be noted that embodiments of the device described herein place a stitch of suture in a longitudinal orientation with respect to the vessel so as to minimize transverse vessel constriction and also to take advantage of the transverse orientation of the fibers of the vessel tissue.

FIGS. 16A and 16B show the suture bight in the pre-deployed state (FIG. 16A) and the deployed state (FIG. 16B). The suture 102 can be arranged to provide the pre-tied knot 104 that automatically travels down from the shaft of the device where it is stored prior to delivery to the tissue wall. The loop 104 of suture 102 serves to pull the knot 104 down the rail portion 140 of the suture during deployment. It should be noted that it would be desirable to distinguish the ends 140 and 150 of the suture 102 during deployment so that the correct end is pulled by the operator to advance the knot. Should the non-rail end be pulled, the knot may be prematurely tightened before it is advanced to its deployed position at the wall of the vessel.

The ends may be distinguished from each other by changing the color of one end (e.g. with dye), providing an attachment on one end (e.g. shrink wrap tubing, a bead, etc.) or with the suture itself (e.g. tying a knot in on end).

Figures 17A, 17E:
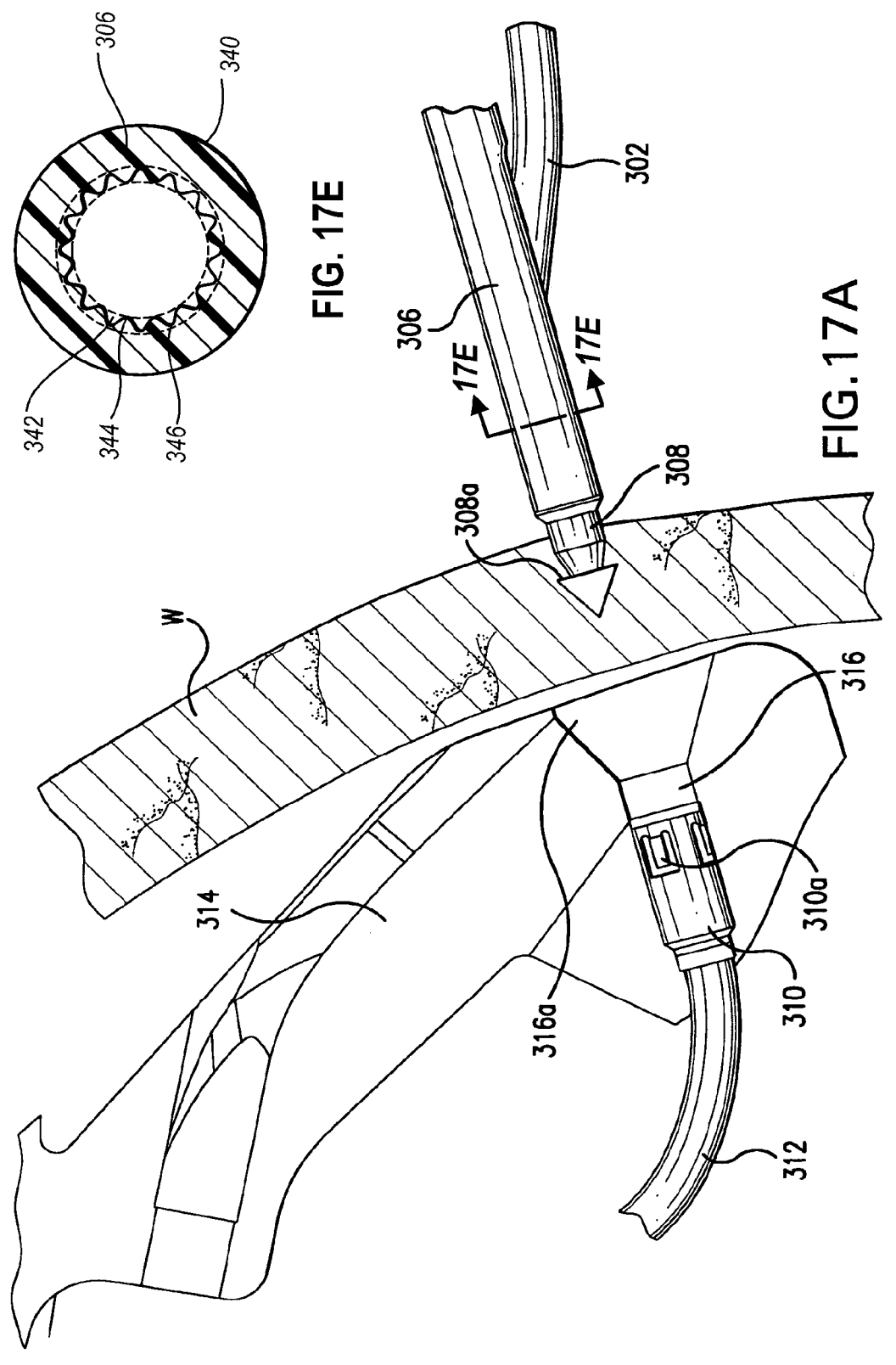

FIG. 17A shows an enlarged detail of the posterior portion of the foot of one embodiment of suturing device 300. In an accordance with an embodiment of the present invention, the elongate body 306 may be any type of structure capable of penetrating the wall of a lumen, such as an artery, a blood vessel, or the like. In addition to the penetration capability, the elongate body 306 may be a hollow tube capable of holding suture. Examples of such structures may include a hypodermic needle or the like. A cross-sectional configuration of another structure is illustrated in FIG. 17E.

Figure 17B:
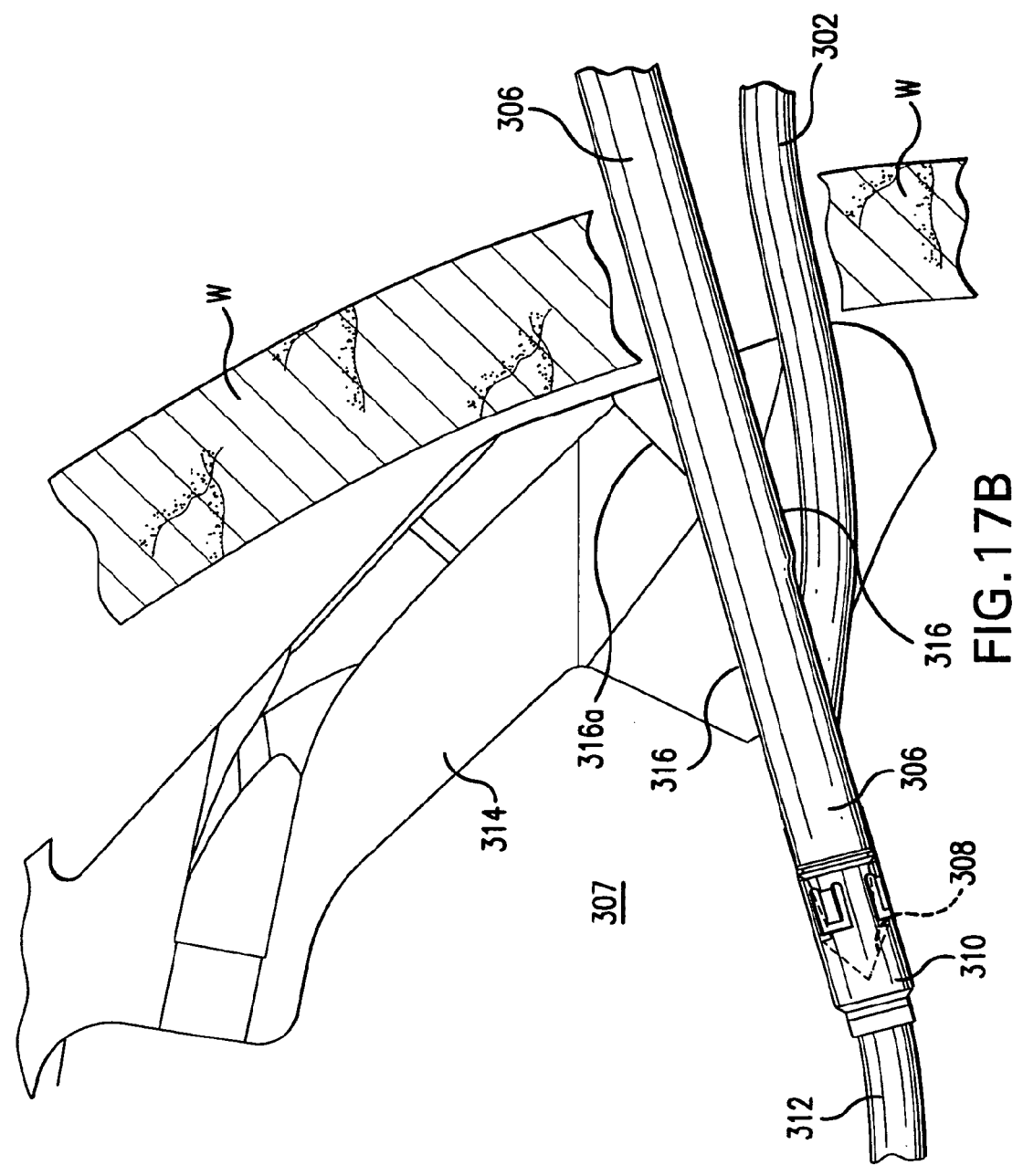

With reference to FIG. 17E, the elongated body 306 can be configured to reduce the frictional engagement or contact between the suture 302 (FIG. 17A) and the elongated body 306. As illustrated, the elongated body 306 can include an exterior surface 340, and an interior surface 342, the interior surface 342 defining a lumen that can be similar to the lumen or interior surface described with respect to FIG. 7A. The illustrated interior surface 342 can include at least two portions having differing diameters; at least one raised portion 344 and at least one recessed portion 346, optionally a plurality of raised portions 344 and a plurality of recessed portions 346, optionally in an alternating configuration, which extend longitudinally along the length of the elongated body 306. The combination of the raised portions 344 and recessed portions 346 reduce the contact surface between the suture 302 (FIG. 17A) and the elongated body 306 and thereby reduce the frictional forces between the suture 302 and the elongated body 306 or the suture drag when the suture is moved inside the elongated body 306. The portions 344 and 346 are another example of a structure capable of performing the function of reducing frictional engagement between a suture and the structure which selectively receives and/or restrains the suture. Accordingly, the discussion related to portions 86 and 88 of FIG. 7A also apply to portions 344 and 346 of FIG. 17B.

As illustrated, the plurality of raised portions 344 define a first inner diameter $id_1$, while the plurality of recessed portions 346 define a second inner diameter $id_2$. With an outside diameter ($od_1$) of the elongated body 306, $id_1$ can be about 0.030 inches, while $id_2$ can any diameter between the $od_1$ and the $id_1$. In the illustrated configuration, the $id_2$ can be between about 0.040 inches and about 0.030 inches. It will be understood by those skilled in the art that various other configurations are possible. For example, although the raised portions 344 and the recessed portions 346 are generally uniformly distributed on the interior surface 346 irregular distribution of the portions 344 and 346 is possible. Further, although the portions 344 and 346 are generally depicted as being uniform in size, shape, or general configuration, non-uniform size, shape, or configuration of portions 344 and 346 possible.

Returning to FIG. 17A, the suturing device 300 stores the elongate body 306 within its shaft (not shown). As previously described with reference to FIGS. 2A through 2C, a user deploys a handle (not shown) of the suturing device 300 thereby deploying the elongate body 306 and the penetrator tip 308. During deployment, the elongate body 306 and the penetrator tip 308 penetrate the lumen wall W immediately surrounding the incision 305 and enter the lumen 307 of a patient, as shown with reference the following FIG. 17B.

Once the penetrator tip 308 engages with the cuff 310, the elongate body 306 and the penetrator tip 308, along with the cuff 310, proceed through the foot 314 and into the lumen 307. As may be seen with reference to FIG. 17B, the cuff 310 is pushed through the foot 314, such that the cuff 310 is pushed out of a pocket 316 and through the foot 314 into the lumen 307. Once the cuff 310 and the elongate body 306 enter the lumen 307, the penetrator tip 308 detaches from the elongate body 306 via a push mandrel 315 as shown with reference to FIG. 17C.

Figure 17C:
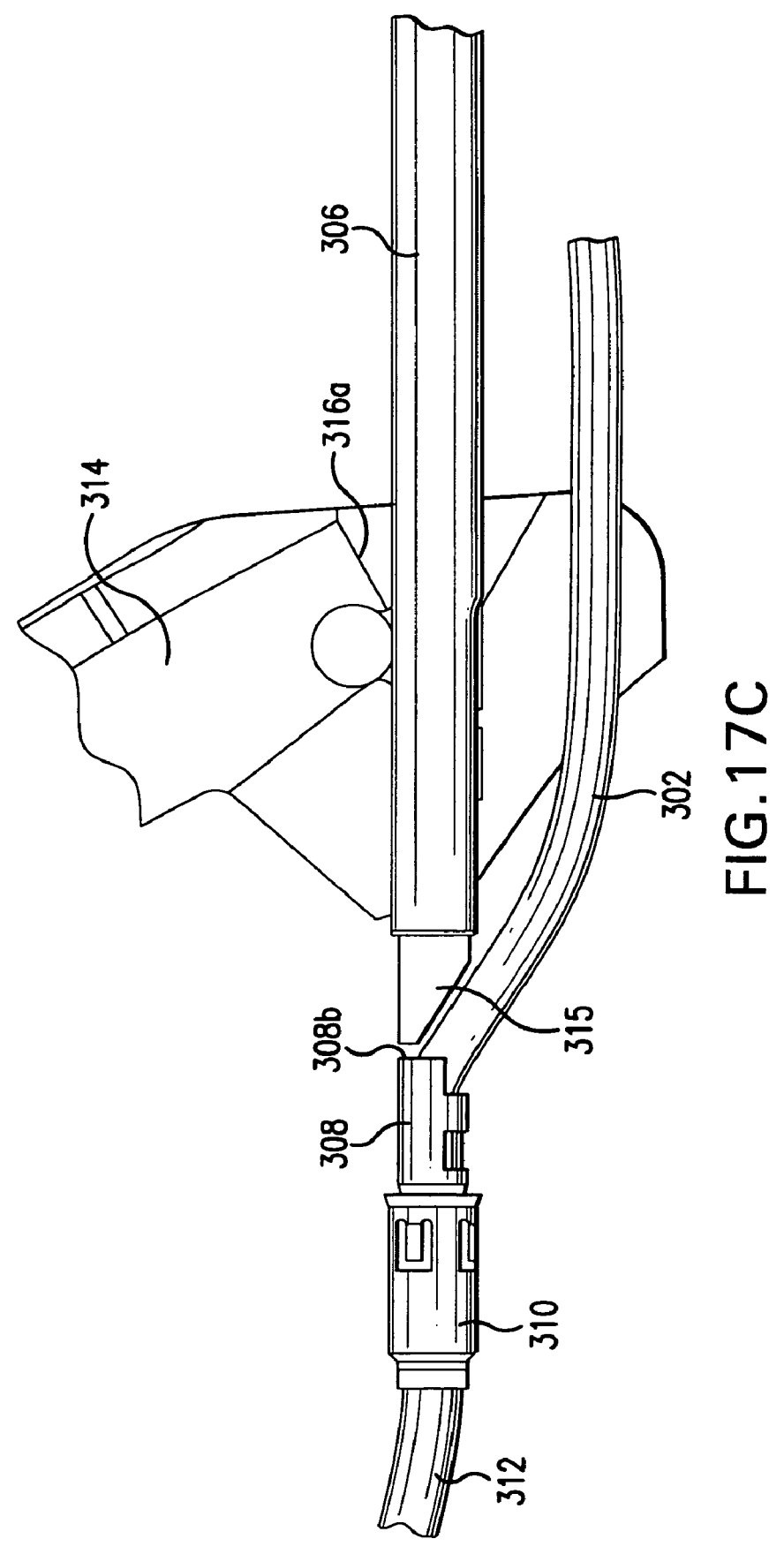

FIG. 17C illustrates the detachment of the penetrator tip 308 from the elongate body 306 in accordance with one embodiment of the present invention. Upon engagement of the penetrator tip 308 with the cuff 310, the push mandrel 315 is further advanced such that it contacts a proximal surface 308b of the penetrator tip 308, and further still until the penetrator tip 308 detaches from the elongate body 306. Upon detachment of the penetrator tip 308 from the elongate body 306, the push mandrel 315 and the elongate body 306 retract from the foot 314, as shown with reference to FIG. 17D.

Figure 17D:
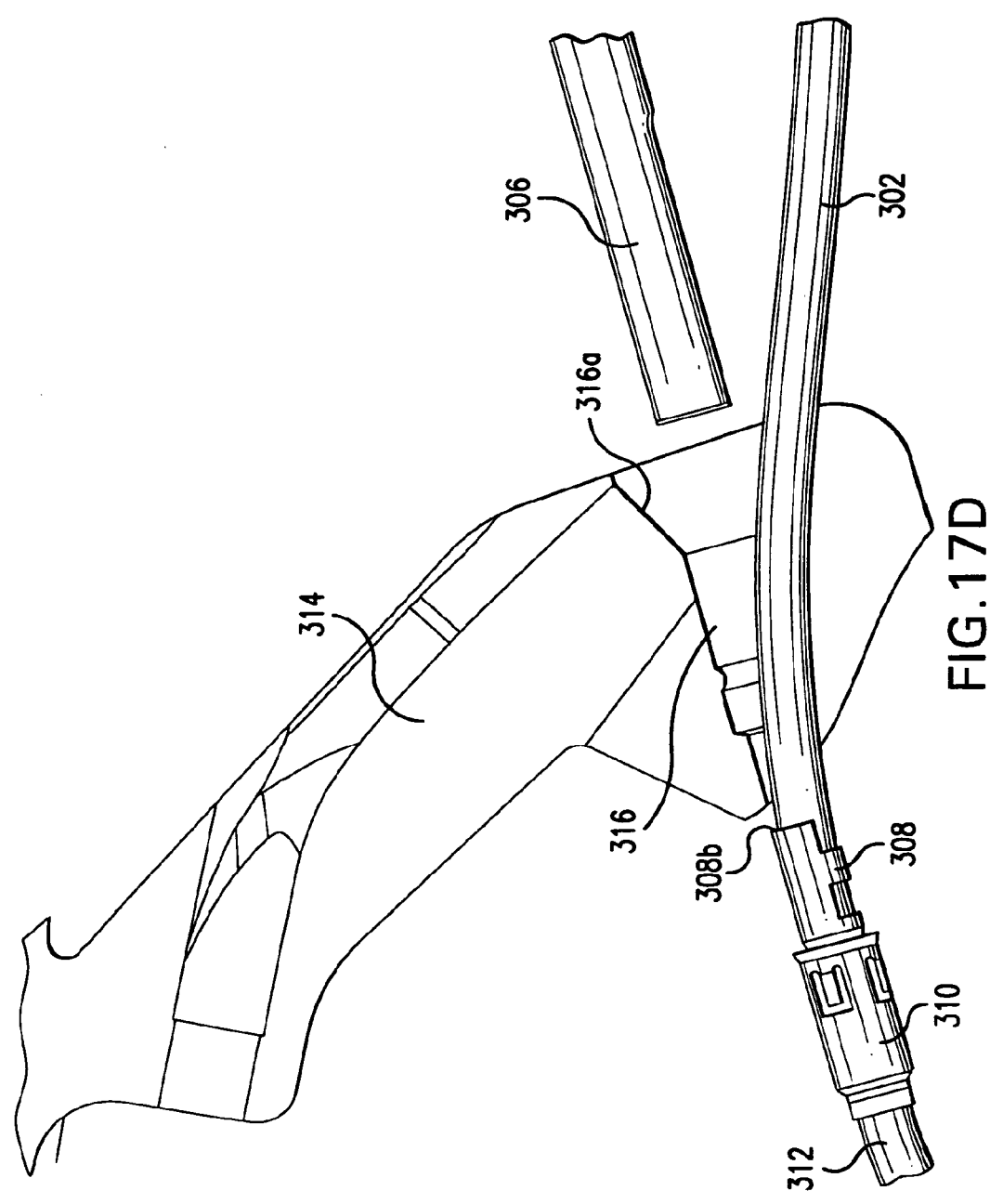

As shown in FIG. 17D, after the penetrator tip 308 detaches from the elongate body 306, the elongate body 306 retracts from the penetrator tip 308 and cuff 310. Meanwhile, on the anterior side of the device (not shown in FIG. 17D), the elongate body 306' also includes the needle tip 308' which engages with the cuff 310' as previously described with reference to FIG. 15C. The needle tip 308' does not disengage from the elongate body 306' upon engagement with the cuff 310'. Therefore, during retraction of the elongate body 306' from within the lumen 307, the needle tip 308' also retracts from the lumen 307 through the penetration 309'. As the needle tip 308' retracts through the penetration 309', the elongate body 306' also retracts the cuff 310'. As previously described, the cuff 310' couples with the cuff 310 via the link 312. During retraction of the cuff 310' through the penetration 309', the cuff 310 and the suture 302 also retract through the penetration 309', thereby drawing the suture 302 through the penetration 309'. It should be noted that the foot 314 may provide suture bearing surface for the suture 302 during operation of the suturing device 300, as shown with reference to FIG. 18A.

Figure 18A:
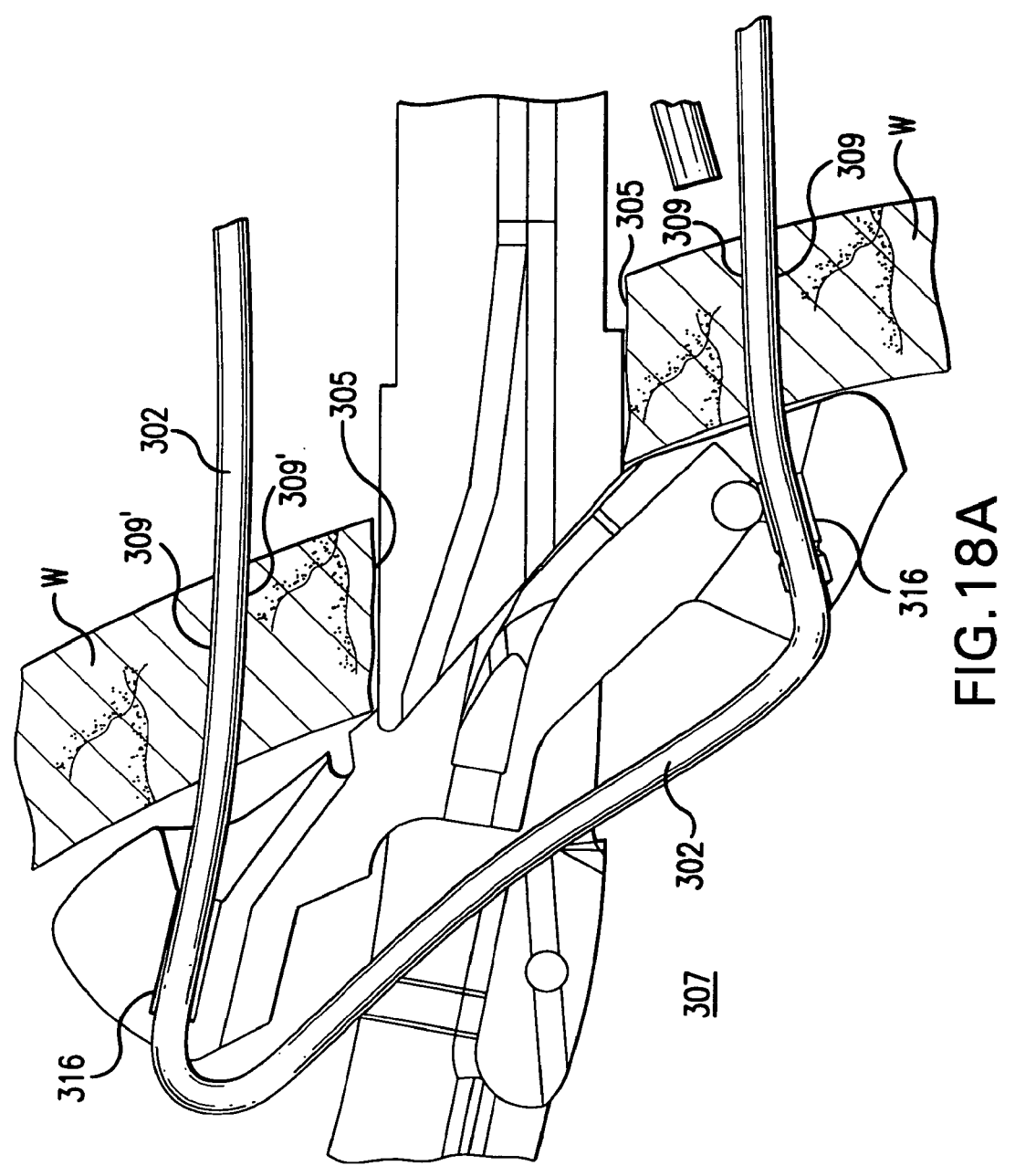

FIG. 18A shows an embodiment of the present invention illustrating the passage of the suture 302 through the lumen 307 and the passageways 309 and 309'. As may be seen with reference to the Figure, the cuff pockets 316 of the foot 314 provide a suture-bearing surface for the suture 302 as the suture 302 is drawn through the passageways. The suture bearing surfaces of the foot 314 minimize the possibility of the suture 302 damaging tissue surrounding the incision 305.

Figure 18B:
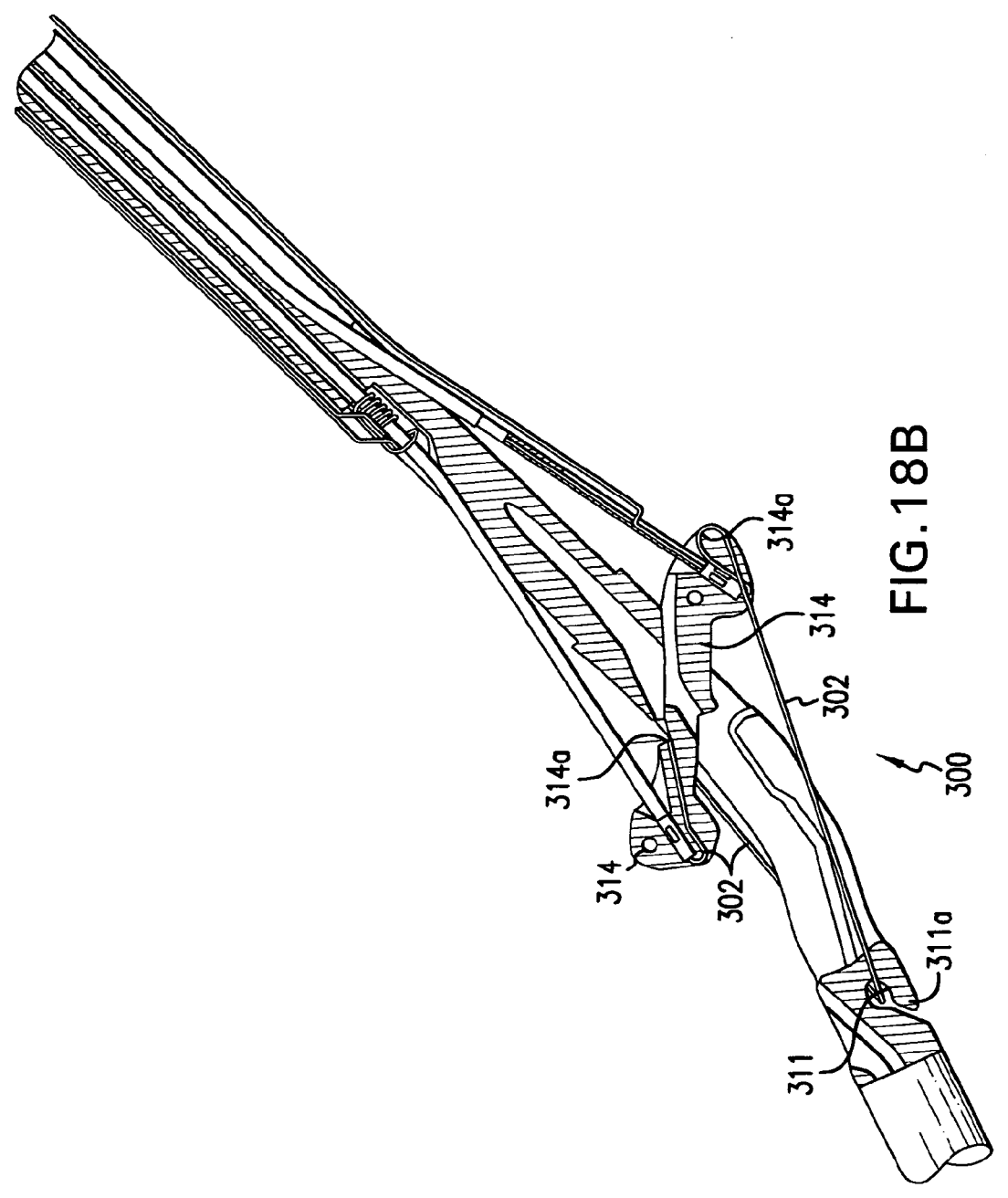

In another embodiment shown in FIG. 18B, the suturing device 300 also provides a suture bearing surface for the suture 302. During retraction of the elongate bodies 306 and 306' from the lumen 307, the suture 302 retracts through the foot suture bearing surfaces 314a and the suture-bearing surface 311 formed distally of the foot. The distal suture bearing surface 311 and the foot suture bearing surfaces 314a guide the suture 302 in order to minimize the possibility of the suture 302 damaging the patient during retraction of the elongate bodies 306 and 306' from the lumen 307. In this embodiment, suture-bearing surface 311 is a slot defined in the body of the device distal of the foot. The slot includes a passage for the link and suture, and an edge 311a. It is contemplated that the edge 311a may contact the edge of the incision in the artery and become caught on the adventitia of the blood vessel. Various devices may be provided, such as flaps, o-rings, etc., that provide a smoother transition over the slot and edge 311a as the device is inserted through the incision. Further, the slot, the elongated body, and/or any of the suture bearing surfaces can include friction reducing structures to aid with passage of the suture along the suture path.

Figure 19A:
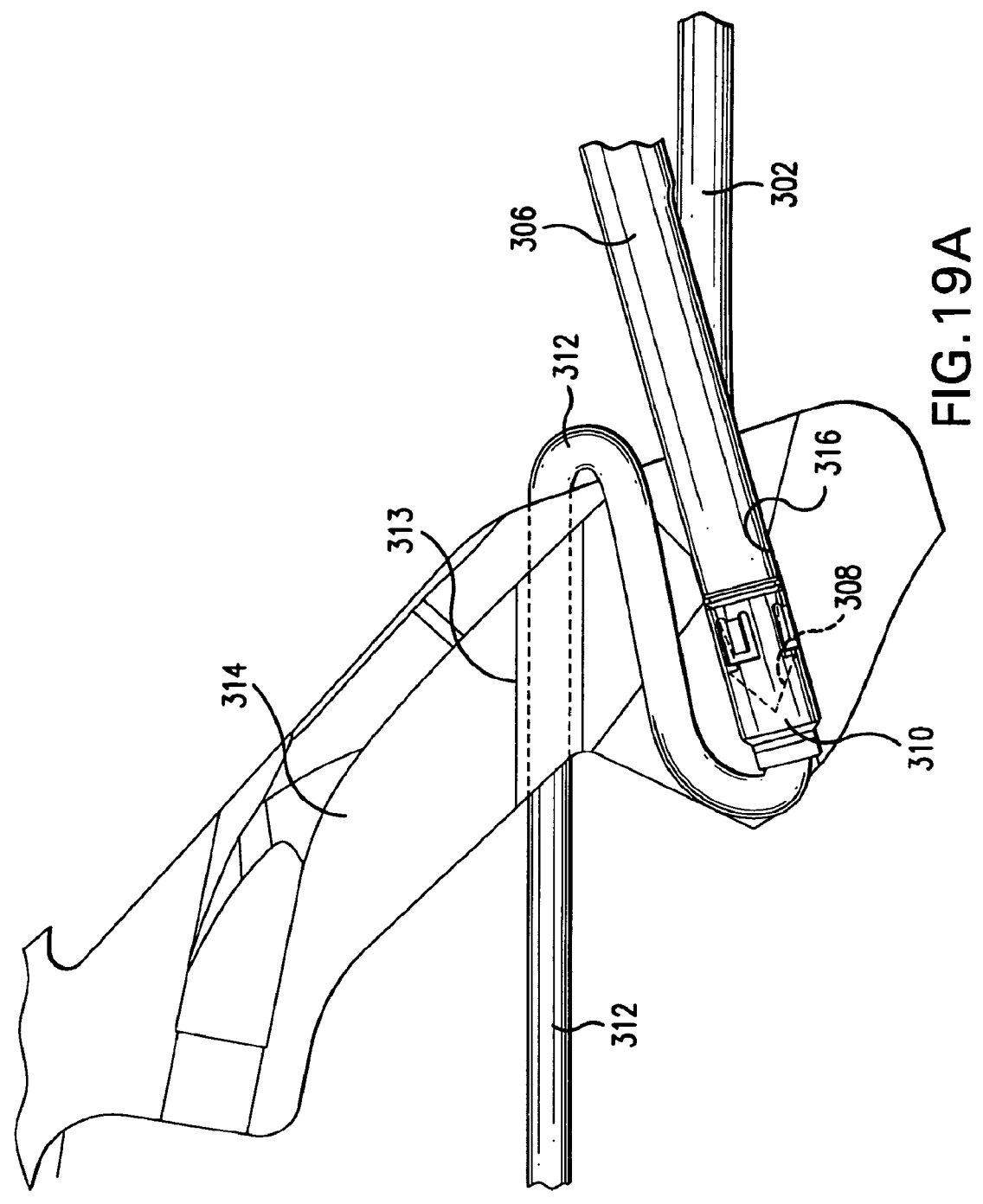
Figure 19B:
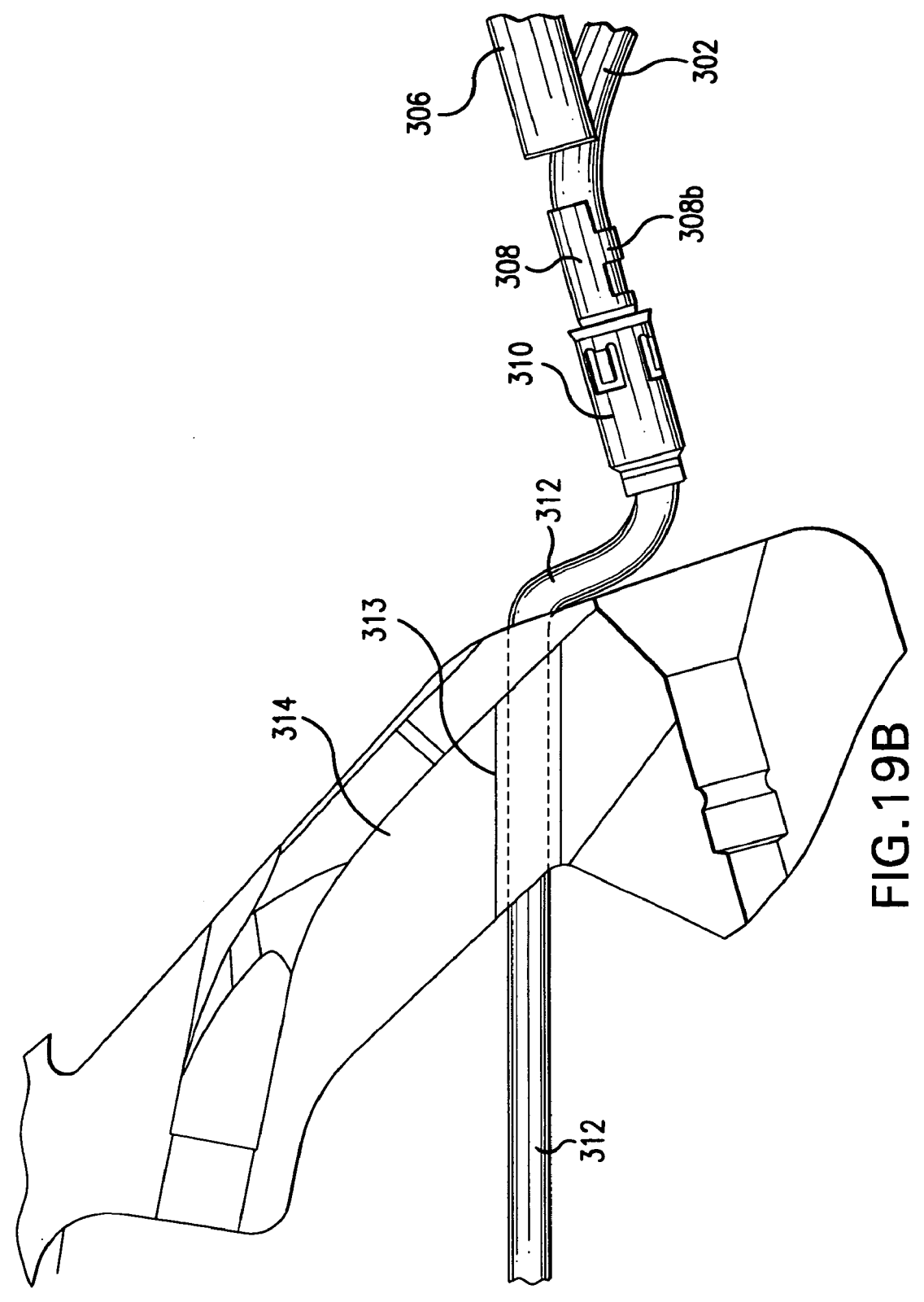

FIGS. 19A and 19B illustrate an alternative embodiment of the present invention for releasing the cuff 310 from the foot 314. In this embodiment, the foot 314 includes link passageway 313 through which the link 312 passes. After the elongate body 306 engages the penetrator tip 308 with the cuff 310, the elongate body 306, during retraction from the foot 314, removes the cuff 310 and the penetrator tip 308 from the foot 314. The force holding the penetrator tip 308 on the elongate body 306 overcomes the force holding the cuff 310 in the cuff pocket 316. Once the cuff 310 clears the foot 314 and attains the orientation shown with reference to FIG. 19B, the previously described push mandrel (not shown) detaches the penetrator tip 308 from the elongate body 306. Upon detachment of the penetrator tip 308 from the elongate body 306, the link 312, along with the cuff 310 and the penetrator tip 308, retracts through the passageway 313 via the link 312 and the elongate body 306'. In an alternate embodiment, the cuff 310 and penetrator tip 308 may be pulled off the elongate body 306 by tension in the link 312.

Figures 20A, 20B:
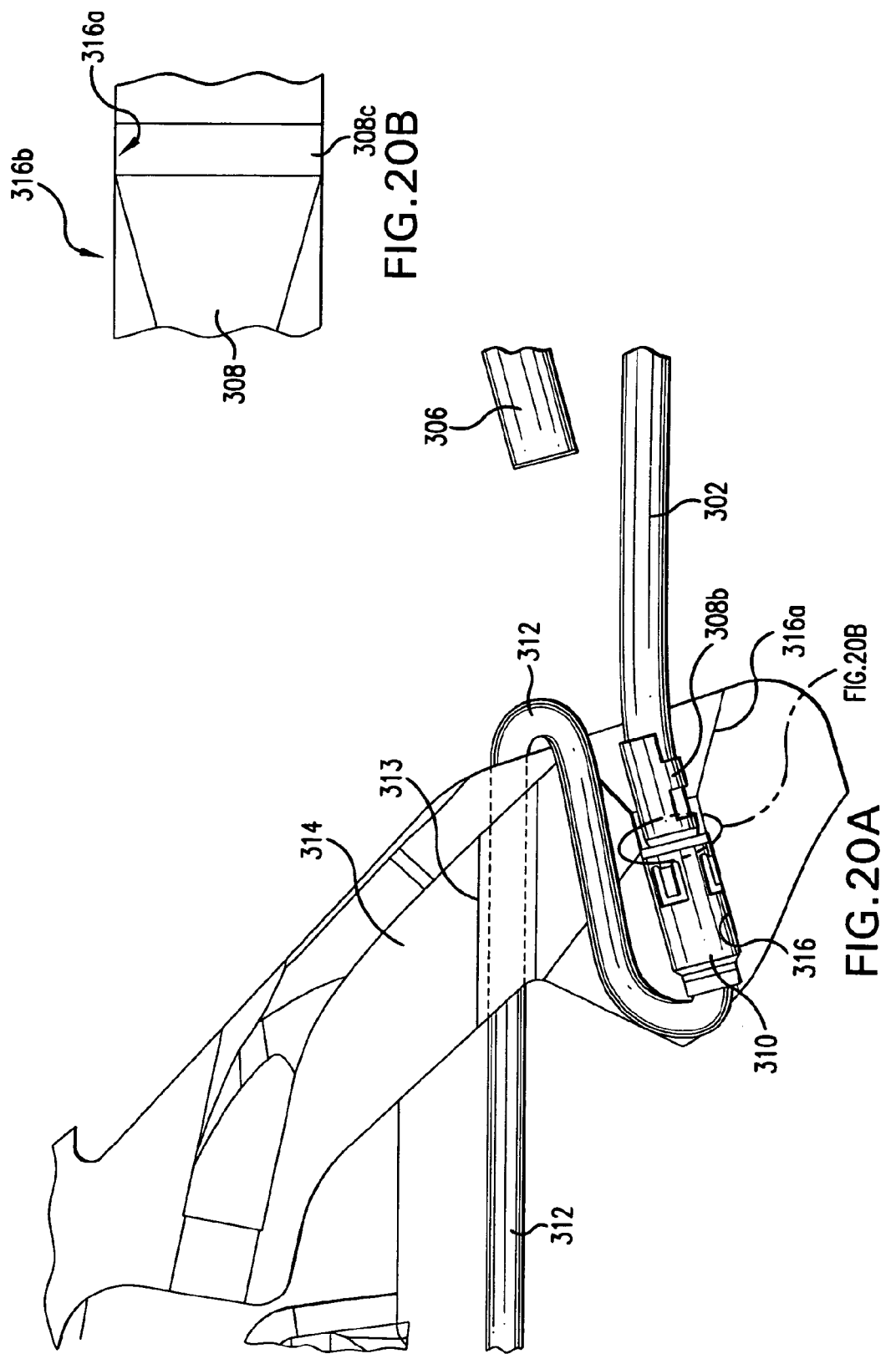
Figure 20C:
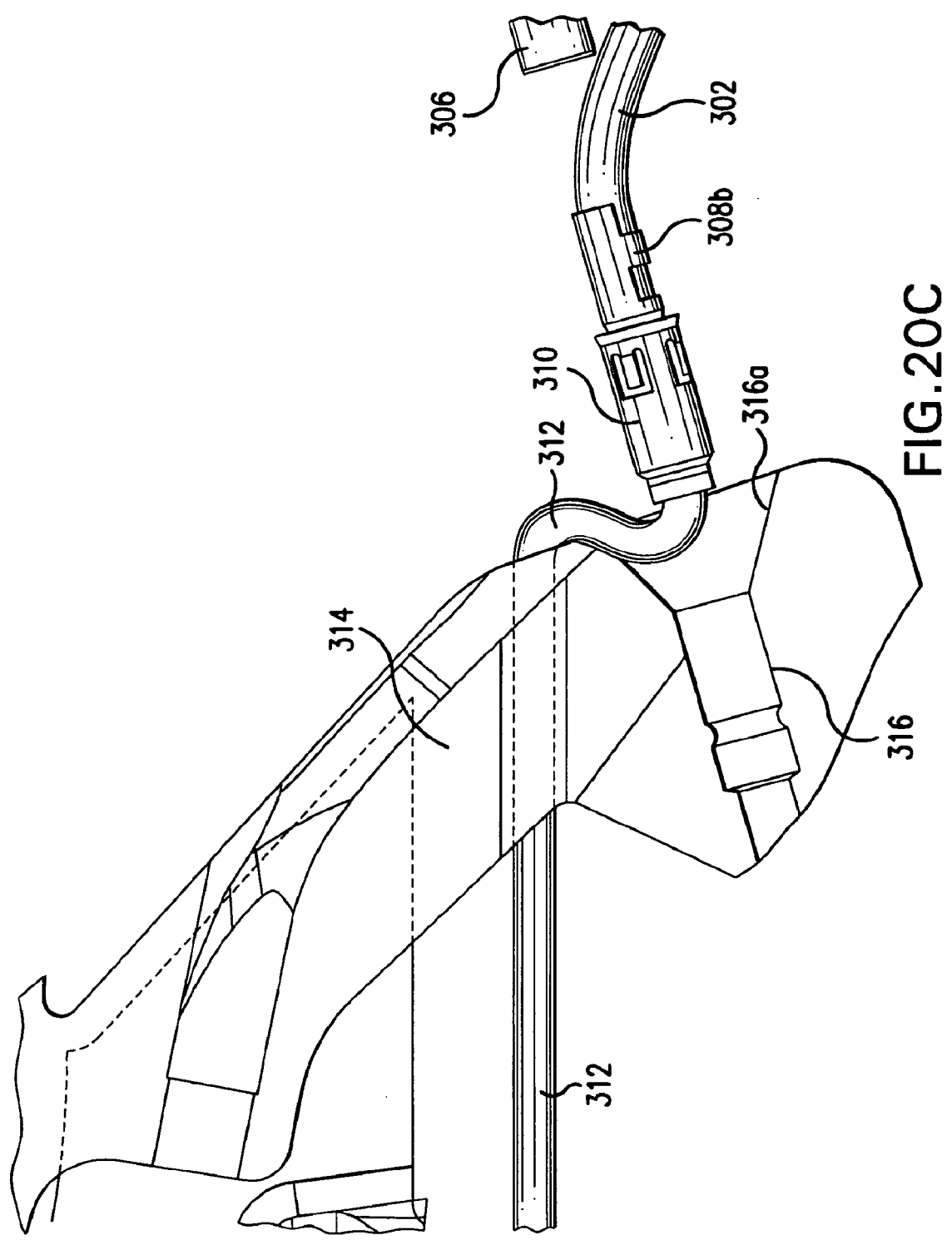

In yet another alternate embodiment shown in FIGS. 20A through 20C, the cuff 310 and penetrator tip 308 may be detached from the elongate body 306 before being removed from the cuff pocket 316. In this embodiment, after the elongate body 306 and the penetrator tip 308 engage with the cuff 310, the push mandrel 315 detaches the penetrator tip 308 from the elongate body 306, leaving it in the cuff pocket 316 to be removed by tension in the link 312, as shown in FIG. 20C.

It should be noted that other methods might be used to detach the penetrator tip 308 from the elongate body 306. These methods include, but are not limited to, detachment through friction or tension. Making reference to FIG. 20B, in an embodiment where friction between the cuff pocket 316 and the cuff causes detachment of the penetrator tip 308 from the elongate body 306, a surface 308c of the penetrator tip 308 frictionally engages with a cuff surface 316a of the cuff pocket 316. During retraction of the elongate body 306 from the foot 314, the frictional engagement between the cuff surface 316a and the penetrator tip surface 308c causes detachment of the penetrator tip 308 from the elongate body 306. In an embodiment where link tension causes detachment of the penetrator tip 308 from the elongate body 306, the link 312 is tensioned such that the link 312 is taut between the cuffs 310 and 310'. As such, the tension of the link 312 prevents movement of the cuff 310 out of the foot 314 along with the elongate body 306 during retraction of the elongate body 306 from the foot 314, thereby causing detachment of the penetrator tip 308 from the cuff 310.

After detachment, during retraction of the elongate body 306 and the elongate body 306' (not shown), the link 312 may draw the cuff 310 and the penetrator tip 308 from the cuff pocket 316. As discussed earlier, the cuff 310' engages with the elongate body 306' and pulls the cuff 310 via the link 312 as the elongate body 306' retracts from the lumen 307. As such, retracting the link 312 pulls on the cuff 310, thereby pulling the cuff 310 from the cuff pocket 316 and through the lumen 307 along with the suture 302, as shown with respect to FIG. 20C.

Figures 21A, 21B:
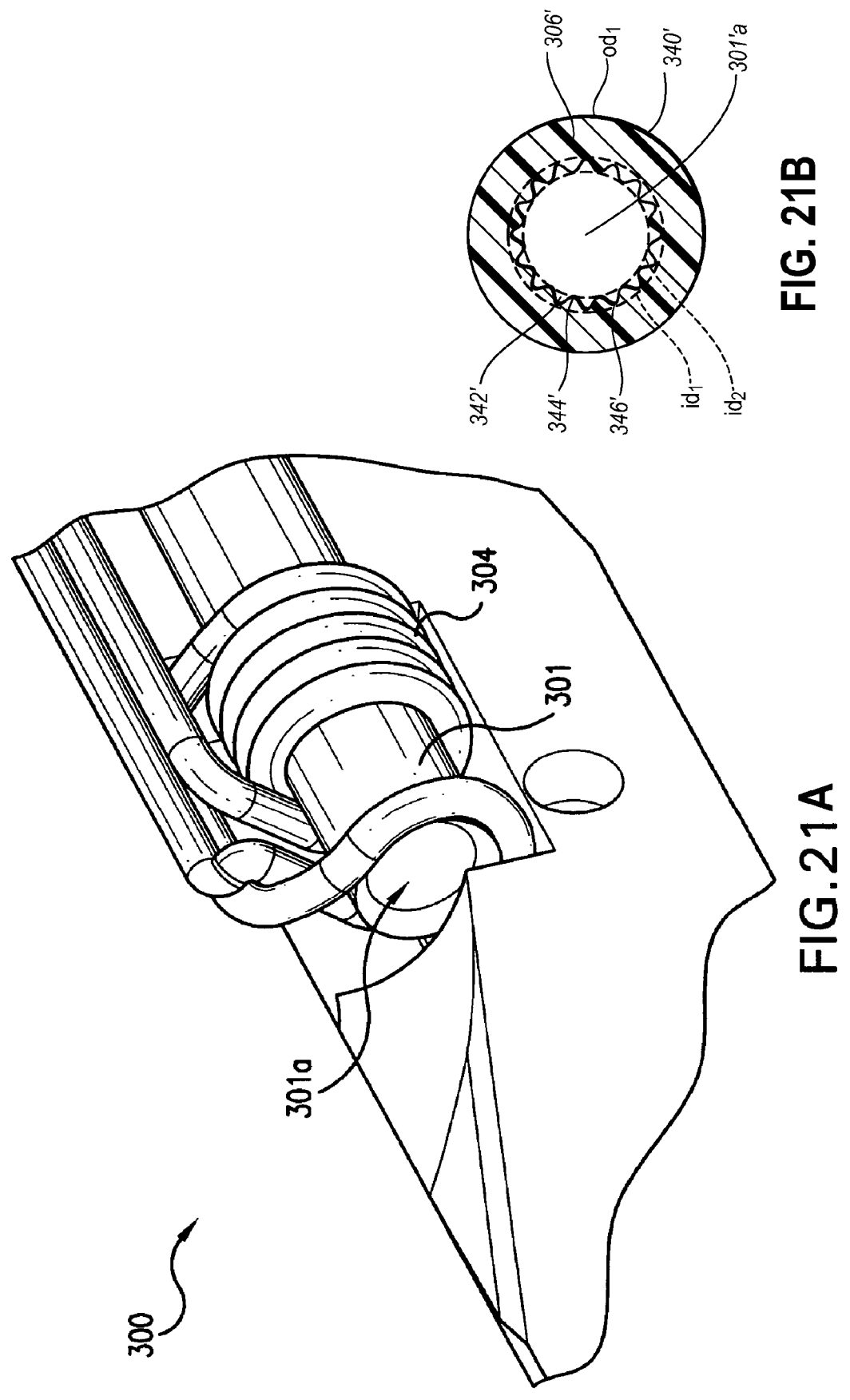

FIG. 21A shows the pre-tied suture knot 304 disposed about a periphery of a knot tube 301. In this embodiment, the knot tube 301 includes a hollow center 301a configured to allow passage of an elongate body (not shown) as the suturing device 300 sutures the incision. However, it should be noted that in an alternative embodiment of the present invention, the elongate body (not shown) might also store the suture 302. In the alternative embodiment, the suture 302 and the pre-tied suture knot 304 are disposed about a periphery of the elongate body where the pre-tied suture knot 304 may reside within a pocket (not shown) of the elongate body.

An example of one body capable of storing the suture 302 is illustrated in FIG. 21B, and identified by reference numeral 301'. As shown, the suture storage tube 301' can include an exterior surface 340', and an interior surface 342', the interior surface 342' defining a lumen 301a'. The lumen 301a' can be configured to reduce the frictional engagement or contact between the suture 3 and the suture storage tube 301'.

The illustrated interior surface 342' can include at least two portions having differing diameters; at least one raised portion 344' and at least one recessed portion 346', optionally a plurality of raised portions 344' and a plurality of recessed portions 346', optionally in an alternating configuration, which extend longitudinally along the length of the elongated body 306'. The combination of the raised portions 344' and recessed portions 346' reduce the contact surface between the suture 302 (FIG. 21B) and the elongated body 306' and thereby reduce the frictional forces between the suture 302 and the elongated body 306' or the suture drag when the suture is moved inside the elongated body 306'. The portions 344' and 346' are another example of a structure capable of performing the function of reducing frictional engagement between a suture and the structure which selectively receives and/or restrains the suture. Accordingly, the discussion related to portions 86 and 88 of FIG. 7A also apply to portions 344' and 346' of FIG. 21B.

As illustrated, the plurality of raised portions 344' define a first inner diameter $id_1$, while the plurality of recessed portions 346' define a second inner diameter $id_2$. With an outside diameter ($od_1$) of the suture storage tube 301', $id_1$ can be about 0.030 inches, while $id_2$ can any diameter between the $od_1$ and the $id_1$. In the illustrated configuration, the $id_2$ can be between about 0.040 inches and about 0.030 inches. It will be understood by those skilled in the art that various other configurations are possible. For example, although the raised portions 344' and the recessed portions 346' are generally uniformly distributed on the interior surface 346' irregular distribution of the portions 344' and 346' is possible. Further, although the portions 344' and 346' are generally depicted as being uniform in size, shape, or general configuration, non-uniform size, shape, or configuration of portions 344' and 346' possible.

Figures 22A, 22B:
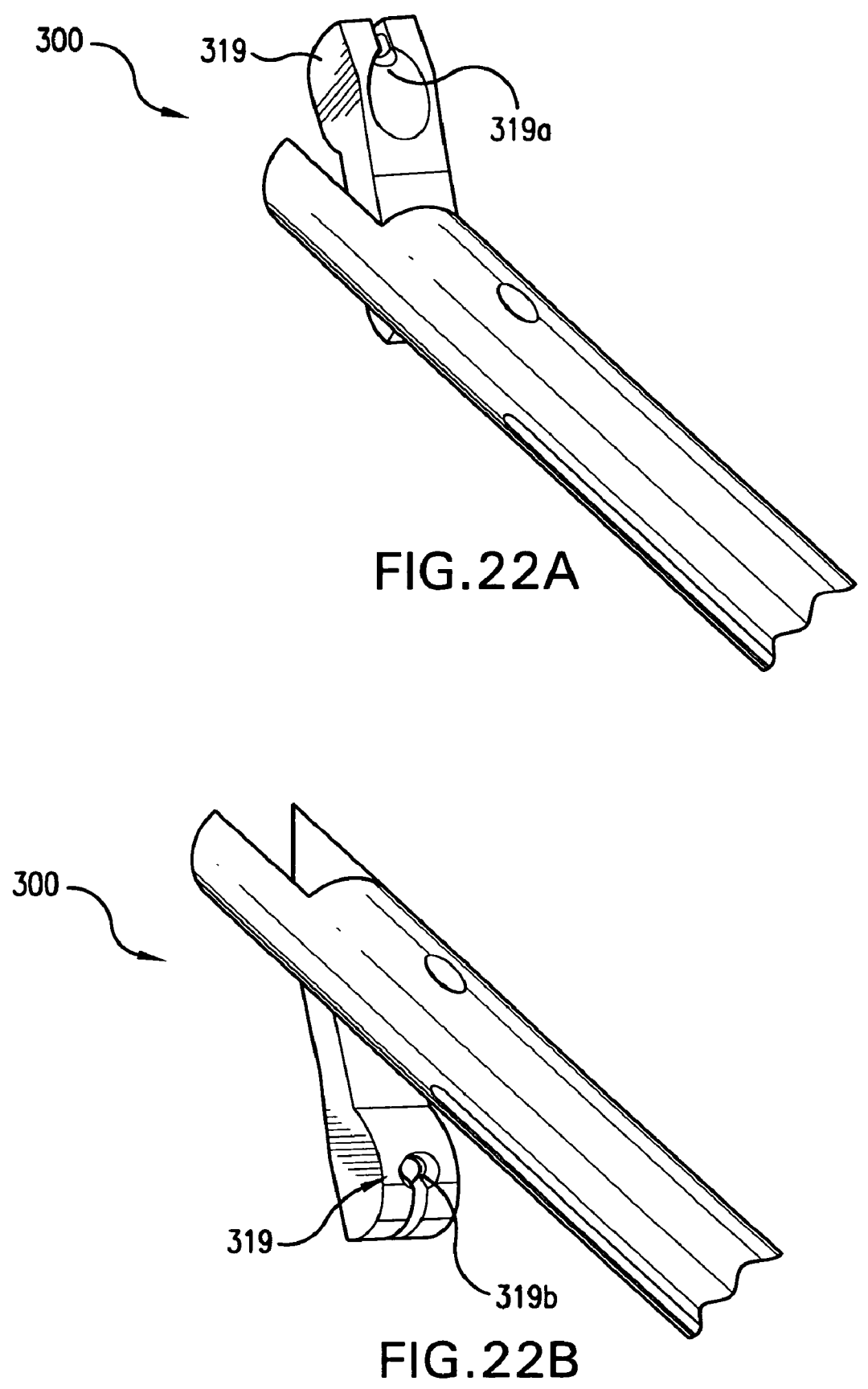
Figure 22C:
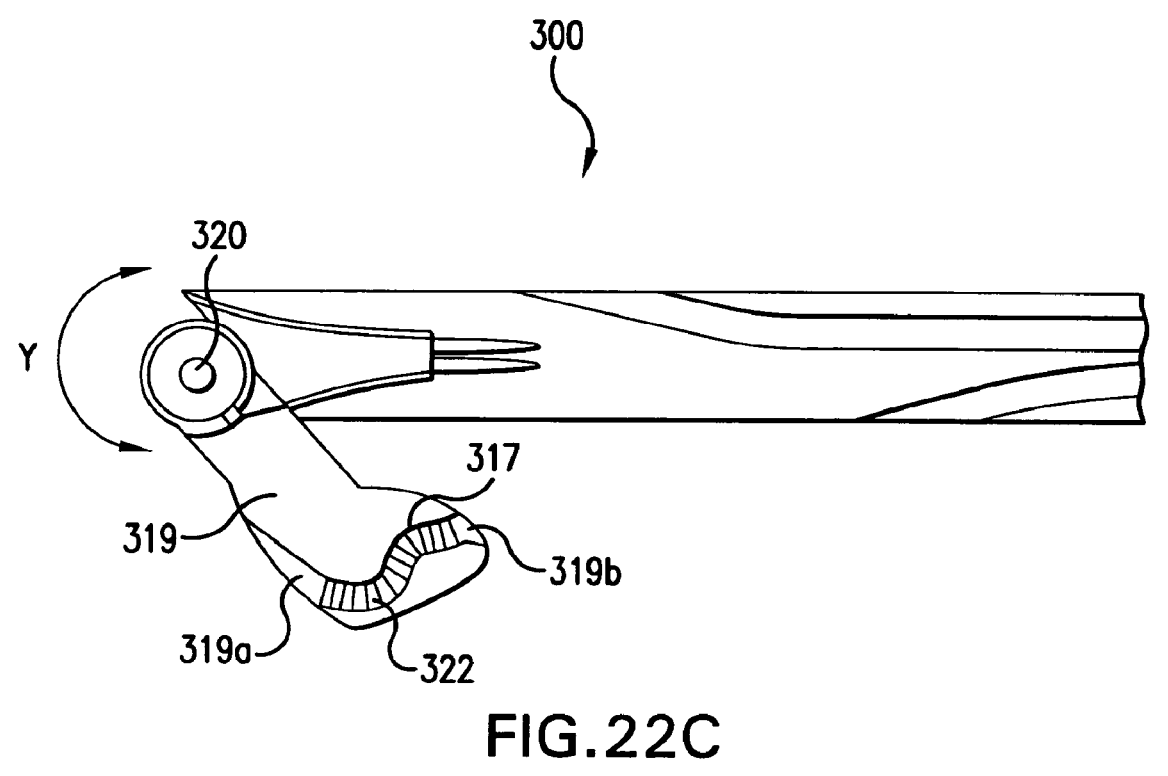

Embodiments of the suturing device of the invention may also include additional configurations for a foot, as shown with reference to FIGS. 22A through 22C. In this embodiment, the suturing device 300 includes a foot 319 having cuff pockets 319a and 319b. The configuration of the cuff pockets 319a and 319b allow the foot 319 to hold the cuffs 310 and 310' during use of the suturing device 300. The foot pivots from a first orientation shown with reference to FIG. 22A to a second orientation shown with reference to FIG. 22B via a hinge 320 as shown in FIG. 22C.

FIG. 22C shows the hinge 320, which allows rotation of the foot 319 in a direction indicated by directional arrow Y. The hinge 320 may be any device capable of rotatably coupling the foot 319 to the suturing device 300, such as pin assembly or the like. In addition to the hinge 320, the foot 319 includes a connector 322 that couples the cuffs 310 and 310' with one another. The connector 322 also includes a flexible portion 322c (shown with respect to FIG. 22C) that allows flexing of the connector 322 as the connector 322 resides within passage 317 of the foot 314. The connector also includes ends 322a and 322b that facilitate connection with the penetrator tip 308 and the needle tip 308' of the elongate bodies 306' and 306.

In an embodiment of the present invention where the suturing device 300 employs the foot 319, during use of the suturing device 300, upon insertion of the suturing device 300 within the lumen 307, a user deploys the foot 319 as shown with reference to FIG. 22A. Upon deployment of the foot 319, the user deploys the elongate body 306 (not shown) that engages with the cuff 310 (not shown) as previously described. Once the penetrator tip 308 detaches from the elongate body 306 via the push mandrel 315, or other means previously described, the user rotates the foot 319 into the orientation shown with reference to FIG. 22B. Upon orientation of the foot 319 as shown with respect to FIG. 22B, the user deploys the elongate body 306' (not shown) which engages with the cuff 310' (not shown). After the elongate body 306' engages with the cuff 310', the user retracts the elongate body 306' along with the cuffs 310 and 310' and the suture 302 to suture an incision as previously described.

Figure 23A:
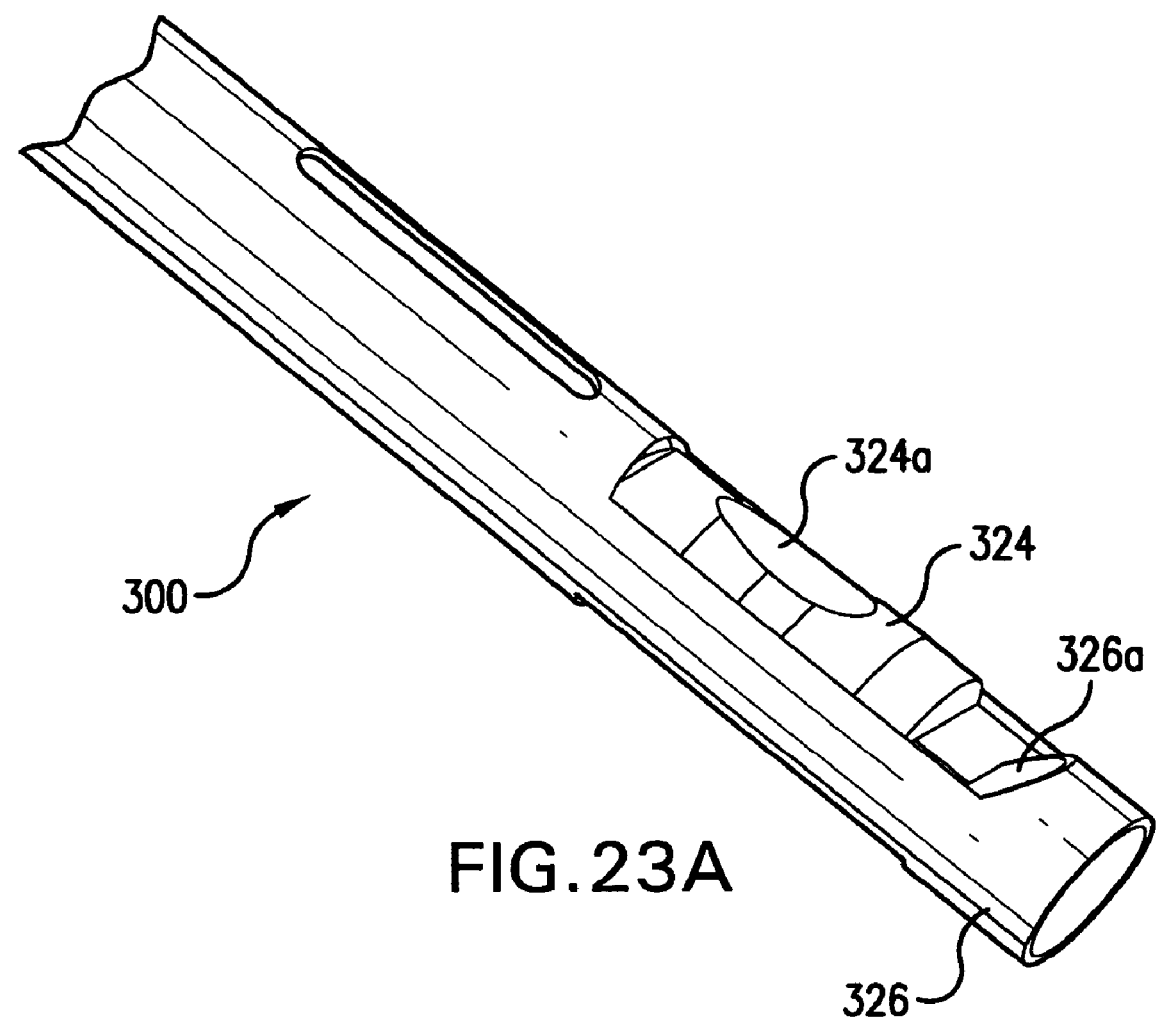
Figure 23B:
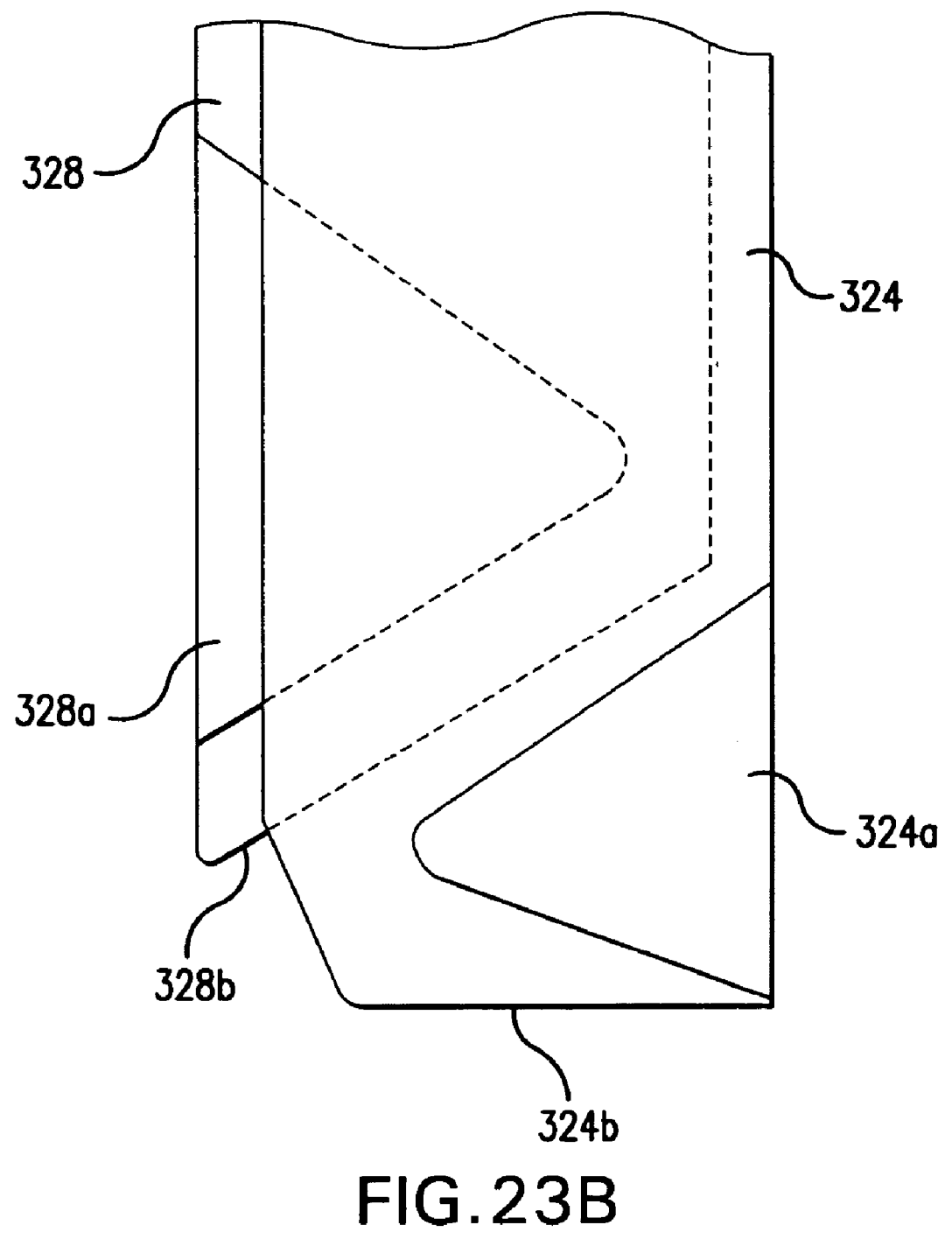
Figure 23C:
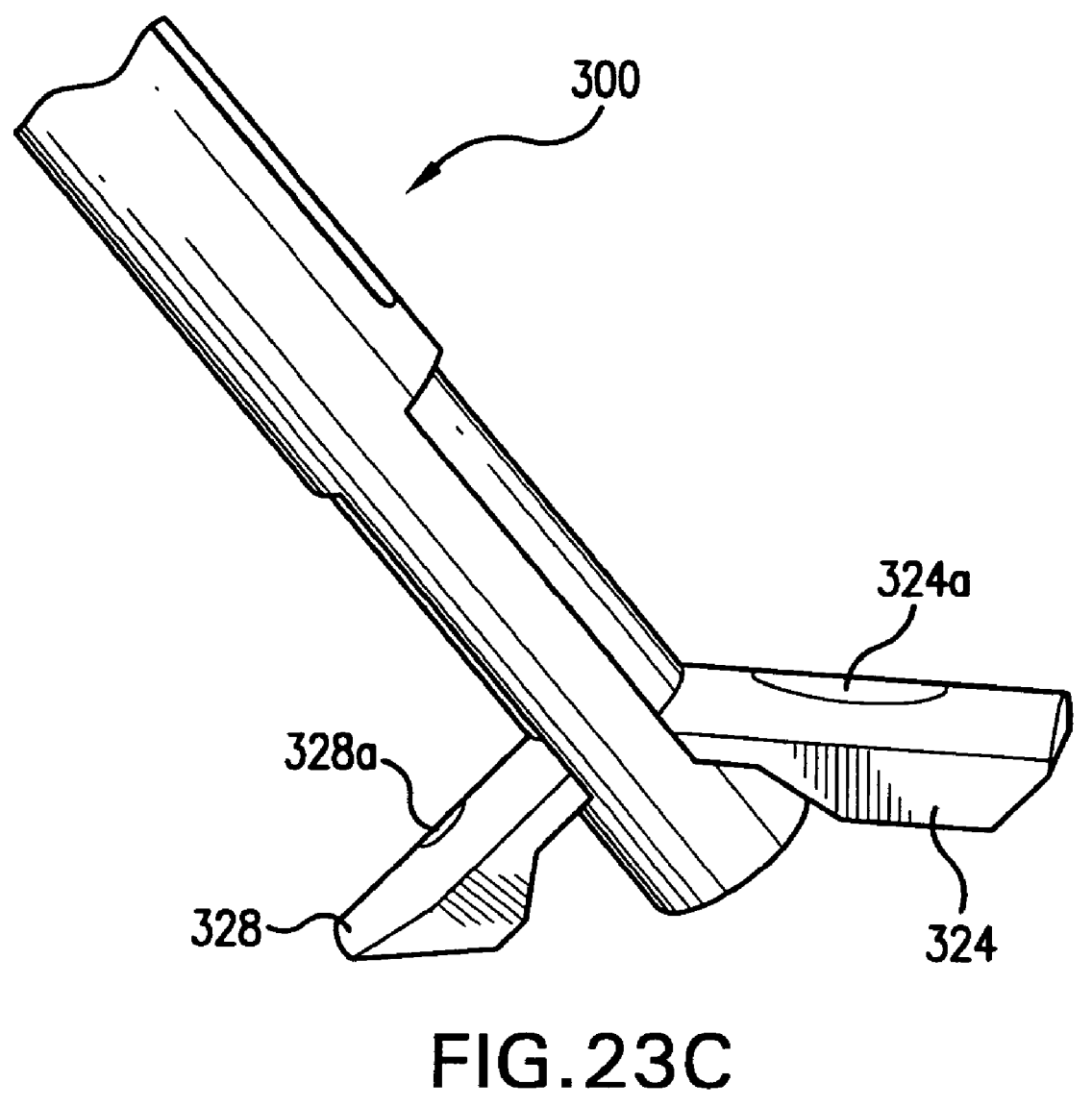

Another embodiment of the suturing device 300 includes feet 324 and 328 as shown with reference to FIG. 23A. FIG. 23A illustrates an embodiment of the present invention in which the suturing device 300 includes the feet 324 and 328. As may be seen with reference to FIG. 23B, the foot 324 is hollow such that the foot 328 fits within the foot 324 during both insertion and retraction of the suturing device 300 within the lumen 307. The feet 324 and 328 also include cuff pockets 324a and 328a and cam surfaces 324b and 328b. The configuration of the cuff pockets 324a and 328a allow placement of the cuffs 310 and 310' within the feet 324 and 328 during use of the suturing device 300; allowing engagement of the elongate bodies 306 and 306' during suturing. The cam surfaces 324a and 328a contact cam surfaces 326a in order to deploy the feet 324 and 328. Once the feet 324 and 328 deploy, the suturing device 300 attains the configuration shown with reference to FIG. 23C.

During use of a suturing device implementing the feet 324 and 328, a user inserts the suturing device into an incision as the foot 328 resides within the foot 324. Upon insertion of the suturing device within the incision, the user deploys the feet 324 and 328 by moving the feet 324 and 328 towards the cam surfaces 326a, in order to deploy the feet 324 and 328, as previously described. After deployment of the feet 324 and 328 within a lumen, the user deploys the elongate bodies 306 and 306' whereby the penetrator tip 308 and needle tip 308' engage with the cuffs 310 and 310' residing within the cuff pockets 324a and 328a. Upon engagement with the cuffs 310 and 310' the user retracts the elongate bodies 306 and 306' and sutures the incision.

Figures 24A, 24B:
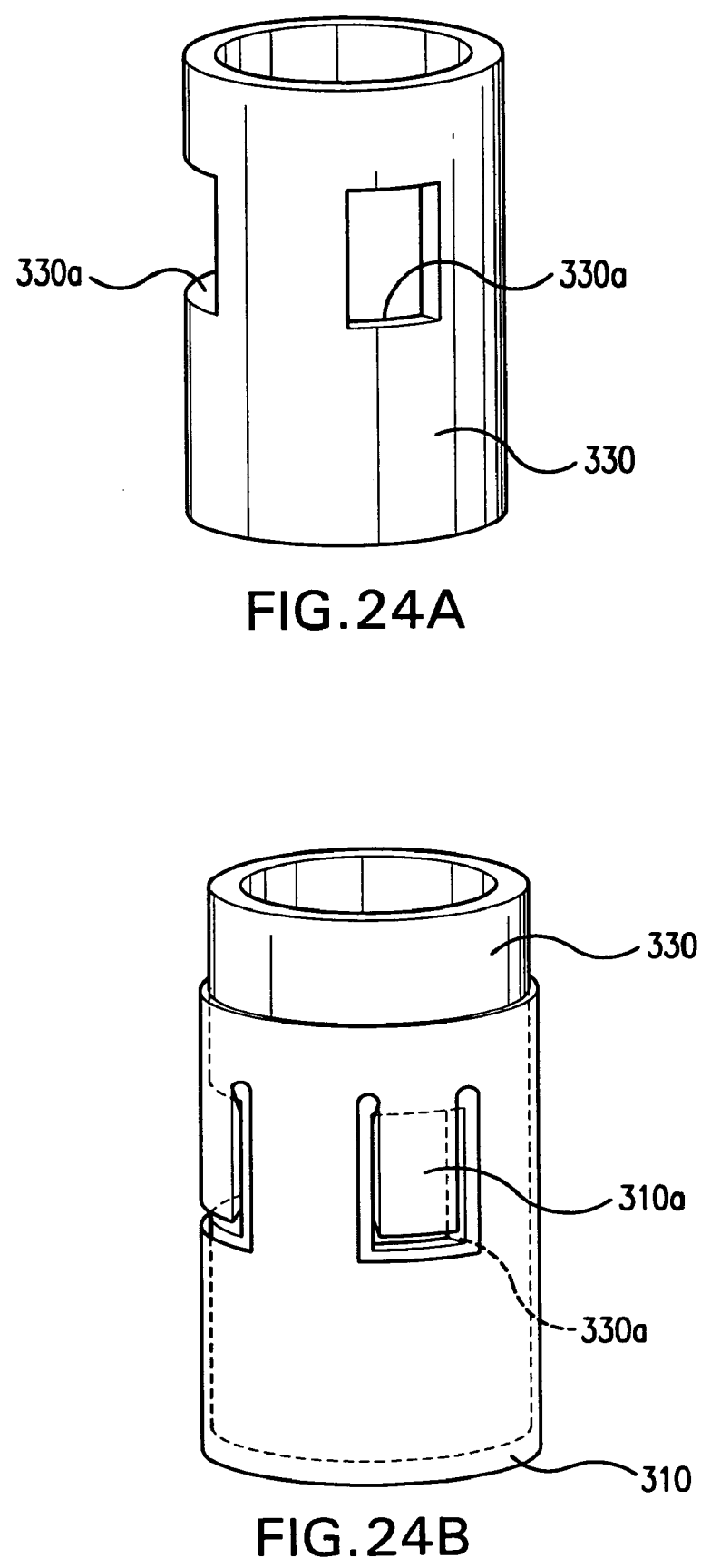

In addition to the alternative configurations for the foot of the suturing device 300, the suturing device 300 may also include alternative cuff configurations that allow engagement of the elongate bodies 306 and 306' with the link 312. An example of such an alternative configuration is shown with respect to FIG. 24A. FIG. 24A illustrates a perspective view of an alternative embodiment of the penetrator tip 330. In this embodiment, a penetrator tip 330 includes mating surfaces 330a which engage with the previously described cuff tabs 310a of the cuff 310 when the penetrator tip 330 engages with the cuff 310, as shown with reference to FIG. 24B. As such, a user detaches the elongate body 306 from the penetrator tip 330 with the push mandrel 315 after engagement of the penetrator tip windows 330a with the cuff tabs 310, as discussed with reference to the penetrator tip 308 and the cuff 310. The mating surfaces 330a may be cut-outs, such as windows, formed within the penetrator tip 330. The elongate bodies 306 and 306' may also engage with the link 312.

Figure 25A:
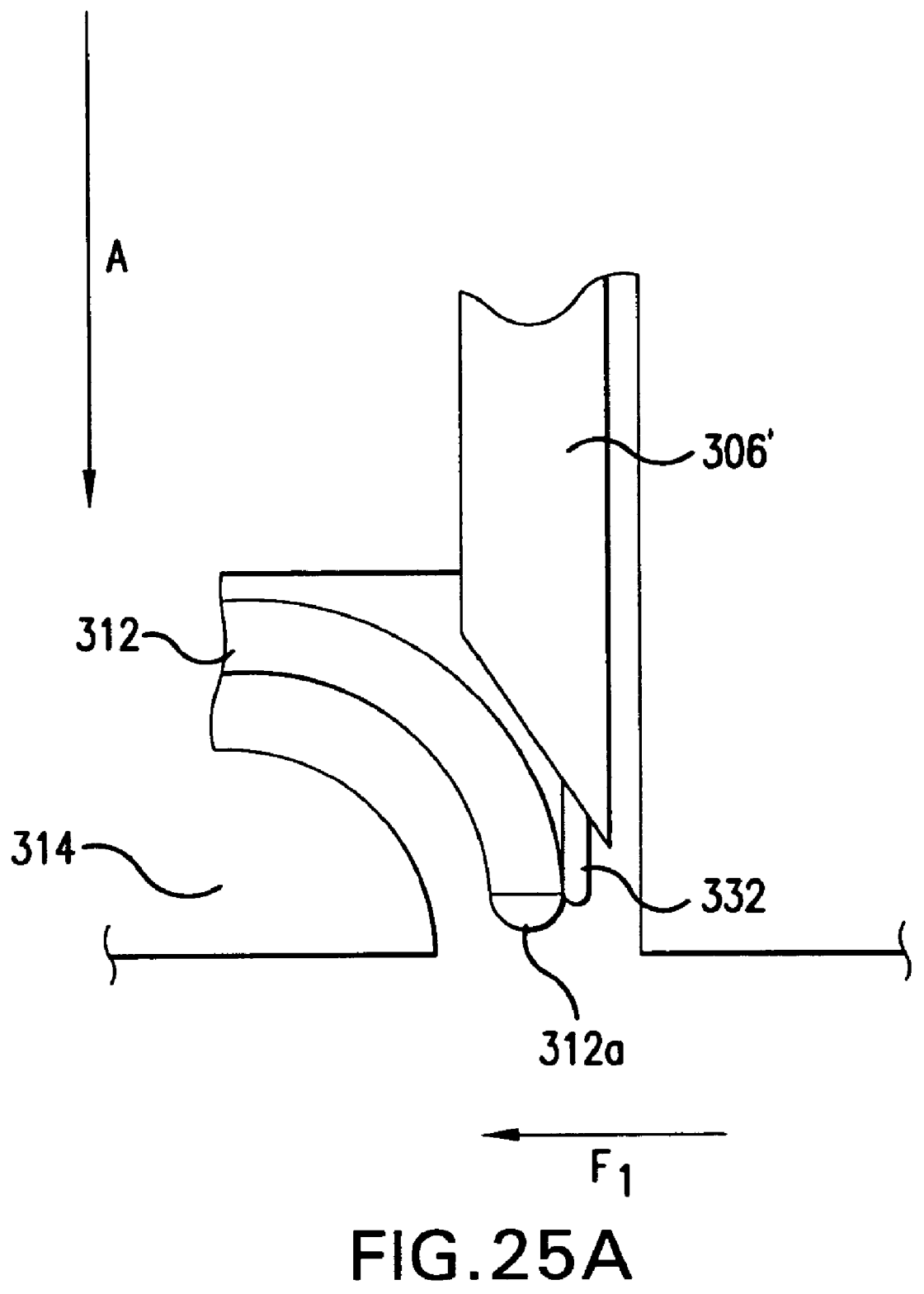

FIG. 25A shows an alternative method of coupling the elongate bodies 306 and 306' with the link 312. In this embodiment, the elongate body 306' includes a loop 332 (shown in FIG. 25B) which engages with the link 312 as the elongate body 306' enters the foot 314. In this embodiment, the link 312 is constructed of a resilient material capable of flexing in response to the loop 332 contacting the link 312, such as polypropylene or any other material having spring-like characteristics. The elongate body 306' moves in a downward direction as indicated by directional arrow A until the loop 332 comes into contact with an end 312a of the link 312. When the loop 332 contacts the end 312a, the loop 332 moves the end 312a in a direction $F_1$ indicated by directional arrow $F_1$. The catch 332 continues to move the end 312a of the link 312 in the direction $F_1$ until the loop 332 contacts the end 312a, as shown with reference to FIG. 25B.

Figures 25B, 25C:
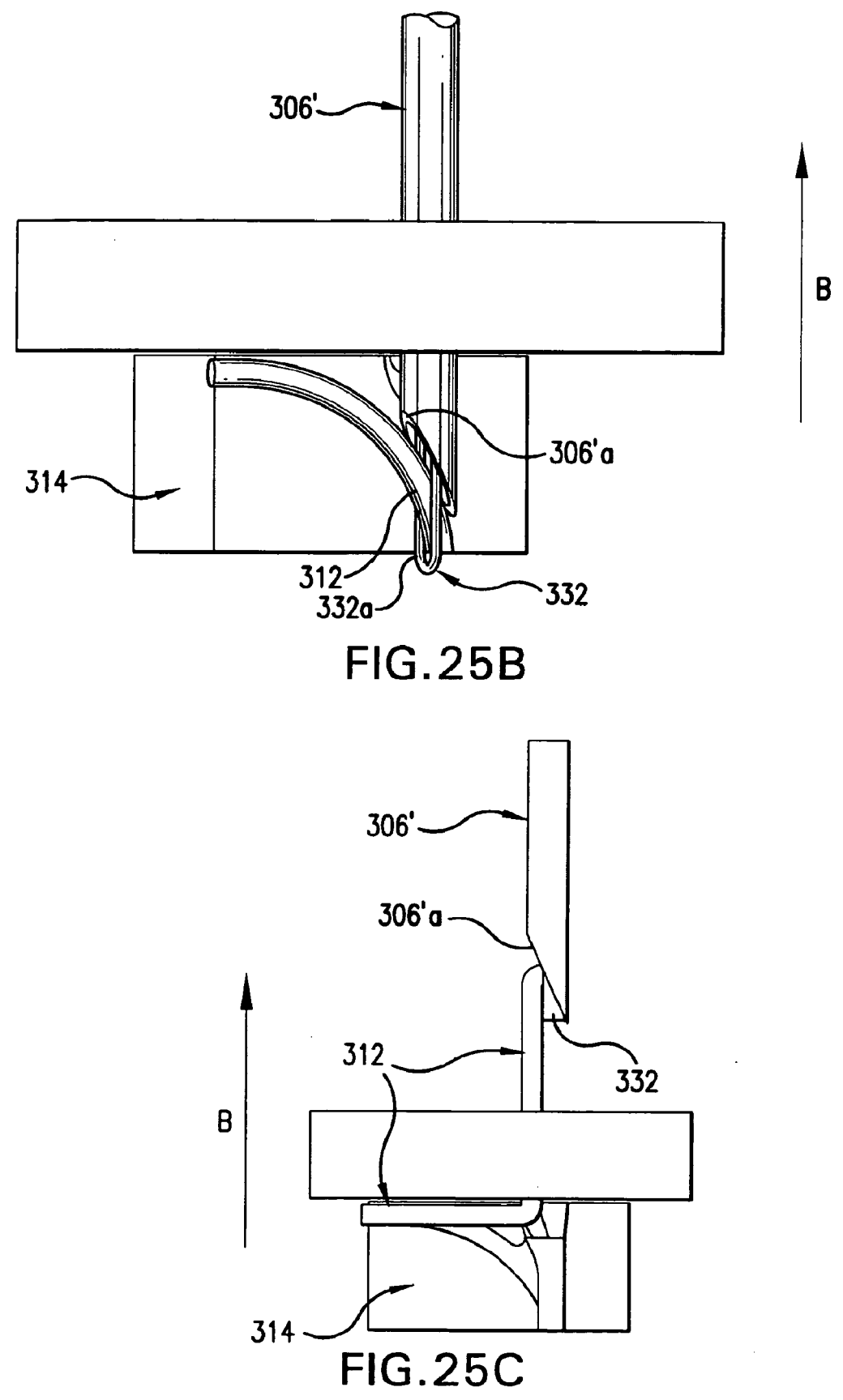

Referring to FIGS. 25A-C, the link 312 is constructed of a material having spring like properties. Therefore, when the loop 332a comes into contact with the end 312a, the resilient properties of the link 312 move the end 312a in a direction $F_2$, as indicated by directional arrow $F_2$ in FIG. 25A. The end 312a moves in the direction $F_2$ such that the end 312a moves into the loop 332a, as shown with reference to FIG. 25B. Once the end 312a moves into the loop 332a, a user retracts the loop 332 along with the end 312a and the link 312 in a direction B as indicated by directional arrow B of FIG. 25C. As the loop 332a and the catch 332 move in the direction B, the loop 332a clamps the link 312 against a surface 306'a of the elongate body 306'. Thus, during retraction of the suturing device 300 from the foot 314, the link 312 remains engaged with the elongate body 306', as shown with reference to FIG. 25C. As the elongate body 306' and the catch 332 retract from the foot 314, the catch 332 pulls the link 312 through the foot 314, also as shown with reference to FIG. 25C. While the catch 332 pulls the link 312, the cuff 310 (not shown) and the suture 302 (not shown) move through the foot 314 in order to enable suturing of an incision.

Figures 26A, 26B:
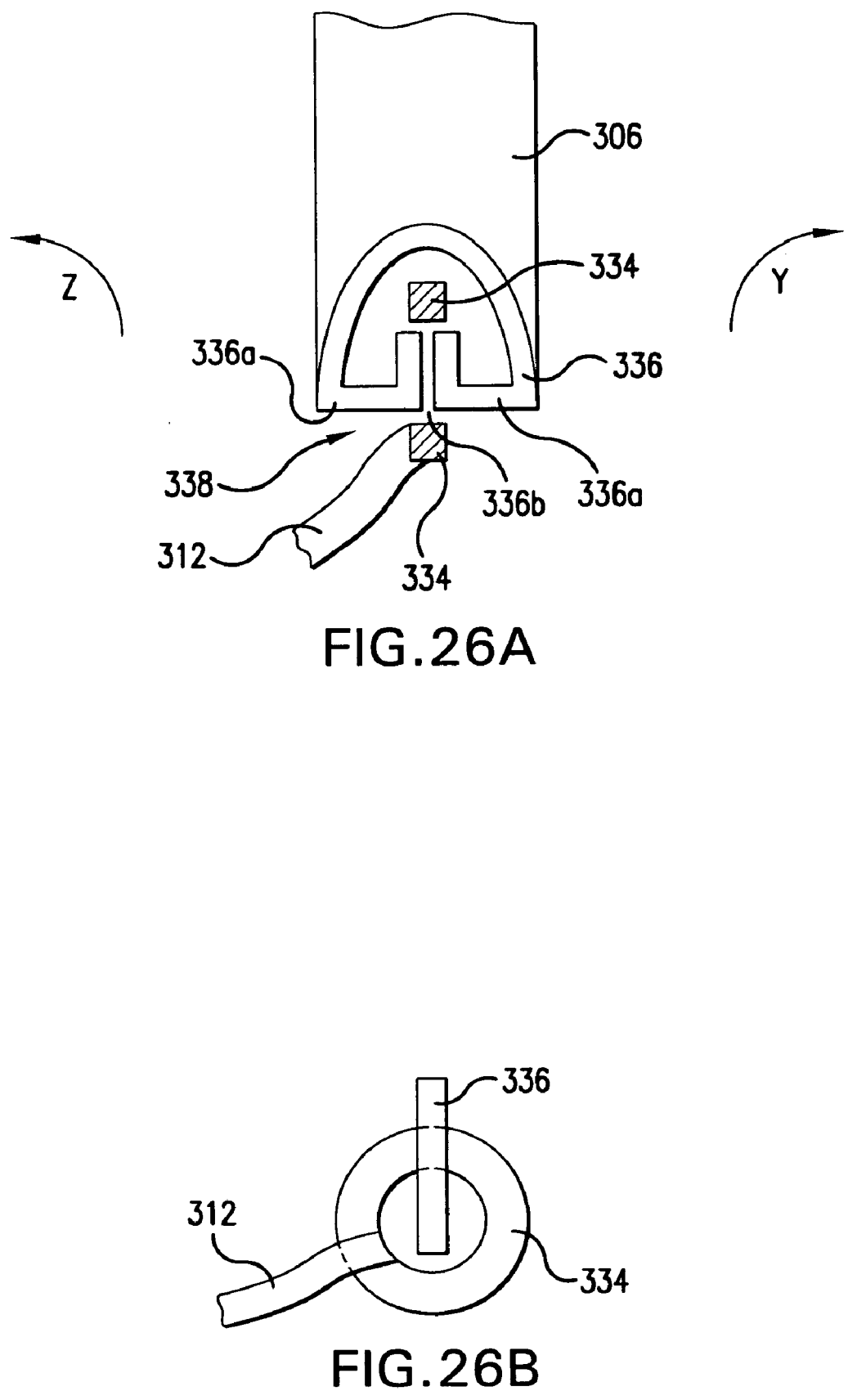

In another embodiment, the suturing device 300 may also employ a clip and ring assembly 338 which couples the elongate bodies 306 and 306' with the link 312, as shown with reference to FIG. 26A. FIG. 26A illustrates a schematic view of the clip and ring assembly 338 for coupling the elongate bodies 306 and 306' with the link 312 in accordance with an embodiment of the present invention. The elongate bodies 306 and 306' include a clip 336 in place of the penetrator tip 308 and the needle tip 308' where the clip 336 has a configuration as shown with reference to the Figure. The clips 336 include flexible arms 336a and a passageway 336b.

The clip and ring assembly 338 also includes a ring 334 that engages with the clip 336. The link 312 couples with the ring 334 using any suitable technique, such as tying or the like. The ring 334 has a circular configuration as shown with respect to FIG. 26B such that as the elongate bodies 306 and 306' engage with the foot 314, the clip 336 couples with the ring 334. As the clips 336 engage with the ring 334, the flexible arms 336a flex in a direction indicated by directional arrows Y and Z thereby increasing a width $W_i$ of the passageway 336b in order to allow passage of the ring 334 through the clip 336 as shown with regards to FIG. 28C.

Figures 26C, 26D:
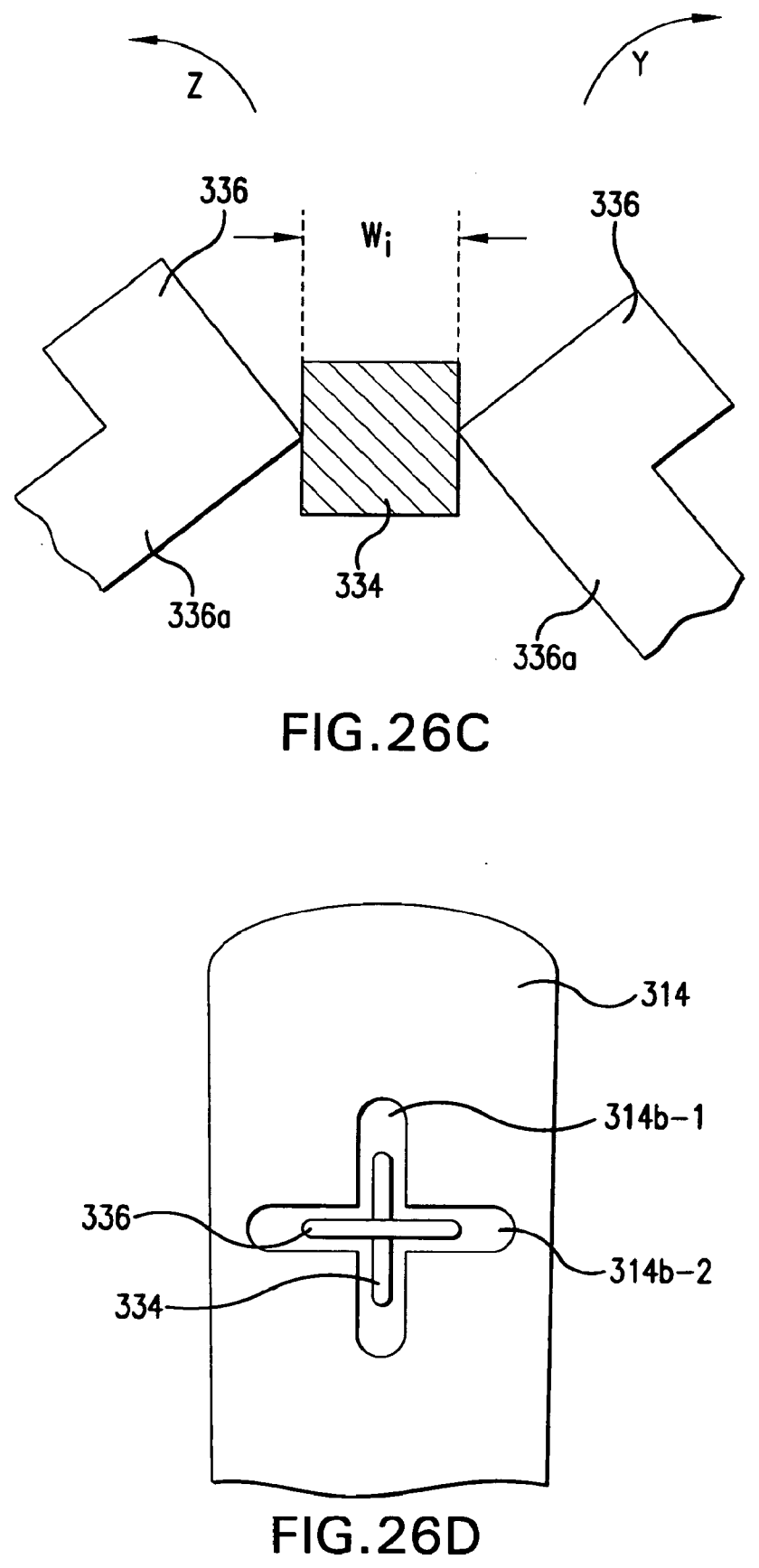

Referring to FIG. 26D, there is shown a top view of the foot 314 where the foot 314 includes cuff pockets 314b-1 and 314b-2. The cuff pocket 314b-1 holds the ring 334 prior to engagement with the clip 336. The cuff pocket 314b-2 is configured such that as the elongate bodies 306 and 306' enter the foot 314, the clips 336 enter the cuff pocket 314b-2 and engage with the ring 334 as shown with reference to the Figure. Once the clip 336 engages with the ring 334, the clip 336 coupled with the elongate body 306 detaches from the clip 336 while the elongate body 306' remains engaged with the clip 336. During retraction of the elongate bodies 306 and 306' from the foot 314, the elongate body 306' pulls the link 312 and the suture 302 through the foot 314 in order to suture an incision.

Figures 27, 28:
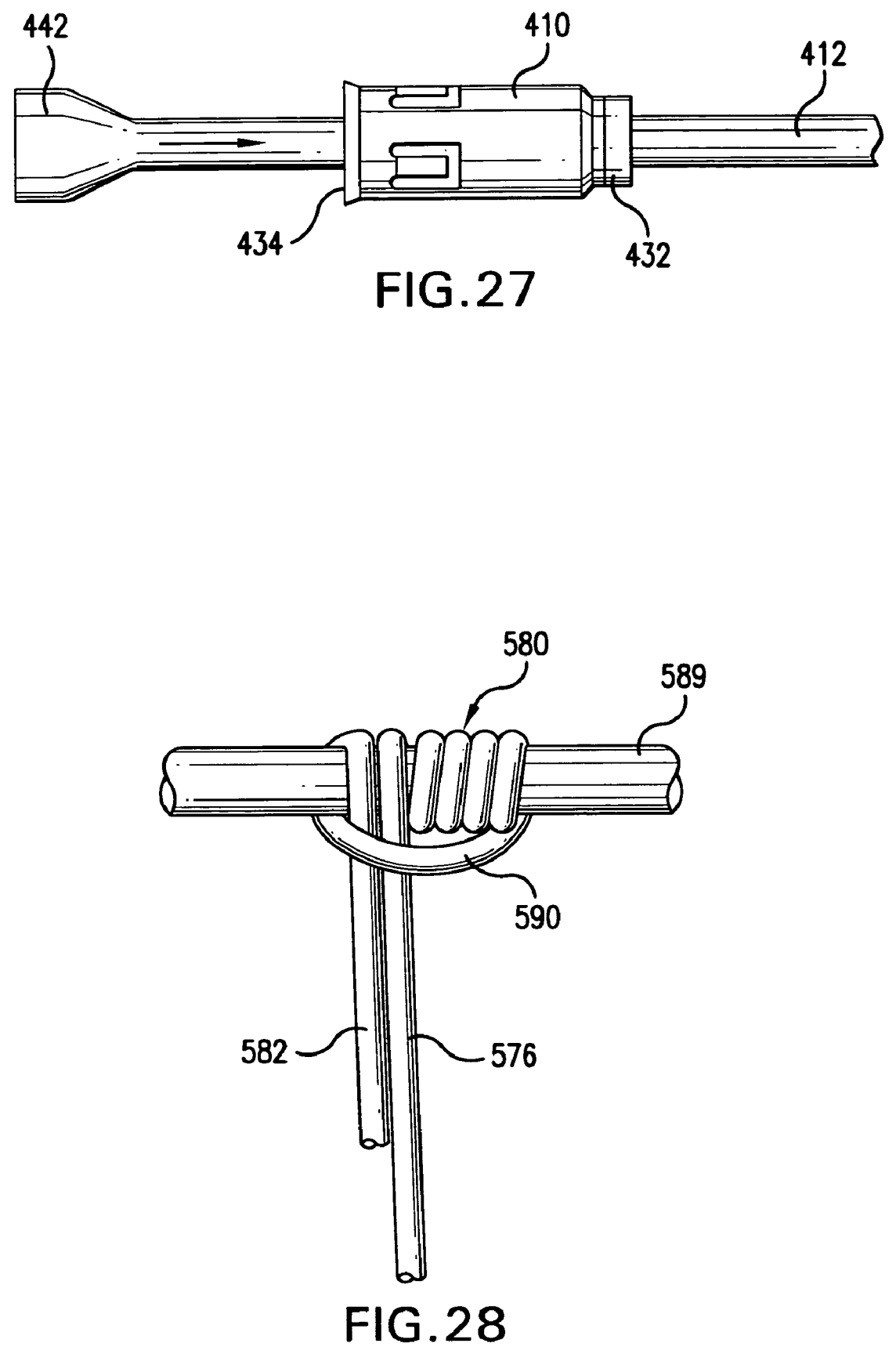

FIG. 27 shows an embodiment of a cuff 410 and link 412 assembly that may be provide with the various embodiments of the present invention. Cuff 411 has a penetrator tip receiving end 434 and a tapered end 432. Link 412 has two ends 442 (only one shown in FIG. 27). An example of one link material is expanded Polytetrafluoroethylene (ePTFE). PTFE is commonly referred to as Teflon. ePTFE is particularly suited for use as the link material in the vessel closure devices described herein because of its low friction, high strength properties.

To assemble the link and cuff assembly, a length of link material is first threaded through the cuff. The end of the link material extending from the penetrator tip receiving end 434 of the cuff 410 is then heated so that it expands. The link is then pulled through the cuff 410 such that the expanded end portion 442 is seated in the interior tapered end 432 of the cuff 410.

The various embodiments of the suturing device may include any of a variety of types of suture, such as braided or monofilament. The suture material may be absorbable or nonabsorbable and may be made of polyester, polypropylene, polyglycolic acid, nylon, silk or any of a variety of suture materials known in the art. Suture material coated with antibiotics or other antimicrobial agents may also be provided with the suturing devices of the present invention.

An exemplary suture material is TEVDEK II®, a braided polyester suture material that is impregnated with PTFE and manufactured by Genzyme Biosurgery of Cambridge, Mass. An exemplary monofilament suture material is DEKLENE II®, a polypropylene suture material also manufactured by Genzyme Biosurgery. Another exemplary monofilament suture material is nylon monofilament, also manufactured by Genzyme Biosurgery. While braided polyester and monofilament polypropylene or nylon are suitable suture materials that may be used with the devices of the present invention, monofilament suture materials may require post-manufacturing processing in order to form the pre-tied knot of the embodiments described with reference to FIGS. 11A through 11E and 14A through 21.

Monofilament suture material tends to be stiffer relative to braided suture material. As such, forming a bight of suture for the purpose of providing a pre-tied knot is more difficult with monofilament suture than with the more flexible braided suture. The monofilament suture material can tend to straighten itself out after being looped to form a bight 80 (shown in FIGS. 11Ai and 11Aii). Therefore, in order to provide a bight of monofilament suture that is releasably disposed on the shaft of the device without unraveling, such as shown in FIGS. 11Ai and 11Aii, FIG. 15A (pre-tied knot 104), and FIG. 21 (pre-tied knot 304), the loops forming the bight are heated to set the bight. The heating of the bight of monofilament suture to set the bight is performed after the suture has undergone any manufacturing procedures that may include drawing, annealing or any other procedure that employs heat to manufacture the suture material.

A method of forming a pretied knot for a suturing device of the present invention includes providing a length of monofilament suture having a first end, wrapping a portion of the length of monofilament suture around a mandrel to form a looped configuration spaced from the first end, and heating the wrapped portion to a temperature below the melting point of the monofilament suture such that upon removal of the mandrel, the wrapped portion remains in the looped configuration.

The bight of the suture includes at least one loop. The heating of the at least one loop is performed to set the bight in the looped configuration. The temperature is kept below the melting temperature of the suture material, yet is selected to cause the suture to remain in the formed looped configuration after the bight is removed from the heat. The temperature is selected so as not to adversely affect properties such as strength of the suture.

In one exemplary heating process, a length of size 3/0 polypropylene suture is looped around a mandrel to form a bight which is heated at a temperature between about 240° F. to about 260° F., or nominally about 250° F., for about 3 to about 5 seconds. The heat is provided by a blowing heat source such as a heat gun that provides an air flow at a rate of about 10 to about 30 standard cubic feet per hour (scfh), or nominally about 20 scfh. The heating of the formed bight may be accomplished in an oven that is heated to about 200° F. to about 280° F. When the bight is formed using an oven, the amount time that the bight is held in the heat of the oven is approximately 1 minute to about 15 minutes. The specific heating temperatures and times may be selected as appropriate for different suture sizes or types, or different types of bight configurations.

In another embodiment, a monofilament nylon suture material may be provided to form a pre-tied knot in a suturing device of the present invention. The temperature at which a bight formed with size 3/0 nylon suture is heated to set the bight is about 190° F. to about 210° F., and nominally about ° F., for about 3 to about 5 minutes with a blowing heat source such as a heat gun. In an oven, the temperature used at which the bight is set is about 190° F. to about 210° F., or nominally about 200° F. for about 1 minute to about 15 minutes.

FIG. 28 shows a bight 580 of monofilament suture wrapped around a mandrel 589 in preparation for heating the loops of the bight to set the bight. The mandrel may be a polyimide shaft or tube having a diameter of about 0.65 mm, for example. In the example shown in FIG. 28, the suture is size 3/0 and is wrapped to form a looped configuration which defines a clinch knot. To wrap the suture as shown in FIG. 28, a length of suture is held against the mandrel with a first end 576 oriented across the mandrel. The second end of the length of suture is wrapped five times around the mandrel. The second end is then wrapped over the first end to form loop 590 transverse to the first five loops. The second end is then looped behind the mandrel and wrapped over the mandrel in the opposite direction from the first five loops. The second end is then routed through loop 590 to form the pre-arranged or pre-tied knot.

The present invention offers surgeons an automated method for delivering a pre-tied knot to an incision formed in a lumen. The present invention minimizes the problems associated with a surgeon manually delivering a knot to an incision site. Thus, the present invention reduces the time required to accurately and precisely place a suture knot in close proximity to an incision formed in a lumen, thereby decreasing both the overall time a patient spends in procedure and the costs associated with the procedure.

While illustrative embodiments of the invention are disclosed herein, it will be appreciated that numerous modifications and other embodiments may be devised by those skilled in the art. For example, the various features of each embodiment may be altered or combined to obtain the desired device or method characteristics. Therefore, it will be understood that the appended claims are intended to cover all such modifications and embodiments that come within the spirit and scope of the present invention.

What is claimed is:

1. A system for suturing a blood vessel, the vessel having a vessel wall, the system comprising;
   a shaft suitable for insertion along the tissue tract and into the vessel through a puncture, shaft comprising at least one lumen including at least one friction reducing structure, the at least one friction reducing structure comprises at least one recessed portion and at least one raised portion disposed an interior surface of the lumen;
   a needle having a proximal end and a distal end suitable for forming a needle path through the vessel wall, the needle having a recessed engagement surface adjacent the distal end;
   a flexible filament disposed within the lumen; and
   a fitting attached to the filament and releasably supported by a foot mounted near a distal end of the shaft.

2. The system of claim 1, wherein the needle is flexible, and wherein the fitting is releasably supported within a receptacle surface oriented to laterally deflect the advancing needle toward the fitting.

3. The system of claim 2, further comprising a slot disposed along the receptacle surface, wherein the filament is releasably disposed in the slot, the slot configured to avoid engagement of the needle with the suture.

4. The system of claim 3, wherein the slot comprises at least one friction reducing structure.

5. The system of claim 1, wherein the at least one recessed portion and the at least one raised portion are disposed in the interior surface of the lumen in an alternating fashion.

6. A system for suturing a puncture of a blood vessel within a tissue tract, the vessel having a vessel wall and defining an axis, the system comprising:
   a shaft having a proximal handle and a distal end suitable for insertion along the tissue tract and into the vessel through the puncture, the distal end comprising at least one lumen with at least one friction reducing structure formed therein, the at least one friction reducing structure comprises a plurality of recessed portions and a plurality of raised portions disposed an interior surface of the lumen;
   a foot mounted near the distal end of the shaft, the foot having a plurality of needle receptacles extendable laterally from the shaft;
   a flexible filament extending between the needle receptacles of the foot, at least a portion of the flexible filament being disposed with that at least one lumen;
   a plurality of needles advanceable distally and laterally from the shaft, through the vessel wall outside the puncture, and to the needle receptacles of the foot.

7. The system of claim 6, further comprising a plurality of fittings disposed adjacent the receptacles of the foot, the fittings securely engaging the needles so that the needles, fittings, and at least a portion of the filament can be withdrawn through the vessel wall along at least one of the needle paths formed by the needles without threading the filament into the needles, the at least one friction reducing structure reducing the frictional contact between the filament and the lumen as the filament is withdrawn through the vessel wall.

8. The system of claim 6, wherein the foot comprises an elongate body defining an axis, the foot articulatable from a small profile configuration to a large profile configuration by actuating the proximal handle so that the foot slides axially and pivots laterally within the vessel.

9. The system of claim 6, wherein the plurality of recessed portions and the plurality of raised portions are disposed in the interior surface of the lumen in an alternating fashion.

10. The system of claim 6, wherein the flexible filament is a suture.

11. The system of claim 10, wherein the suture is a monofilament suture.

12. A device for suturing an opening in a tissue, the device comprising:
   a shaft having a proximal end and a distal end and defining an axis therebetween, the shaft having a size and configuration suitable for insertion through the opening in the tissue;
   an elongate foot movably mounted to the shaft;
   an actuator extending along the shaft distally to the foot, movement of the actuator sliding the foot axially and pivoting the foot from a low profile configuration aligned along the shaft to a deployed configuration extending laterally from the shaft;
   a suture supported by the foot;
   a suture supporting structure having a lumen with at least one friction reducing portion, the at least one friction reducing portion comprises a plurality of recessed portions and a plurality of raised portions disposed an interior surface of the lumen, the suture supporting structure receiving at least a portion of the suture within the lumen; and
   a needle advanceable from the shaft through the tissue and to the deployed foot.

13. The device as recited in claim 12, wherein the suture supporting structure comprises a tubular structure disposed within the shaft.

14. The device of claim 13, wherein a first length of suture extends between a first fitting at the first end of the probe to a second fitting at the second end of the probe, and wherein a second length of suture extends from a third fitting at the first end of the probe to a forth fitting at the second end of the probe, and wherein each fitting securingly engages an associated needle to draw ends of the first and second length of suture through the vessel wall and form a plurality of loops across the puncture.

15. The device of claim 13, wherein the plurality of recessed portions and the plurality of raised portions are disposed in the interior surface of the lumen in an alternating fashion.

16. The device of claim 13, wherein the suture is a monofilament suture.

17. The device as recited in claim 12, wherein the suture supporting structure is integrally formed within the shaft.

18. The device of claim 12, wherein the foot has a first end and a second end, and wherein a plurality of needles are extendable from the shaft to the ends of the foot.

* * * * *